(12) United States Patent
Pathak et al.

(10) Patent No.: US 12,279,882 B2
(45) Date of Patent: Apr. 22, 2025

(54) MOVEMENT DISORDER DIAGNOSTICS FROM VIDEO DATA USING BODY LANDMARK TRACKING

(71) Applicant: Google LLC, Mountain View, CA (US)

(72) Inventors: Anupam J. Pathak, San Carlos, CA (US); Jian Cui, Fremont, CA (US); Dongeek Shin, Mountain View, CA (US)

(73) Assignee: GOOGLE LLC, Mountain View, CA (US)

( * ) Notice: Subject to any disclaimer, the term of this patent is extended or adjusted under 35 U.S.C. 154(b) by 324 days.

(21) Appl. No.: 17/872,438

(22) Filed: Jul. 25, 2022

(65) Prior Publication Data

US 2023/0027320 A1 Jan. 26, 2023

Related U.S. Application Data

(60) Provisional application No. 63/225,297, filed on Jul. 23, 2021.

(51) Int. Cl.
*A61B 5/00* (2006.01)
*A61B 5/11* (2006.01)
*G06T 7/00* (2017.01)

(52) U.S. Cl.
CPC .......... *A61B 5/4082* (2013.01); *A61B 5/0077* (2013.01); *A61B 5/1124* (2013.01);
(Continued)

(58) Field of Classification Search
CPC ... A61B 5/4082; A61B 5/0077; A61B 5/1124; A61B 5/4842; A61B 2562/0204;
(Continued)

(56) References Cited

U.S. PATENT DOCUMENTS 9,775,899 B2 * 10/2017 Burkly ............... G01N 33/6896
10,264,971 B1 * 4/2019 Kennedy ............. A61B 5/6804
(Continued)

OTHER PUBLICATIONS

Lipsmeier et al., "Evaluation of Smartphone-Based Testing to Generate Exploratory Outcome Measures in a Phase 1 Parkinson's Disease Clinical Trial", Movement Disorders, vol. 33, No. 8, 2018, pp. 1287-1297.
(Continued)

*Primary Examiner* — Baisakhi Roy
(74) *Attorney, Agent, or Firm* — DORITY & MANNING P.A.

(57) ABSTRACT

A method for facilitating a Parkinson's Disease ("PD") assessment of a patient includes capturing first video of a patient performing first test movements while holding the mobile device; capturing second video of the patient performing second test movements while maintaining the mobile device on their person; capturing third video of the patient performing third test movements including standing and walking; capturing one or more IMU readings using an IMU of the mobile device; processing the first video, the second video, and the third video according to (i) a hand landmark model to generate one or more hand biomarkers, (ii) a face landmark model to generate one or more face biomarkers, and (iii) a body landmark model to generate one or more body biomarkers; and determining an assessment score based on a standardized PD assessment by processing the biomarkers.

20 Claims, 39 Drawing Sheets

(52) U.S. Cl.
CPC .......... *A61B 5/4842* (2013.01); *G06T 7/0012* (2013.01); *A61B 2562/0204* (2013.01); *A61B 2562/0219* (2013.01); *G06T 2207/10016* (2013.01); *G06T 2207/20081* (2013.01); *G06T 2207/20084* (2013.01); *G06T 2207/30004* (2013.01)

(58) Field of Classification Search
CPC .......... A61B 2562/0219; G06T 7/0012; G06T 2207/10016; G06T 2207/20081; G06T 2207/20084; G06T 2207/30004
See application file for complete search history.

(56) References Cited

U.S. PATENT DOCUMENTS

| | | | | |
|---|---|---|---|---|
| 2012/0019245 A1* | 1/2012 | Reddy | ................ | G01R 33/5601 324/309 |
| 2018/0024150 A1* | 1/2018 | Ikeuchi | ................ | G01N 33/50 436/71 |
| 2019/0192013 A1* | 6/2019 | Johanning | .............. | A61B 5/748 |
| 2020/0268251 A1* | 8/2020 | Hao | ........................ | A61B 5/1114 |
| 2020/0268339 A1* | 8/2020 | Hao | ........................ | A61B 6/032 |
| 2020/0321121 A1* | 10/2020 | Neumann | .............. | G06N 5/022 |
| 2020/0353239 A1* | 11/2020 | Daniels | ................... | A61B 5/296 |
| 2023/0181075 A1* | 6/2023 | Hashimoto | ........... | A61B 5/7278 600/595 |
| 2024/0065622 A1* | 2/2024 | Hashkes | ................. | G16H 50/50 |
| 2024/0249498 A1* | 7/2024 | Galeotti | ................ | G06T 7/0012 |
| 2024/0257926 A1* | 8/2024 | Langel | ................... | G16H 10/20 |

OTHER PUBLICATIONS

Zhan et al., "Using Smartphones and Machine Learning to Quantify Parkinson Disease Severity", JAMA Neurology, vol. 75, No. 7, 2018, pp. 876-880.

* cited by examiner

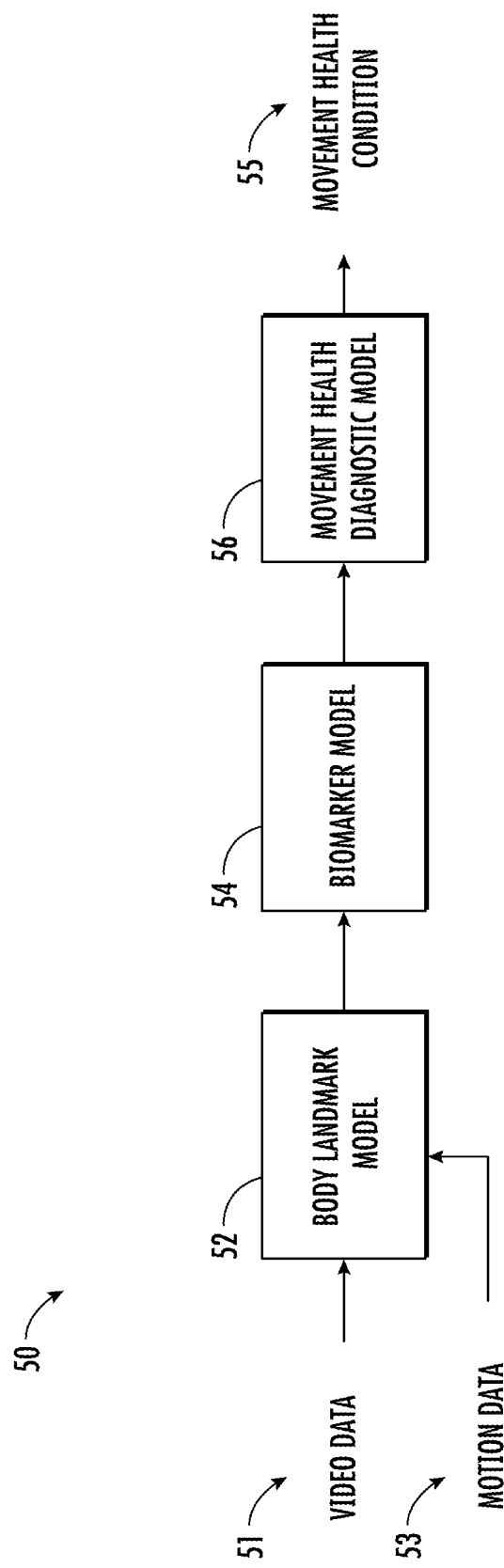

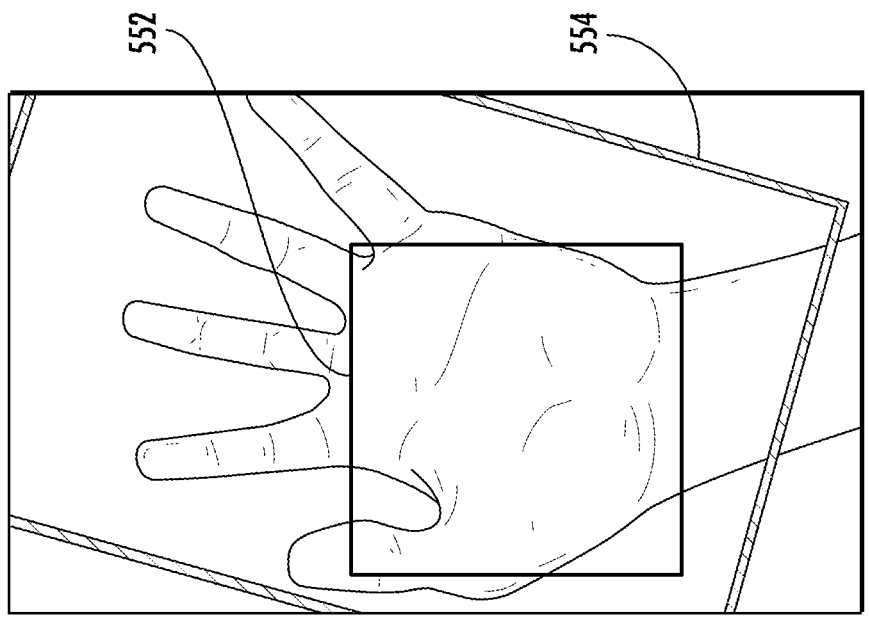
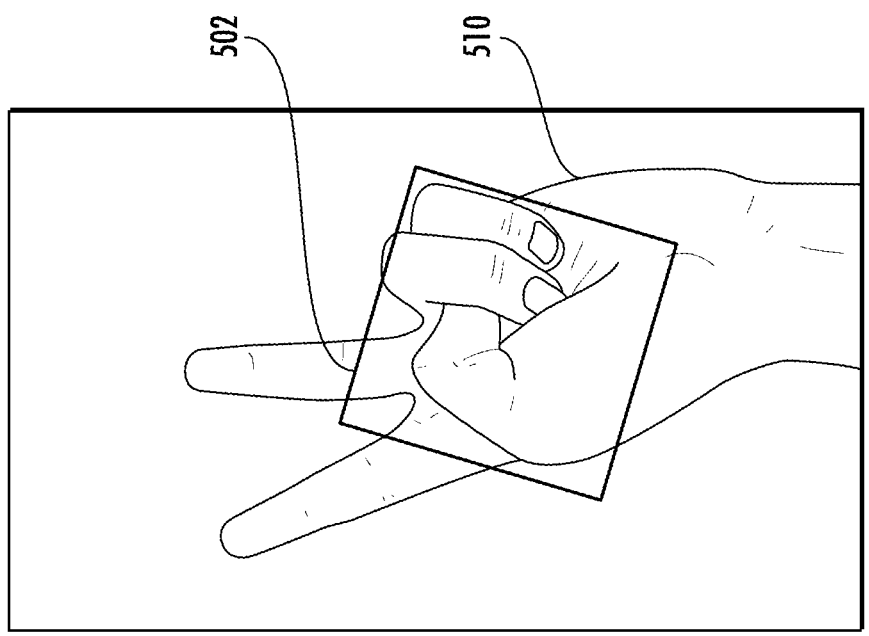

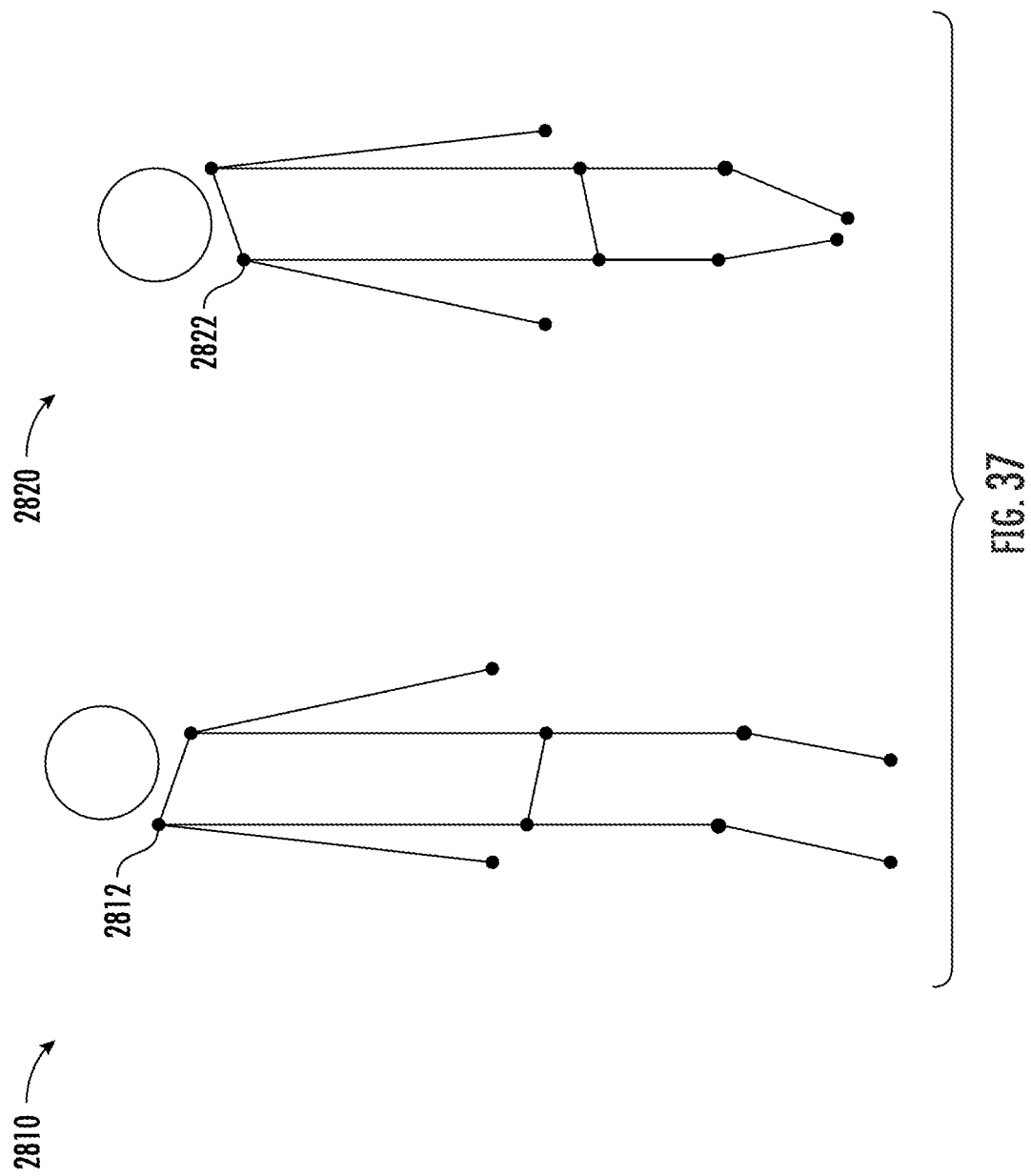

MOVEMENT DISORDER DIAGNOSTICS FROM VIDEO DATA USING BODY LANDMARK TRACKING

CROSS-REFERENCE TO RELATED APPLICATIONS

This application claims priority to U.S. Provisional Application Ser. No. 63/225,297, filed on Jul. 23, 2021, the entire contents of which are hereby incorporated by reference.

FIELD

The present disclosure relates generally to diagnostics of movement disorders. More particularly, the present disclosure relates to movement disorder diagnostics from video data using body landmark tracking.

BACKGROUND

The field of neurology has had a long history, stemming from the first attempts to understand extremely complex brain disorders with a limited set of tools and technology. Movement disorders like Parkinson's Disease (PD), Essential Tremor (ET), Multiple Sclerosis (MS), etc. are assessed using established clinical ratings that rely on crude measurements, and rough judgements by the doctor. Hand tremor, for example, is visually assessed with frequency and amplitude subjectively scored (as opposed to using any instrument to quantify the movement). Clinical scales, such as the UPDRS scale for Parkinson's Disease, are the gold standard for clinical assessment but do not use any kind of instrument to assess motor or brain function. The lack of objective diagnosis can lead to misdiagnosis and/or difficulties in assessing effectiveness of interventions. In addition, many patients do not frequently visit neurologists or other practitioners capable of assessing movement disorders, leading to poor resolution of testing and assessment. Furthermore, clinical tools used in assessing movement disorders may not be readily available and/or viable for consumers.

SUMMARY

Aspects and advantages of embodiments of the present disclosure will be set forth in part in the following description, or can be learned from the description, or can be learned through practice of the embodiments.

One example aspect of the present disclosure is directed to a computing system for generating movement disorder diagnostics including one or more processors and one or more non-transitory computer-readable media that collectively store: a machine-learned body landmark model configured to obtain video data and identify a plurality of body landmark positions within the video data; a machine-learned biomarker model configured to determine one or more biomarkers based at least in part on the plurality of body landmark positions; a machine-learned movement health diagnostic model configured to predict a movement health condition based at least in part on the one or more biomarkers; and instructions, that, when implemented, cause the one or more processors to perform operations, the operations including: obtaining the video data, the video data including one or more frames; providing the video data as input to the machine-learned body landmark model; receiving, as an output from the machine-learned body landmark model, data descriptive of the plurality of body landmark positions within the video data; providing the data descriptive of the plurality of body landmark positions as input to the machine-learned biomarker model; receiving, as an output from the machine-learned biomarker model, data descriptive of the one or more biomarkers; providing the data descriptive of the one or more biomarkers to the machine-learned movement health diagnostic model; and receiving, as an output from the machine-learned movement health diagnostic model, data descriptive of a movement health condition.

Another example aspect of the present disclosure is directed to a computer-implemented method for generating movement disorder diagnostics including obtaining, by a computing system including one or more computing devices, video data including one or more frames; determining, by the computing system, a plurality of body landmark positions based at least in part on the video data; and determining, by the computing system, a movement health condition based at least in part on the plurality of body landmark positions.

Another example aspects of the present disclosure is directed to an improved method for facilitating a Parkinson's Disease ("PD") assessment of a patient including instructing, by a mobile device, a patient to perform first test movements including touchscreen interactions while holding the mobile device, instructing the patient to perform second test movements while maintaining the mobile device on their person; capturing audio of the patient using the microphone of the mobile device; capturing one or more IMU readings using an IMU of the mobile device; processing the IMU readings, the touchscreen interactions, and the captured audio to generate an assessment score based on a standardized PD assessment; and outputting the standardized assessment. The improved method further includes capturing first and second video, respectively, using a front-facing camera of the mobile device, of a face and a hand of the patient while performing the above first test movements and second test movements, respectively; capturing third video of third test movements, and processing the first video, the second video, and the third video to generate one or more tracking assessments.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which:

FIG. 5 depicts a block diagram of an example system for movement disorder diagnostics according to example embodiments of the present disclosure.

FIGS. 20A-20B depict example palm detections within image frames using a palm detection model according to example embodiments of the present disclosure.

FIG. 37 depicts example body landmark positions according to example embodiments of the present disclosure.

Figure 1:
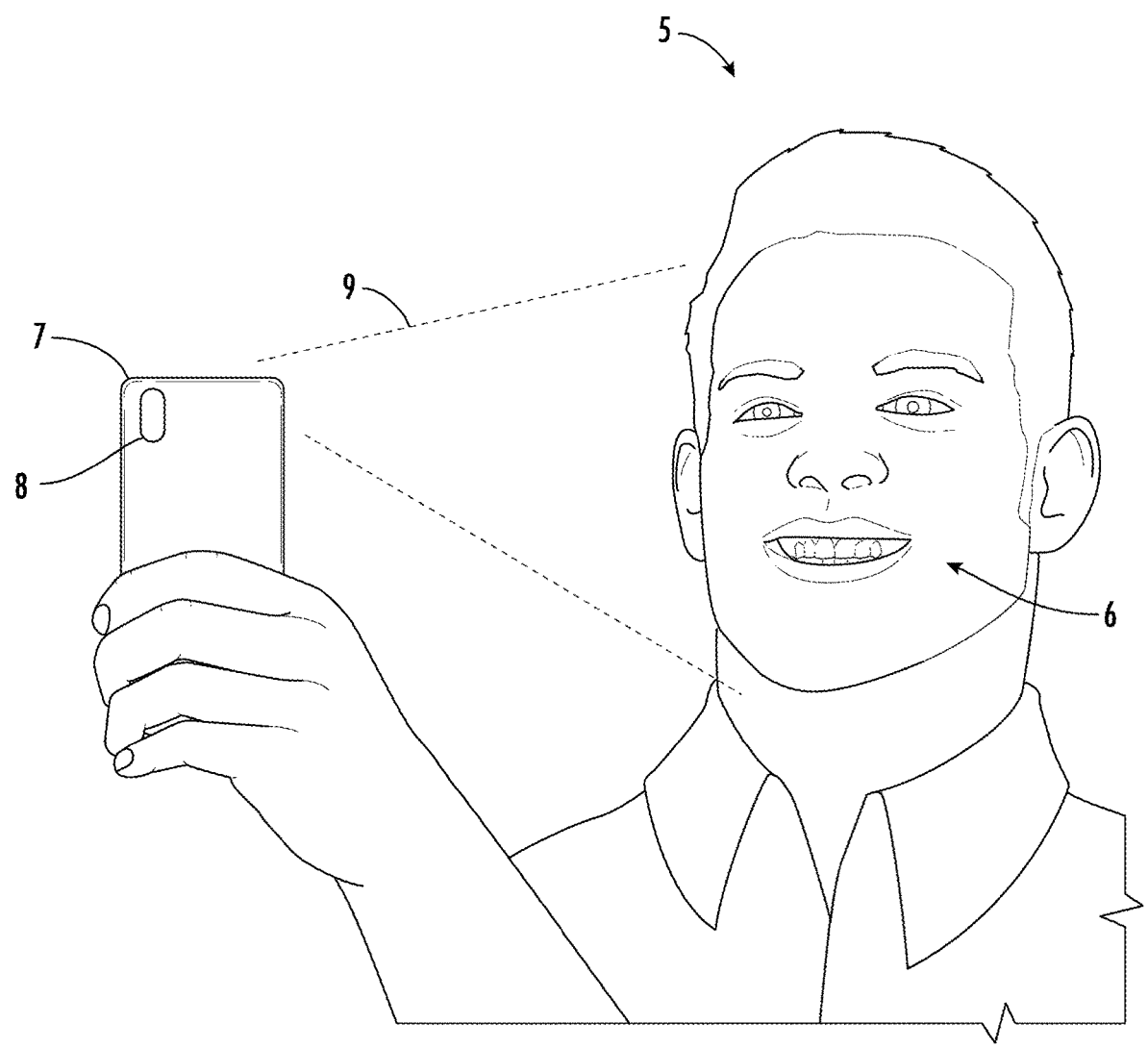
FIG. 1 depicts a patient capturing video data of facial expressions using a camera of a mobile device according to example embodiments of the present disclosure.

Reference numerals that are repeated across plural figures are intended to identify the same features in various implementations.

DETAILED DESCRIPTION

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Generally, the present disclosure is directed to systems and methods for movement disorder diagnostics from video data using body landmark tracking. In particular, systems and methods according to example aspects of the present disclosure can provide diagnosis of movement disorder conditions using consumer-level devices such as smartphones, stationary cameras, or other suitable readily-available devices. According to example aspects of the present disclosure, a computing system can obtain video data. The computing system can, through the use of a body landmark model, identify body landmark positions within the video data. For instance, in some implementations, the body landmark positions can describe a skeletal outline of at least a portion of a user's body, such as a user's hand, face, etc., over time. Furthermore, in some implementations, the body landmark positions can be used to identify one or more biomarkers. The biomarkers can depict aspects of the user's body over time, such as, for example, distance(s) between landmark positions over time, relative movement of the body landmark positions, gestures performed by the user, or other suitable biomarkers. The computing system can, such as through use of a diagnosis model (e.g., a logistical regression model, a random forest model, a neural network, etc.), determine a movement health condition of the user based at least in part on the biomarkers and/or the body landmark positions. For instance, the biomarkers (and/or the body landmark positions) can be provided as input features to the diagnosis model to predict a movement health condition, such as a diagnostic score (e.g., a UPDRS score) for a test based on the biomarkers.

Some existing technologies for in-home assessment of motor symptoms can rely on expensive and/or custom-built hardware, significantly limiting their feasibility. Furthermore, some existing mobile symptom measurement applications are unable to measure a significant breadth of symptoms. Systems and methods according to example aspects of the present disclosure, however, can provide for the use of perception models such as body landmark models, biomarker identification models, diagnosis models, etc., that can quantify many symptoms that are known to be associated with movement disorders such as Parkinson's Disease without necessitating the use of expensive or custom-built hardware. Instead, for example, systems and methods described herein can be implemented using devices that are readily available to many users, such as mobile phones. In addition, systems and methods according to example aspects of the present disclosure can be useful in discovering previously unknown symptoms of movement disorders through data analysis and machine-learning.

Recent improved ability to build and deploy perception models to mobile phones and/or advancements in special processing units to run these models (e.g., GPU/TPU) has allowed perception models to run at sufficient speeds to quantify many of the symptoms measured by the UPDRS rating system for Parkinson's Disease. For instance, some example implementations utilize 1) a hand tracking model (e.g., with individual finger and joint segmentation), 2) a face tracking model (e.g., with >70 keypoints tracked), and/or 3) the embedded IMU in the phone to quantify several of the UPDRS tests.

For instance, in some example implementations, systems and methods according to example aspects of the present disclosure can quantify clinical tests, such as Unified Parkinson's Disease Rating Scale (UPDRS) tests, using one or more perception models (e.g., hand perception models, face perception models, etc.) and/or other data from an inertial motion unit (IMU) and/or other sensors of a user device such as a smartphone, wearable device, etc. For instance, example tests can include speech tests (e.g., using a microphone), facial expression tests (e.g., using a facial perception model, such as an expression recognition model), finger tapping (e.g., using a hand perception model), hand movements and/or gestures (e.g., using a hand perception model), pronation and/or supination of hands (e.g., using a hand perception model), arising from chair (e.g., using an accelerometer, body perception model, etc.), and/or walking/gait tests (e.g., from a body perception model, inertial motion unit, etc.), among other tests. As one example, in some implementations, systems and methods according to example aspects of the present disclosure can utilize one or more of a hand perception model (e.g., using a smartphone and/or other camera), a face perception model (e.g., using a smartphone and/or other camera) and/or a motion perception model (e.g., using an inertial motion unit of a user device) to quantify tests for a movement disorder, such as UPDRS tests for Parkinson's Disease.

For instance, one example aspect of the present disclosure is directed to a computing system for generating movement disorder diagnostics. The computing system can include one or more processors. Additionally and/or alternatively, the computing system can include one or more non-transitory computer-readable media. The non-transitory computer-readable media can collectively store a machine-learned body landmark model configured to obtain video data and identify a plurality of body landmark positions within the video data. Additionally and/or alternatively, the non-transitory computer-readable media can collectively store a machine-learned biomarker model configured to determine one or more biomarkers based at least in part on the plurality of body landmark positions. Additionally and/or alternatively, the non-transitory computer-readable media can collectively store a machine-learned movement health diagnostic model configured to predict a movement health condition based at least in part on the one or more biomarkers. Additionally and/or alternatively, the non-transitory computer-readable media can collectively store instructions, that, when implemented, cause the one or more processors to perform operations for generating movement disorder diagnostics. As an example, the operations can include obtaining the video data, where the video data includes one or more frames; providing the video data as input to the machine-learned body landmark model; receiving, as an output from the machine-learned body landmark model, data descriptive of the plurality of body landmark positions within the video data; providing the data descriptive of the plurality of body landmark positions as input to the machine-learned biomarker model; receiving, as an output from the machine-learned biomarker model, data descriptive of the one or more biomarkers; providing the data descriptive of the one or more biomarkers to the machine-learned movement health diagnostic model; and/or receiving, as an output from the machine-learned movement health diagnostic model, data descriptive of a movement health condition. In some implementations, the movement health diagnostic model can be at least one of a logistical regression model, a random forest model, or a neural network.

In some implementations, the data descriptive of a movement health condition can include a diagnostic score. The diagnostic score can be descriptive of a performance on a clinical movement health diagnostic test. In some implementations, the diagnostic score can be or can include a movement disorder severity score. For instance, in some implementations, the diagnostic score can include a numerical value (e.g., from 0 to 4) descriptive of a severity of a patient's movement health condition. The clinical movement health diagnostic test can be or can include any suitable test. For instance, in some implementations, the clinical movement health diagnostic test can be or can include at least one of a speech test, a facial expression test, a finger tapping test, a hand movement test, a hand pronation test, a hand supination test, a hand gesture test, a walking or gait analysis test, and/or a chair arising test.

In some implementations, the machine-learned body landmark model can be or can include a skeletal position model. In some implementations, the plurality of body landmark positions can include positions on a hand. For instance, the plurality of body landmark positions can be indicative of a skeletal model of a user's hand. The skeletal model can include coordinates (e.g., three-dimensional coordinates) of hand positions (e.g., joints, bones, outlines, etc.). The skeletal position model can be indicative of a skeletal model of other portions of a user's body, such as the user's whole body, the user's face, or other suitable portions. Furthermore, in some implementations, the plurality of body landmark positions can include a time series of coordinates on a body. For instance, the coordinates can describe movement of the body landmark positions (e.g., in three-dimensional space) over time. Furthermore, in some implementations, the plurality of body landmark positions can include positions on a face.

In some implementations, the one or more biomarkers can include distance between an index finger and a thumb over time. For instance, the distance between the index finger and the thumb over time can be represented as a one-dimensional time series representative of the distance between the tips of the thumb and index finger. The amplitude of the time series can represent the amplitude of the proximity of fingertips of the thumb and index fingers.

In some implementations, the machine-learned biomarker model can include a coordinate normalization model configured to normalize one or more coordinates of the body landmark positions, a principal component analysis model configured to perform principal component analysis on the one or more coordinates of the body landmark positions, and/or a feature extraction model configured to extract one or more features from the one or more coordinates of the body landmark positions. For instance, the coordinates can be normalized by the coordinate normalization model, such as by the summed length of joint components proximate the coordinates to provide for improved understanding of joint mechanics that are invariant to camera perspective, such as depth of hand. Subsequently, the normalized skeletal coordinates can be analyzed by principal component analysis to represent the skeletal coordinates in a format that is suitable for biomarker extraction, such as a time series of amplitudes, distances, etc. The feature extraction model can extract the one or more features (e.g., biomarkers) from the skeletal coordinates.

In some implementations, the biomarker model can be further configured to receive speech data. For instance, in some implementations, speech intelligibility models can be applied to score a speech intelligibility of the speech data. For instance, in some cases, therapeutic implants may be provided to a patient to reduce symptoms of some movement disorders. The therapeutic implants may have an effect on the patient's speech. Furthermore, some movement disorders can contribute to speech impediments. The speech intelligibility can, in some cases, thus be indicative of a severity of some movement disorders.

In some implementations, the video data can be obtained from a stationary camera. For instance, in some implementations, the video data can be obtained from a passive camera that a user configures for monitoring. Additionally and/or alternatively, a user can be prompted (e.g., by a mobile device of the user) to record the user's movements, perform a recorded exercise, or otherwise prompted to provide the video data.

Furthermore, in some implementations, input to the movement health diagnostic model can further include motion data. For instance, the motion data can be or can include data from an inertial motion unit (IMU) and/or other data descriptive of motion of a user device, such as a wearable device, smartphone, etc. In some implementations, the motion data can be merged into a multimodal representation of the video data. For instance, the motion data can be used to correct the plurality of body landmark positions to improve accuracy of the body landmark positions.

Another example aspect of the present disclosure is directed to a computer-implemented method for generating movement disorder diagnostics. The computer-implemented method can include obtaining (e.g., by a computing system including one or more computing devices) video data. The video data can include one or more frames. For instance, in some implementations, the video data can be captured by a camera on a mobile device of the user. As another example, in some implementations, the video data can be captured by a stationary camera.

The method can include determining (e.g., by the computing system) a plurality of body landmark positions based at least in part on the video data. In some implementations, the machine-learned body landmark model can be or can include a skeletal position model. In some implementations, the plurality of body landmark positions can include positions on a hand. For instance, the plurality of body landmark positions can be indicative of a skeletal model of a user's hand. The skeletal model can include coordinates (e.g., three-dimensional coordinates) of hand positions (e.g., joints, bones, outlines, etc.). The skeletal position model can be indicative of a skeletal model of other portions of a user's body, such as the user's whole body, the user's face, or other suitable portions. Furthermore, in some implementations, the plurality of body landmark positions can include a time series of coordinates on a body. For instance, the coordinates can describe movement of the body landmark positions (e.g., in three-dimensional space) over time. Furthermore, in some implementations, the plurality of body landmark positions can include positions on a face.

The method can include determining (e.g., by the computing system) a movement health condition based at least in part on the plurality of body landmark positions. In some implementations, determining the movement health condition can include determining (e.g., by the computing system) one or more biomarkers based at least in part on the plurality of body landmark positions, wherein the movement health condition is based at least in part on the one or more biomarkers.

In some implementations, the data descriptive of a movement health condition can include a diagnostic score. The diagnostic score can be descriptive of a performance on a clinical movement health diagnostic test. In some implementations, the diagnostic score can be or can include a movement disorder severity score. For instance, in some implementations, the diagnostic score can include a numerical value (e.g., from 0 to 4) descriptive of a severity of a patient's movement health condition. The clinical movement health diagnostic test can be or can include any suitable test. For instance, in some implementations, the clinical movement health diagnostic test can be or can include at least one of a speech test, a facial expression test, a finger tapping test, a hand movement test, a hand pronation test, a hand supination test, a hand gesture test, a walking or gait analysis test, and/or a chair arising test.

Furthermore, one example implementation of example aspects of the present disclosure can simulate hand movements of a 3.4-finger-tapping exercise that is outlined in the UPDRS manual for diagnosing Parkinson's Disease. For instance, in some implementations, a machine-learned hand perception model (e.g., a body landmark model configured to operate on a user's hand) can convert raw video and/or image data to a plurality of body landmark positions indicative of a skeletal model of a user's hand. For instance, the body landmark positions can include coordinates (e.g., three-dimensional coordinates) of hand positions (e.g., joints, bones, outlines, etc.). These coordinates over time can be analyzed and used in determining a numerical value indicative of severity of Parkinson's Disease (e.g., from zero to four, as in the UPDRS test).

Another example implementation according to example aspects of the present disclosure can provide a movement disorder diagnosis based at least in part on gait detection. For instance, body perception models can model body landmark positions on a user's body. Biomarkers such as limb swing angle, limb swing frequency, step frequency, step amplitude, step distance, and/or other suitable features can be determined from the body landmark positions. As another example, overall walking speed can be extracted, such as by tracking motion from shoulder landmark positions. The perception models based on body landmark positions can provide accurate results for at least a majority of the user's walking time, especially if the user is not adjusting direction. Overall walking speed, step frequency, and/or other biomarkers can be highly correlated with certain movement health conditions. Thus, the use of systems and methods according to example aspects of the present disclosure, including perception models, speech sensing models, etc., can provide powerful diagnostic tools to understand a user's condition in a clinical setting and/or remote from a clinic.

As another example, systems and methods according to example aspects of the present disclosure can provide for discovery of new features (e.g., new biomarkers) for diagnosis of movement health conditions. For instance, in some implementations, a computing system can obtain a research dataset including video data obtained for the purposes of research into movement health conditions. The video data from the research dataset can be annotated with ground truth information about movement health conditions, such as a ground truth movement health condition severity score. The video data from the research dataset can be input (e.g., by the computing system) into a body landmark model to derive body landmark positions from the video data. The body landmark positions can be used to generate (e.g., by the computing system) one or more hypothesis biomarkers that are hypothesized to be correlated to movement health conditions. The hypothesis biomarker can be tested as a potential indicator of a movement health condition by measuring (e.g., by the computing system) correlation between the biomarker and the ground truth information. For instance, if the presence and/or other feature about a biomarker is highly correlated to a high ground truth movement health condition severity score, or otherwise highly correlated to a movement health condition, clinical analysis of the biomarker may provide a strong indication of the presence of a movement health condition in a patient.

As another example, systems and methods according to example aspects of the present disclosure can provide for an improved method for facilitating a Parkinson's Disease ("PD") assessment of a patient according to a standardized assessment scale using a readily-available computing device. Systems and methods can instruct, (e.g., by a mobile device including a touchscreen, an inertial measurement unit (IMU), and a microphone) a patient to perform first test movements while holding the mobile device in a hand of the patient. For instance, the mobile device can display (e.g., on the touchscreen), read (e.g., by one or more speakers of the mobile device), and/or otherwise provide written and/or spoken instructions to the patient instructing the patient with steps for performing the first test movements. The instructions may be accompanied with tutorial videos, diagrams, examples, or other audio and/or visual aids. The first set of test movements can include touchscreen interactions with the touchscreen. For instance, the first set of test movements can include interactions such as tracing a pattern on the touchscreen, performing touch gestures (e.g., swiping, tapping, etc.), and/or any other suitable touchscreen interactions.

Systems and methods according to example aspects of the present disclosure can additionally and/or alternatively instruct (e.g., by the mobile device) the patient to perform second test movements while maintaining the mobile device on their person. For instance, the mobile device can display (e.g., on the touchscreen), read (e.g., by one or more speakers of the mobile device), and/or otherwise provide written and/or spoken instructions to the patient instructing the patient with steps for performing the second test movements. The instructions may be accompanied with tutorial videos, diagrams, examples, or other audio and/or visual aids. The second test movements can include movements to be performed by the patient. For instance, second test movements can include movements such as arising from a chair, walking, standing, etc.

Systems and methods according to example aspects of the present disclosure can additionally and/or alternatively capture audio of the patient using the microphone of the mobile device during at least one of the first test movements or the second test movements. For instance, the microphone of the mobile device can capture (e.g., while preserving privacy of the patient) audio data such as spoken audio, speech, etc. from the patient. Additionally and/or alternatively, Systems and methods according to example aspects of the present disclosure can capture one or more IMU readings using the IMU of the mobile device during at least one of the first test movements or the second test movements. For instance, the IMU readings can be obtained from the IMU and/or stored in memory of the mobile device.

Systems and methods according to example aspects of the present disclosure can additionally and/or alternatively process the IMU readings, the touchscreen interactions, and the captured audio to generate an assessment score based on a standardized PD assessment. For instance, the systems and methods can score the data obtained by the mobile device according to the standardized assessment to produce the assessment score analogous to a score that would be determined if the patient were to undergo manual assessment by a clinician. However, the assessment score can be determined via objective, data-driven analysis, such that the assessment score is more consistent, repeatable, and/or less subjective. The systems and methods can then output the standardized assessment to the patient or a clinician. For instance, the assessment and/or assessment score can be provided (e.g., displayed) to a patient, clinician, or other medical professional such that the condition of the patient is assessed. The standardized assessment can be any suitable assessment, such as assessments including at least one of a speech test, a facial expression test, a finger tapping test, a hand movement test, a hand pronation test, a hand supination test, a hand gesture test, a walking or gait analysis test, and/or a chair arising test. For instance, in some implementations, the standardized assessment can be a Unified Parkinson Disease Rating Scale (UPDRS) or a similar standardized assessment scale.

According to example aspects of the present disclosure, systems and methods are improved by capturing first and second video, respectively, using a front-facing camera of the mobile device, of a face and a hand of the patient while performing the above first test movements and second test movements, respectively. For instance, the front-facing camera of the mobile device can be positioned on a front surface of the mobile device (e.g., a same surface of the mobile device as containing a screen, buttons, etc.) such that the front-facing camera generally has a field of view directed towards the user during use of the mobile device. According to example aspects of the present disclosure, with consent from the patient, the front-facing camera of the mobile device can be used to capture video of the user during the first test movements and second test movements. Additionally and/or alternatively, the systems and methods can capture third video using the front-facing camera and/or a rear-facing camera of the mobile device. The rear-facing camera can be disposed on a surface opposing the front-facing camera. During the third test movements, the mobile device can be placed out of the patient's hand but nearby to the body of the patient while performing third test movements. The third test movements can include standing and walking. For instance, the camera can capture video of substantially all of the patient's body during the third test movements such that gait analysis, posture analysis, etc. can be performed for the third test movements.

Systems and methods according to example aspects of the present disclosure can additionally and/or alternatively process the first video, the second video, and the third video according to (i) a hand landmark model to generate one or more hand biomarkers (e.g., a body landmark model configured to recognize specific hand landmarks, such as finger bones, joints, palms, etc.), (ii) a face landmark model (e.g., a body landmark model configured to recognize facial landmarks and/or biomarkers) to generate one or more face biomarkers, and (iii) a body landmark model to generate one or more body biomarkers. The hand biomarkers, face biomarkers, and body biomarkers can be processed in conjunction with said IMU readings, touchscreen readings, and/or captured audio to generate the standardized assessment. At least one of the hand landmark model, the face landmark model, or the body landmark model can be configured to: identify a plurality of body landmark positions in the first video, the second video, or the third video; normalize one or more coordinates of the plurality of body landmark positions; perform principal component analysis on the one or more coordinates of the plurality of body landmark positions; and extract one or more features from the one or more coordinates of the plurality of body landmark positions.

In some implementations, each of said hand landmark model, said face landmark model, and said body landmark model are configured such that they can collectively be stored entirely on the mobile device and can perform said processing of said first, second, and third captured video entirely on the smartphone without requiring offloading to any processor external to the mobile device. For instance, in some implementations, none of said first, second or third video is transferred off of the mobile device at any time. Additionally and/or alternatively, said PD assessment is facilitated without any potential compromise to user privacy. For instance, any personal identifiable information that may be available in any data used for systems and methods herein can be scrubbed, treated, or otherwise obfuscated such that the patient may not be identified from the data.

Systems and methods according to example aspects of the present disclosure can provide for a number of technical effects and benefits. As one example, systems and methods according to example aspects of the present disclosure can provide for objective diagnoses of movement health conditions, such as movement disorders. As another example, systems and methods according to example aspects of the present disclosure can be useful in discovering new features and biomarkers indicative of certain movement health conditions.

With reference now to the Figures, example embodiments of the present disclosure will be discussed in further detail.

FIG. 1 depicts a patient 5 capturing video data of facial expressions using a camera of a mobile device 7 according to example embodiments of the present disclosure. For instance, the patient 5 may be instructed to use the mobile device 7 to capture video data of the patient's facial expressions through one or more prompts or other instructions provided via the mobile device 7. The mobile device 7 can include one or more cameras, such as a rear facing camera 8 and/or a front-facing camera (not illustrated) having a field of view 9. The patient 5 can position the mobile device 7 such that the field of view 9 is in view of the face 6 of the patient. For instance, as illustrated in FIG. 1, in some cases, the patient 5 can hold the mobile device 7. Additionally and/or alternatively, in some implementations, the mobile device may be placed on a surface. The patient 5 can then interact with the mobile device 7 to capture video of the patient's face 6.

Figure 2A:
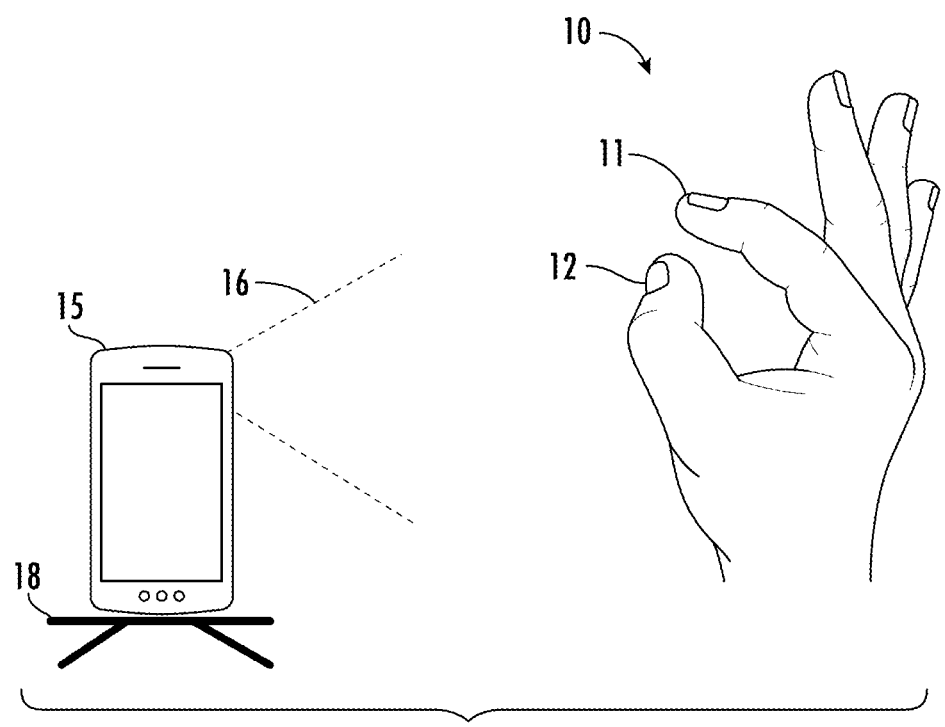
FIGS. 2A and 2B depict capturing video of a hand performing a finger tapping gesture according to example embodiments of the present disclosure.
Figure 2B:
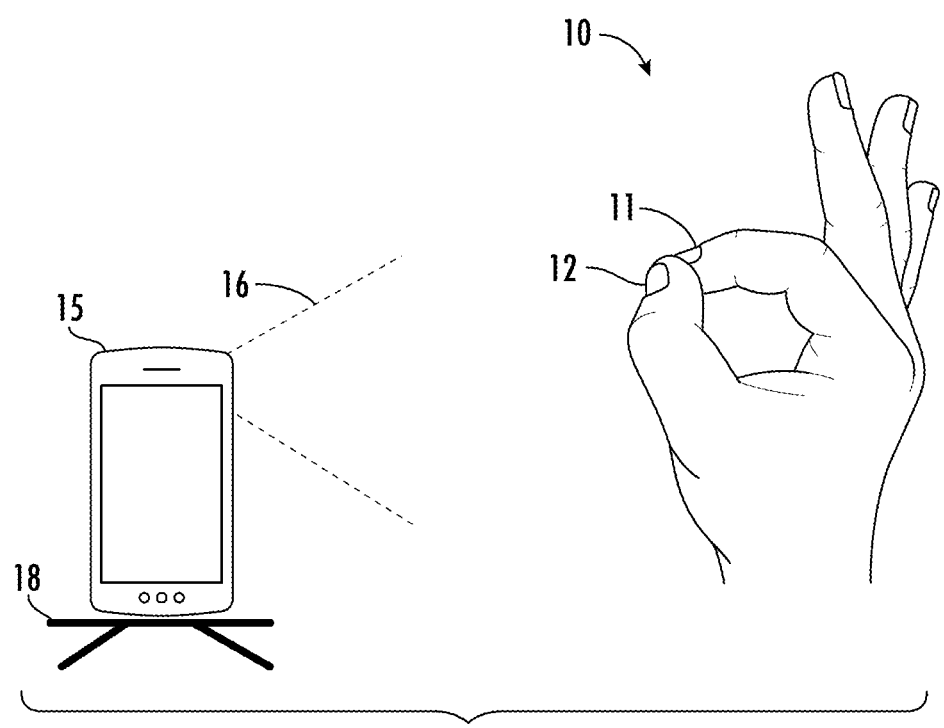

FIGS. 2A and 2B depict capturing video of a hand 10 performing a finger tapping gesture according to example embodiments of the present disclosure. For instance, the video can be captured by mobile device 15. The mobile device 15 can include at least one camera having a field of view 16. The mobile device 15 can be placed on a surface 18 such that the hand 10 is within the field of view 16 of the mobile device 15. The patient can be instructed to tap his or her index finger 11 on his or her thumb 12 in view of the mobile device 15. The distance between the index finger 11 and thumb 12 over time can be captured and analyzed as described herein as a biomarker. The biomarker can be indicative of movement health conditions such as Parkinson's Disease.

Figure 3:
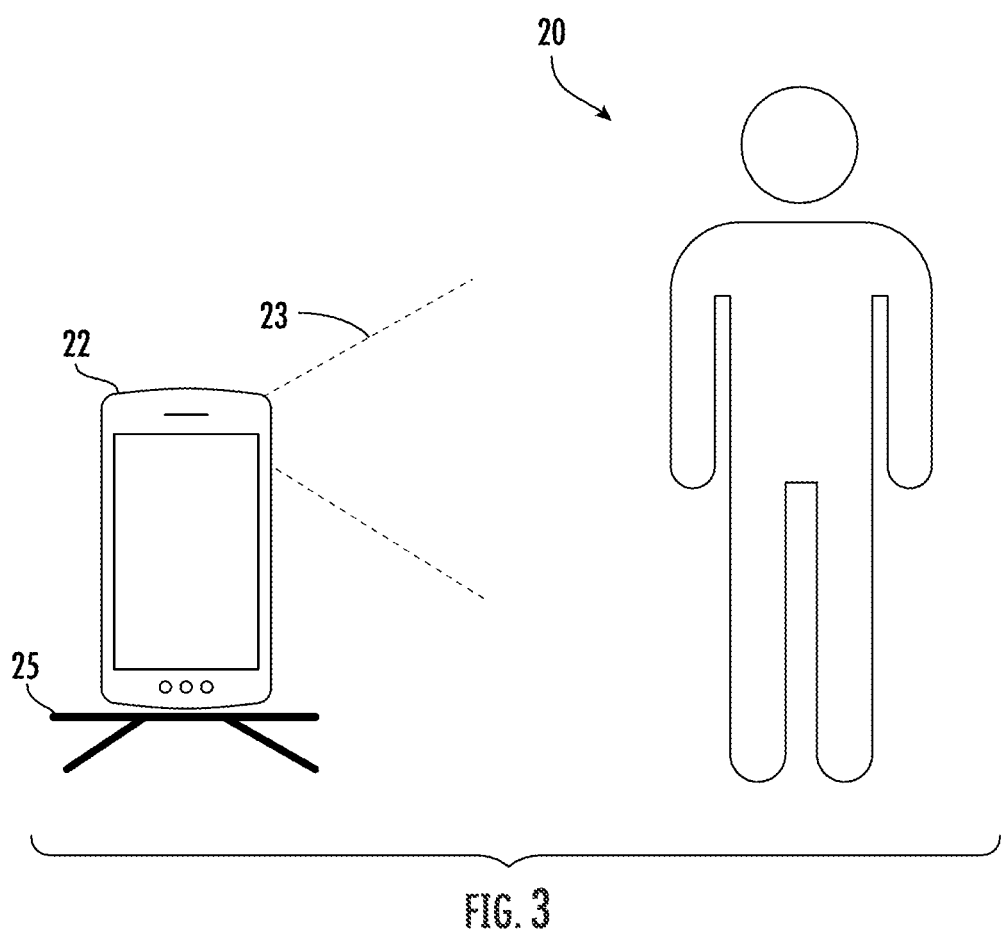
FIG. 3 depicts capturing video of a patient performing a test motion according to example embodiments of the present disclosure.

FIG. 3 depicts capturing video of a patient 20 performing a test motion according to example embodiments of the present disclosure. For instance, the video can be captured by mobile device 22. The mobile device 22 can include at least one camera having a field of view 23. The mobile device 22 can be placed on a surface 25 such that the patient 20 (e.g., the patient's body) is within the field of view 23 of the mobile device 22. The patient 20 can then be instructed to perform test movements such as standing, walking, etc.

Figure 4A:
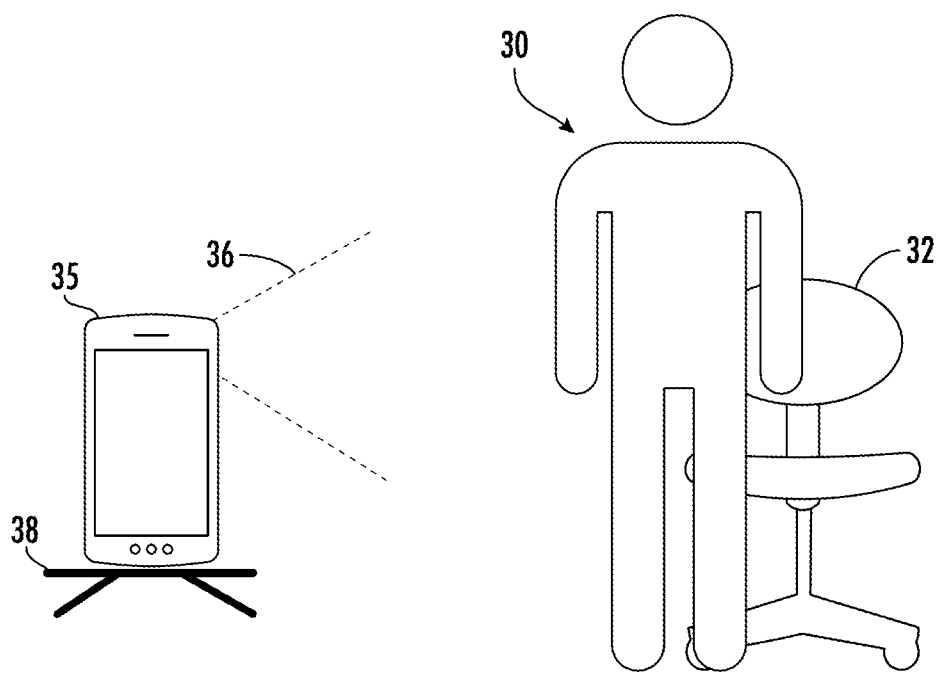
FIGS. 4A and 4B depict capturing video of a patient arising from or sitting in a chair according to example embodiments of the present disclosure.
Figure 4B:
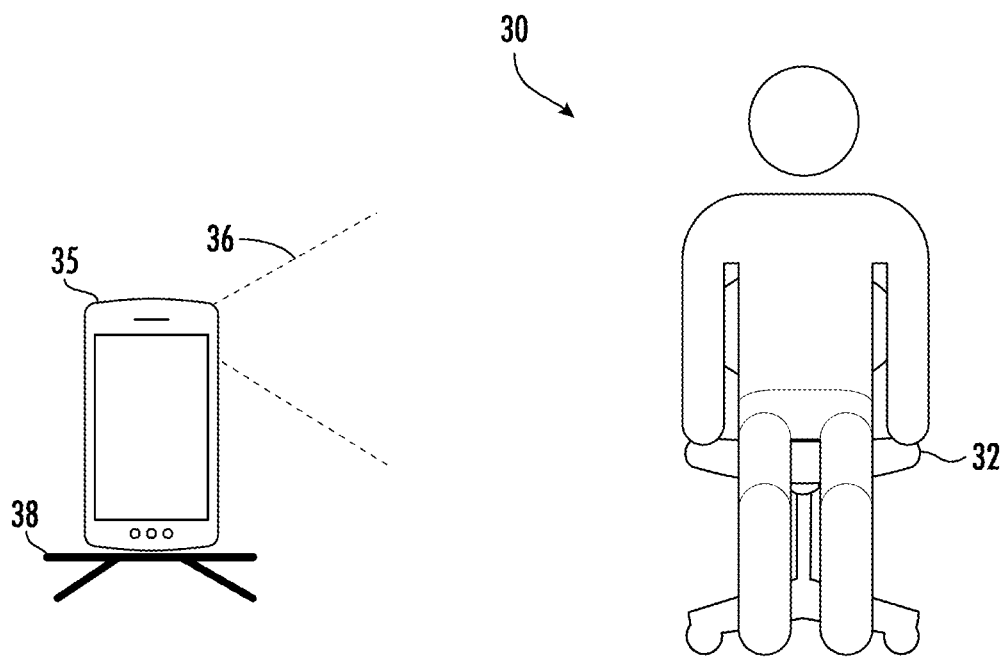

Video data of patient 20 can be captured and analyzed as described herein to diagnose a movement health condition associated with the patient 20. FIG. 4 depicts capturing video of a patient 30 arising from or sitting in a chair 32 according to example embodiments of the present disclosure. For instance, the video can be captured by mobile device 35. The mobile device 35 can include at least one camera having a field of view 36. The mobile device 35 can be placed on a surface 38 such that the patient 30 and/or chair 32 are within the field of view 36 of the mobile device 35. Video data of the patient 30 arising from and/or sitting in chair 32 can be captured and analyzed as described herein to diagnose a movement health condition associated with the patient 30

FIG. 5 depicts a block diagram of an example system 50 for movement disorder diagnostics according to example embodiments of the present disclosure. For instance, body landmark model 52 can receive video data 51 and/or motion data 53. The body landmark model 52 can determine a plurality of body landmark positions based on the video data 51 and/or motion data 53. In some implementations, the machine-learned body landmark model can be or can include a skeletal position model. In some implementations, the plurality of body landmark positions can include positions on a hand. For instance, the plurality of body landmark positions can be indicative of a skeletal model of a user's hand. The skeletal model can include coordinates (e.g., three-dimensional coordinates) of hand positions (e.g., joints, bones, outlines, etc.). The skeletal position model can be indicative of a skeletal model of other portions of a user's body, such as the user's whole body, the user's face, or other suitable portions. Furthermore, in some implementations, the plurality of body landmark positions can include a time series of coordinates on a body. For instance, the coordinates can describe movement of the body landmark positions (e.g., in three-dimensional space) over time. Furthermore, in some implementations, the plurality of body landmark positions can include positions on a face.

The body landmark positions can be provided to biomarker model 54. The biomarker model 54 can determine one or more biomarkers based on the body landmark positions. Biomarkers such as limb swing angle, limb swing frequency, step frequency, step amplitude, step distance, and/or other suitable features can be determined from the body landmark positions. As another example, overall walking speed can be extracted, such as by tracking motion from shoulder landmark positions. The perception models based on body landmark positions can provide accurate results for at least a majority of the user's walking time, especially if the user is not adjusting direction. Overall walking speed, step frequency, and/or other biomarkers can be highly correlated with certain movement health conditions. Thus, the use of systems and methods according to example aspects of the present disclosure, including perception models, speech sensing models, etc., can provide powerful diagnostic tools to understand a user's condition in a clinical setting and/or remote from a clinic.

The one or more biomarkers can be provided to movement health diagnostic model 56. The movement health diagnostic model can output movement health condition 55 based at least in part on the one or more biomarkers. In some implementations, the movement health diagnostic model 56 can be at least one of a logistical regression model, a random forest model, or a neural network. In some implementations, the movement health 55 condition can include a diagnostic score. The diagnostic score can be descriptive of a performance on a clinical movement health diagnostic test. In some implementations, the diagnostic score can be or can include a movement disorder severity score. For instance, in some implementations, the diagnostic score can include a numerical value (e.g., from 0 to 4) descriptive of a severity of a patient's movement health condition. The clinical movement health diagnostic test can be or can include any suitable test. For instance, in some implementations, the clinical movement health diagnostic test can be or can include at least one of a speech test, a facial expression test, a finger tapping test, a hand movement test, a hand pronation test, a hand supination test, a hand gesture test, a walking or gait analysis test, and/or a chair arising test.

Figure 6:
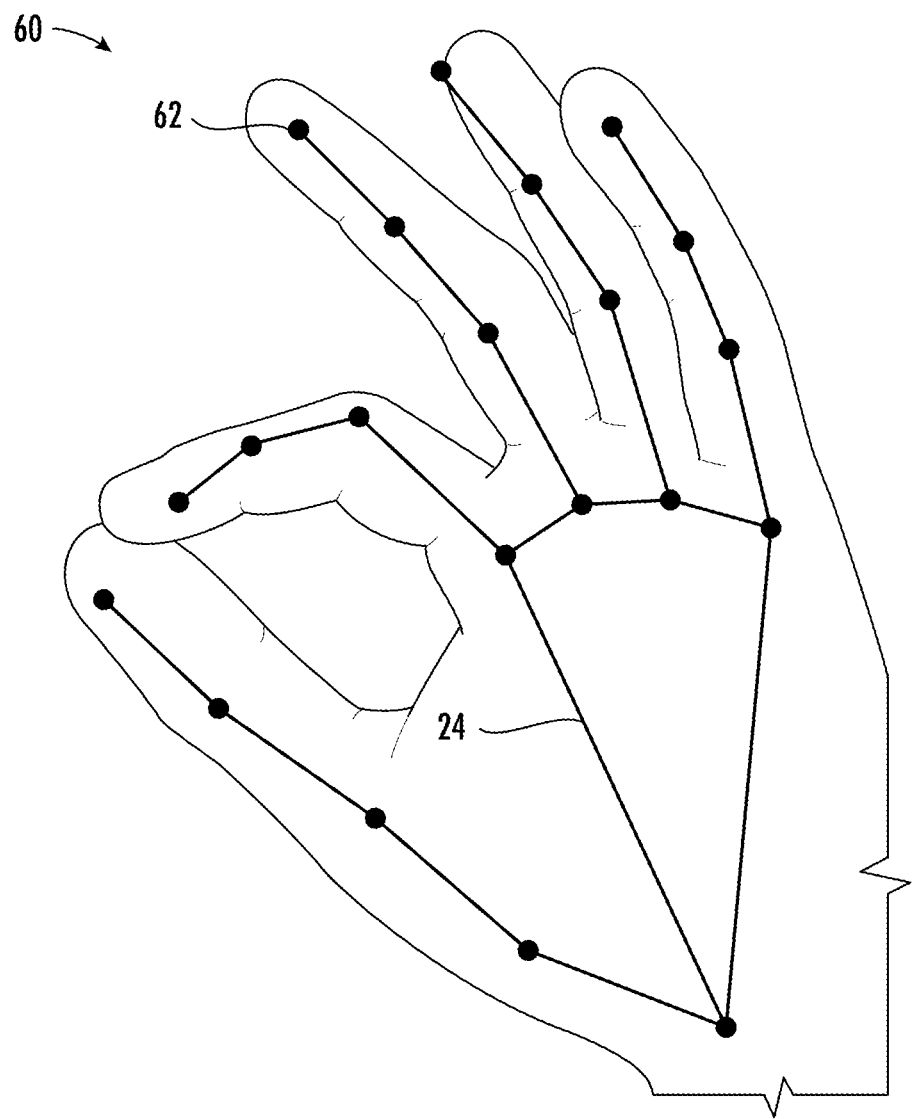
FIG. 6 depicts an example of landmark detections within an image frame illustrating the application of a machine-learned hand landmark model according to example embodiments of the present disclosure.

FIG. 6 depicts an example of landmark detections within an image frame illustrating the application of a machine-learned body landmark model according to example embodiments of the present disclosure. For instance, the image frame can depict hand 60. The hand 60 can be annotated with hand/body landmarks 62 and/or 64. For instance, landmarks 62 may be indicative of joints and/or landmarks 64 may be indicative of bones or other structures of the hand 60.

Figure 7A:
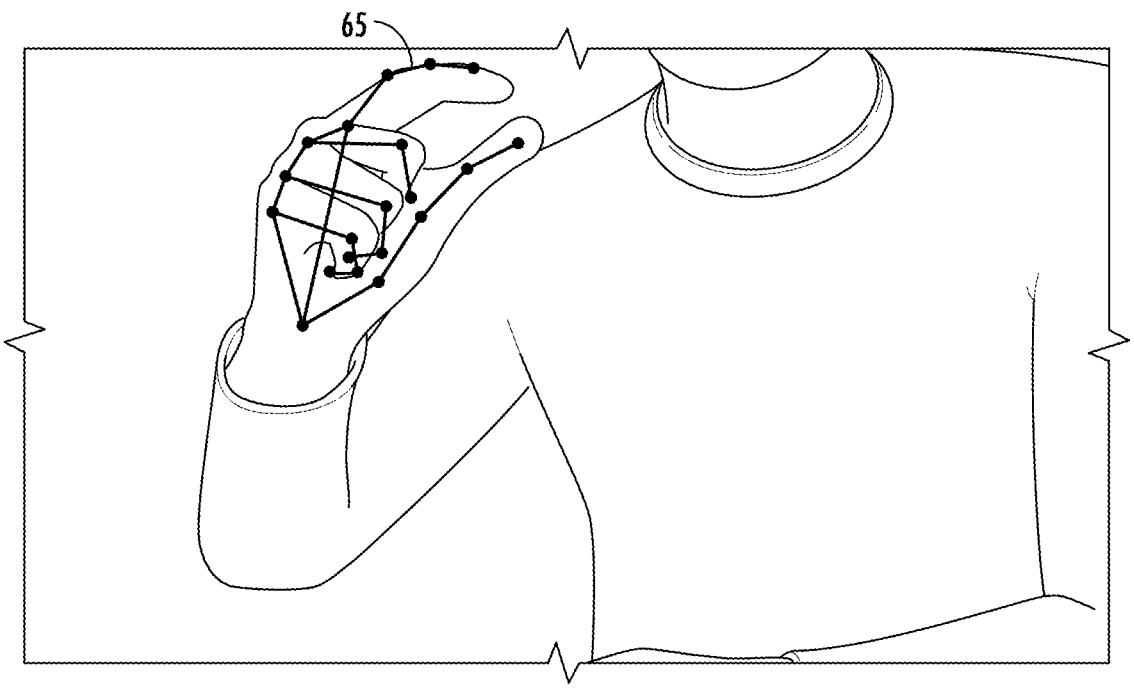
FIGS. 7A and 7B depict example gestures that can be indicative of a movement health condition according to example embodiments of the present disclosure.
Figure 7B:
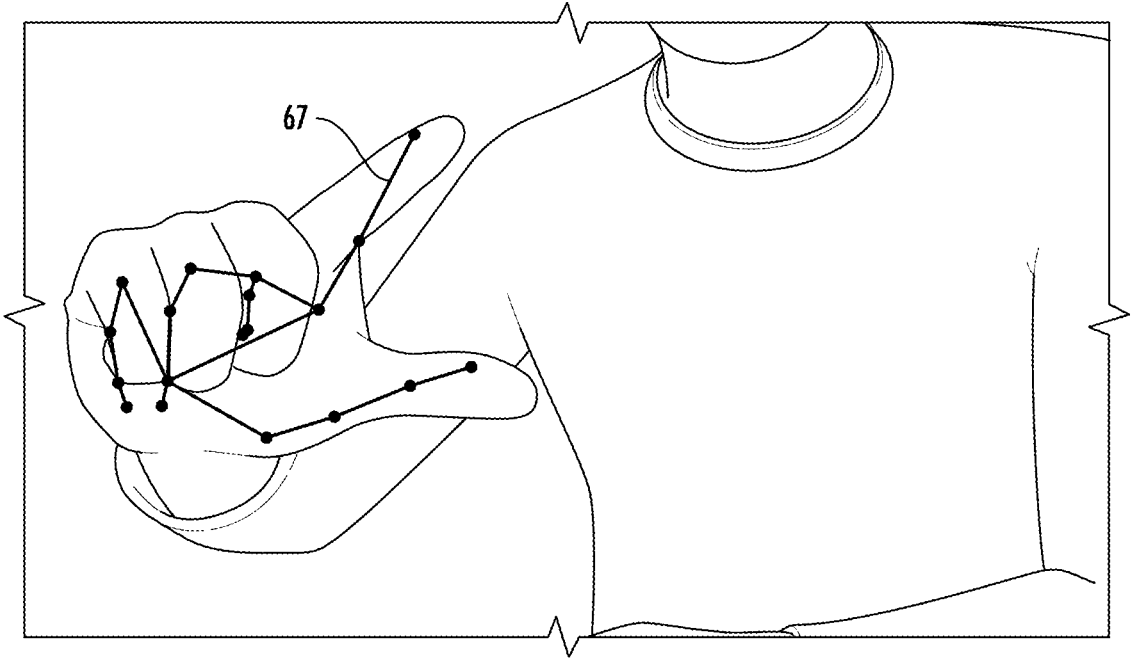

FIGS. 7A and 7B depict example gestures that can be indicative of a movement health condition according to example embodiments of the present disclosure. For instance, FIG. 7A depicts an example of a hand gesture performed by an individual with a first degree of severity of a movement health condition (e.g., an individual not having the movement health condition) and FIG. 7B depicts an example of the hand gesture performed by an individual with a second degree of severity of the movement health condition (e.g., an individual having at least minor severity of the movement health condition).

Figure 8:
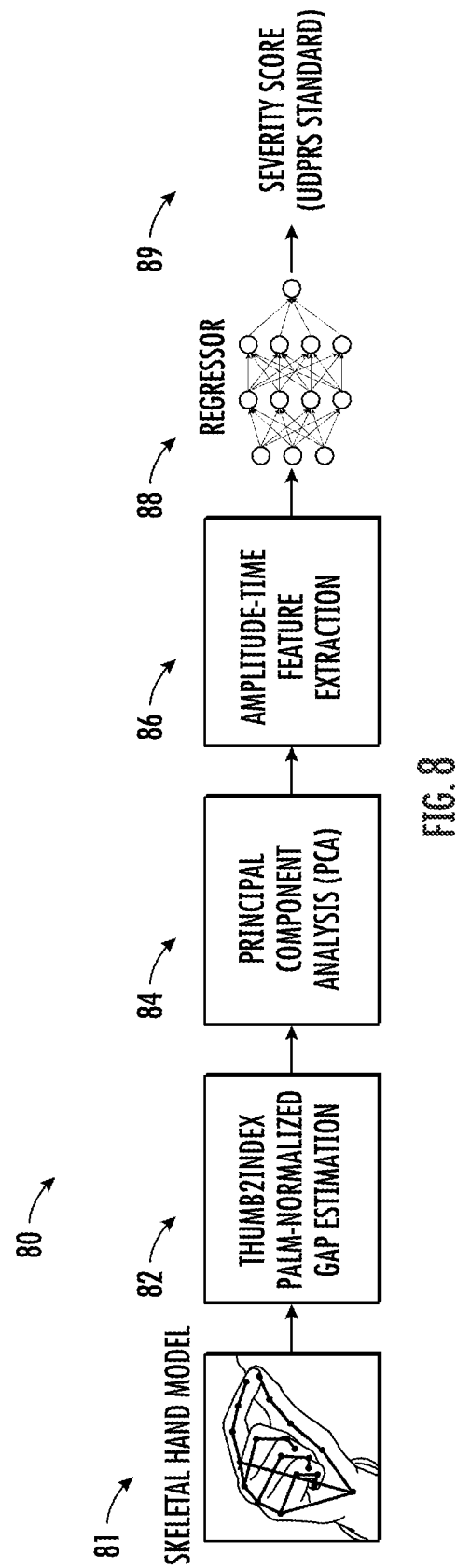
FIG. 8 depicts a block diagram of an example system for diagnosing a movement health condition according to example embodiments of the present disclosure.
Figure 9A:
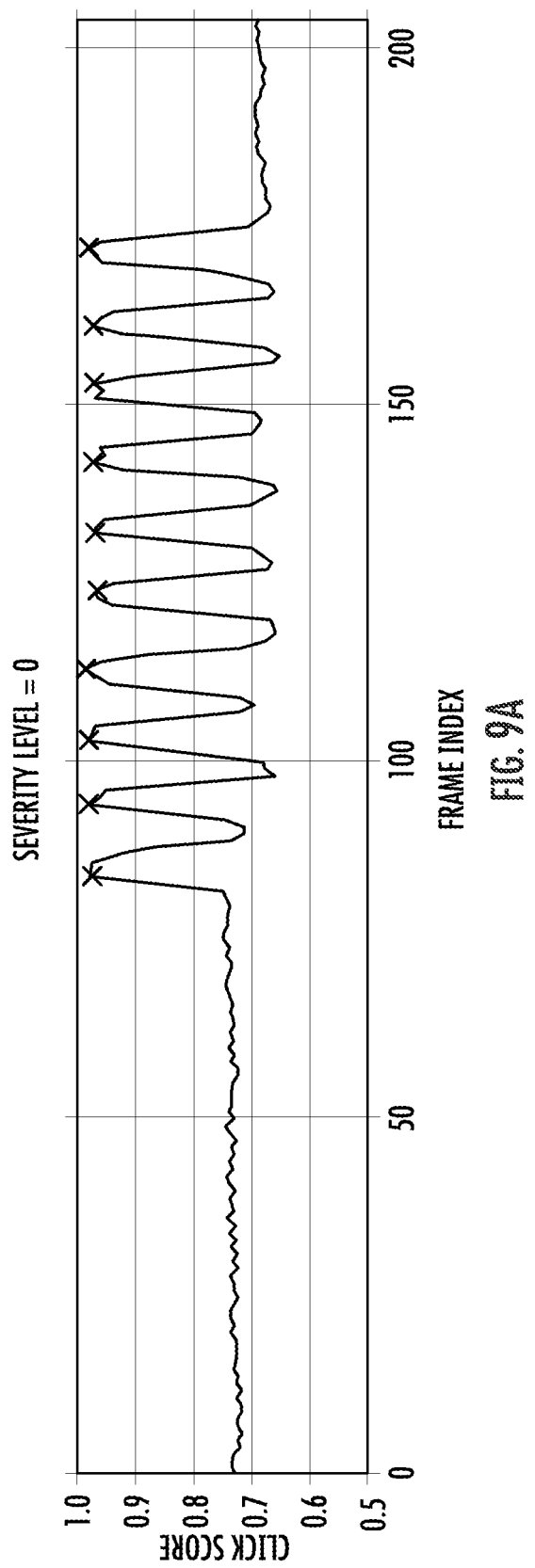
FIGS. 9A and 9B depict an example biomarker according to example embodiments of the present disclosure.
Figure 9B:
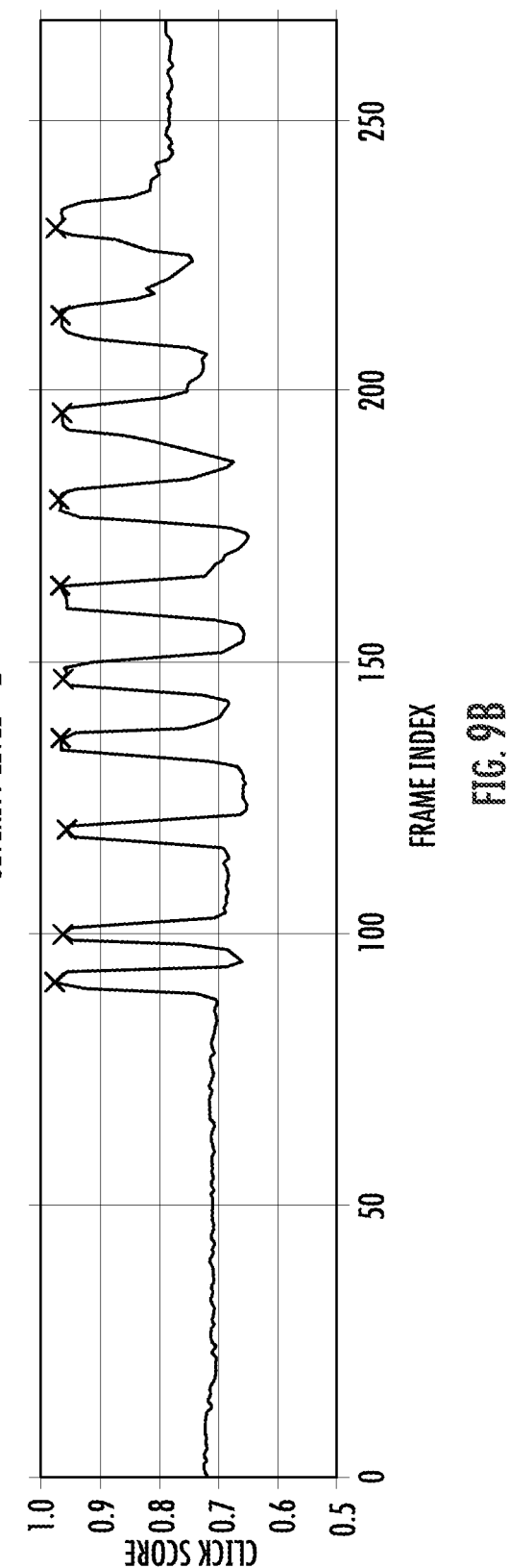

FIG. 8 depicts a block diagram of an example system 80 for diagnosing a movement health condition according to example embodiments of the present disclosure. For instance, in this example implementation, the coordinates of a skeletal hand model 81 (and/or other suitable body landmark positions) can be normalized by thumb-to-index normalization. Skeletal hand model is one example of a body landmark model 52 as shown in FIG. 5. The thumb and index finger coordinates can be normalized by a coordinate normalization model 82. The coordinate normalization model can normalize the thumb and index finger coordinates by the summed length of the thumb and the index finger to provide for improved understanding of joint mechanics that are invariant to camera perspective, such as depth of hand. Subsequently, the normalized skeletal coordinates can be projected to a one-dimensional time series representative of the distance between the tips of the thumb and index finger. The amplitude of the time series can represent the amplitude of the proximity of fingertips of the thumb and index fingers. One example time series is depicted in FIGS. 9A and 9B. For instance, principal component analysis can be performed (e.g., by a principal component analysis model 84) on the vector of coordinates of thumb and index fingers as an approach for projecting the coordinates in an unsupervised manner. Additionally, features of amplitude-time (e.g., as listed in the UPDRS test) can be extracted from the principal component analysis vector (e.g., by a feature extraction model 86). In some implementations, the features can be extracted by heuristics, such as peak detection followed by extracting peak-to-peak variance (e.g., as an amplitude feature) and/or interpeak times (e.g., as a time feature). For instance, the coordinate normalization model 82, principal component analysis model 84, and/or feature extraction model 86 can be or can form at least a portion of a biomarker model 54, as shown in FIG. 5. The extracted features can be used to train a regressor 88 (and/or other diagnostic model). Regressor 88 is one example of a movement health diagnostic model 56 shown in FIG. 5. The regressor/diagnostic model can map from the feature space of the extracted features to an output space, such as a severity score 89 (e.g., a Parkinson's Disease severity score).

FIGS. 9A and 9B depict an example biomarker according to example aspects of the present disclosure. For instance, FIG. 9A depicts an example plot of distance between thumb and index finger over time at a first severity level (e.g., an unafflicted individual). FIG. 9B depicts an example plot of distance between thumb and index finger over time a second severity level (e.g., for a mildly afflicted individual). As can be seen in FIGS. 9A and 9B, the movement health condition can manifest as variances in this distance, thus the distance can be a desirable biomarker for diagnosing the movement health condition.

Figure 10:
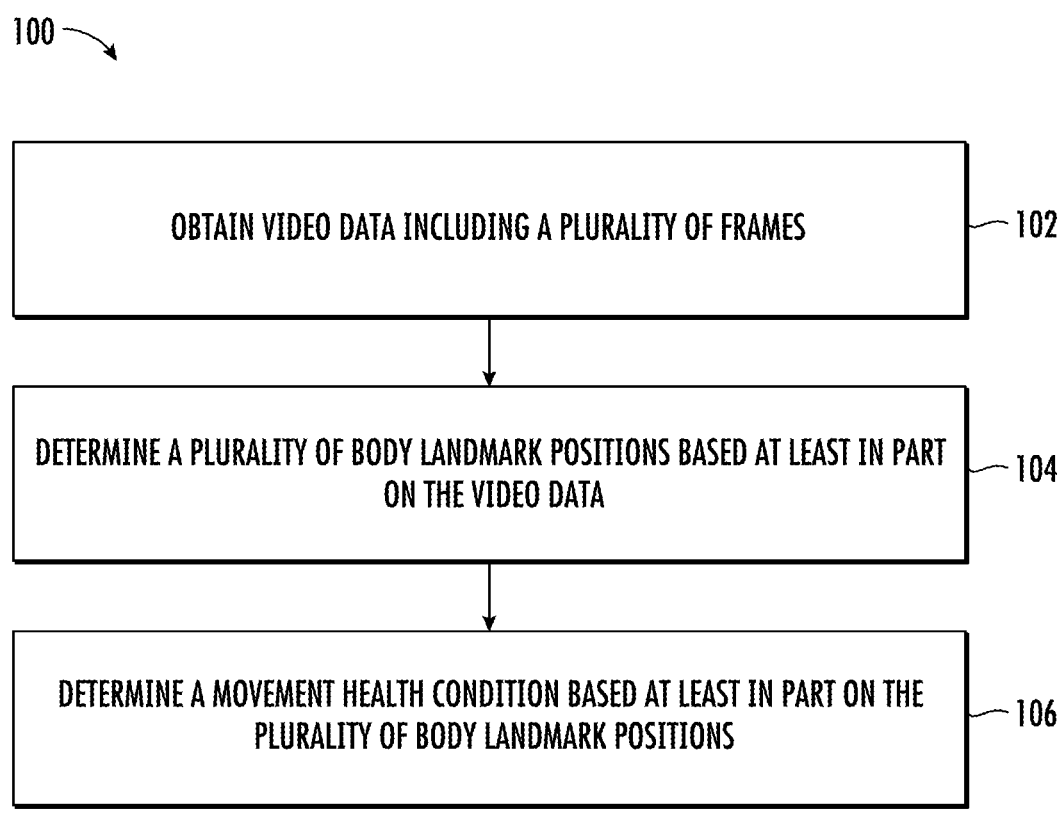
FIG. 10 depicts a flow chart diagram of an example method to perform movement health condition diagnosis according to example embodiments of the present disclosure.

FIG. 10 depicts a flow chart diagram of an example method 100 to perform movement health condition diagnosis according to example embodiments of the present disclosure. Although FIG. 10 depicts steps performed in a particular order for purposes of illustration and discussion, the methods of the present disclosure are not limited to the particularly illustrated order or arrangement. The various steps of the method 100 can be omitted, rearranged, combined, and/or adapted in various ways without deviating from the scope of the present disclosure.

The computer-implemented method 100 can include, at 102, obtaining (e.g., by a computing system including one or more computing devices) video data. The video data can include one or more frames. For instance, in some implementations, the video data can be captured by a camera (e.g., a forward-facing camera and/or a rear-facing camera) on a mobile device of the user. As another example, in some implementations, the video data can be captured by a stationary camera.

The method 100 can include, at 104, determining (e.g., by the computing system) a plurality of body landmark positions based at least in part on the video data. In some implementations, the machine-learned body landmark model can be or can include a skeletal position model. In some implementations, the plurality of body landmark positions can include positions on a hand. For instance, the plurality of body landmark positions can be indicative of a skeletal model of a user's hand. The skeletal model can include coordinates (e.g., three-dimensional coordinates) of hand positions (e.g., joints, bones, outlines, etc.). The skeletal position model can be indicative of a skeletal model of other portions of a user's body, such as the user's whole body, the user's face, or other suitable portions. Furthermore, in some implementations, the plurality of body landmark positions can include a time series of coordinates on a body. For instance, the coordinates can describe movement of the body landmark positions (e.g., in three-dimensional space) over time. Furthermore, in some implementations, the plurality of body landmark positions can include positions on a face.

The method 100 can include, at 106, determining (e.g., by the computing system) a movement health condition based at least in part on the plurality of body landmark positions. In some implementations, determining the movement health condition can include determining (e.g., by the computing system) one or more biomarkers based at least in part on the plurality of body landmark positions, wherein the movement health condition is based at least in part on the one or more biomarkers.

In some implementations, the data descriptive of a movement health condition can include a diagnostic score. The diagnostic score can be descriptive of a performance on a clinical movement health diagnostic test. In some implementations, the diagnostic score can be or can include a movement disorder severity score. For instance, in some implementations, the diagnostic score can include a numerical value (e.g., from 0 to 4) descriptive of a severity of a patient's movement health condition. The clinical movement health diagnostic test can be or can include any suitable test. For instance, in some implementations, the clinical movement health diagnostic test can be or can include at least one of a speech test, a facial expression test, a finger tapping test, a hand movement test, a hand pronation test, a hand supination test, a hand gesture test, a walking or gait analysis test, and/or a chair arising test.

Figure 11:
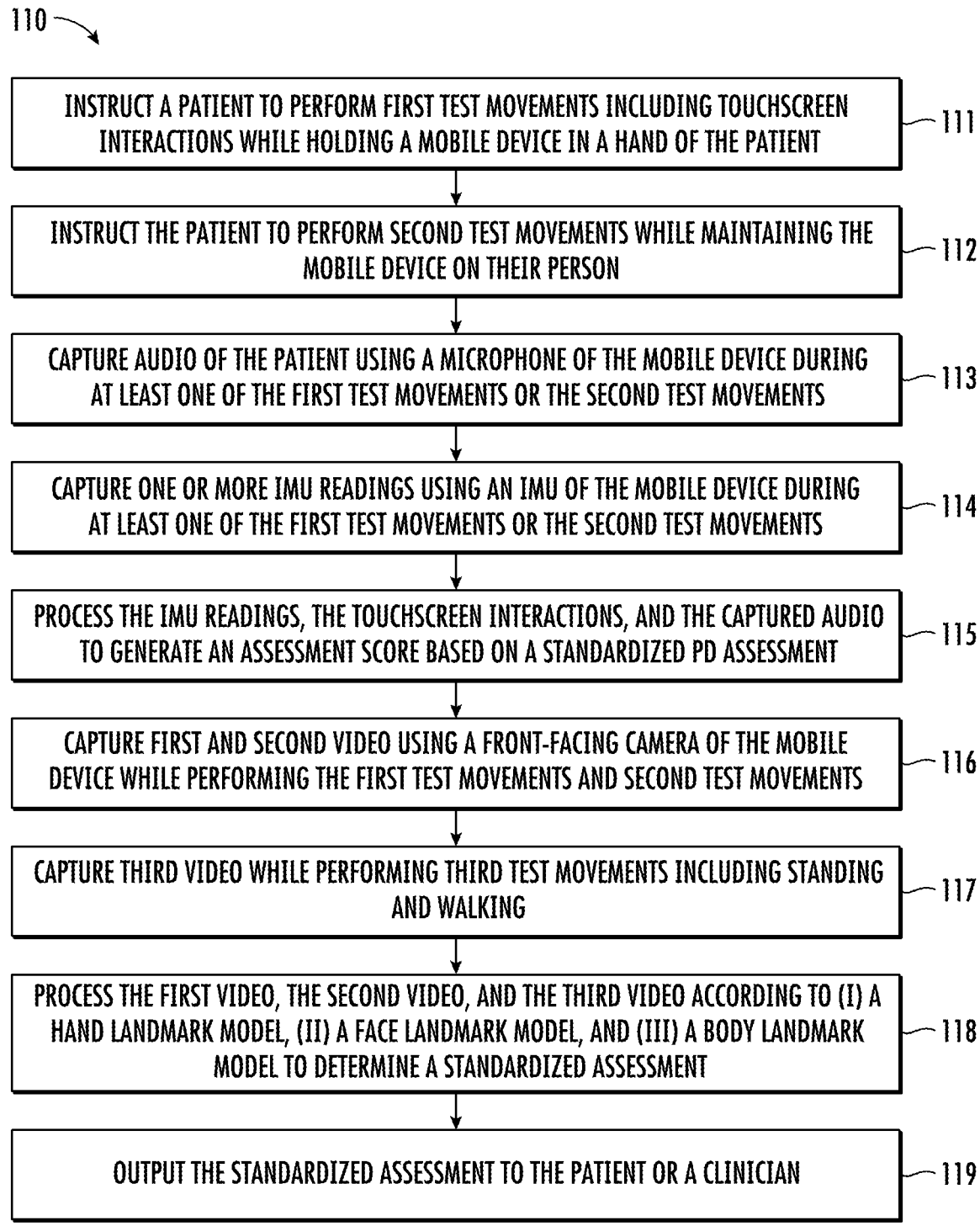
FIG. 11 depicts a flow chart diagram of an example method for performing a standardized Parkinson's Disease assessment of a patient using video data according to example embodiments of the present disclosure.

FIG. 11 depicts a flow chart diagram of an example method 110 for performing a standardized Parkinson's Disease assessment of a patient using video data according to example embodiments of the present disclosure. For instance, systems and methods according to example aspects of the present disclosure can provide for an improved method 110 for facilitating a Parkinson's Disease ("PD") assessment of a patient according to a standardized assessment scale using a readily-available computing device. The method 110 can include, at 111, instructing, (e.g., by a mobile device including a touchscreen, an inertial measurement unit (IMU), and a microphone) a patient to perform first test movements while holding the mobile device in a hand of the patient. For instance, the mobile device can display (e.g., on the touchscreen), read (e.g., by one or more speakers of the mobile device), and/or otherwise provide written and/or spoken instructions to the patient instructing the patient with steps for performing the first test movements. The instructions may be accompanied with tutorial videos, diagrams, examples, or other audio and/or visual aids. The first set of test movements can include touchscreen interactions with the touchscreen. For instance, the first set of test movements can include interactions such as tracing a pattern on the touchscreen, performing touch gestures (e.g., swiping, tapping, etc.), and/or any other suitable touchscreen interactions.

Additionally and/or alternatively, the method 110 can include, at 112, instructing (e.g., by the mobile device) the patient to perform second test movements while maintaining the mobile device on their person. For instance, the mobile device can display (e.g., on the touchscreen), read (e.g., by one or more speakers of the mobile device), and/or otherwise provide written and/or spoken instructions to the patient instructing the patient with steps for performing the second test movements. The instructions may be accompanied with tutorial videos, diagrams, examples, or other audio and/or visual aids. The second test movements can include movements to be performed by the patient. For instance, second test movements can include movements such as arising from a chair, walking, standing, etc.

Additionally and/or alternatively, the method 110 can include, at 113, capturing audio of the patient using the microphone of the mobile device during at least one of the first test movements or the second test movements. For instance, the microphone of the mobile device can capture (e.g., while preserving privacy of the patient) audio data such as spoken audio, speech, etc. from the patient. Additionally and/or alternatively, Systems and methods according to example aspects of the present disclosure can capture one or more IMU readings using the IMU of the mobile device during at least one of the first test movements or the second test movements. For instance, the IMU readings can be obtained from the IMU and/or stored in memory of the mobile device.

Additionally and/or alternatively, the method 110 can include, at 115, processing the IMU readings, the touchscreen interactions, and the captured audio to generate an assessment score based on a standardized PD assessment. For instance, the systems and methods can score the data obtained by the mobile device according to the standardized assessment to produce the assessment score analogous to a score that would be determined if the patient were to undergo manual assessment by a clinician. However, the assessment score can be determined via objective, data-driven analysis, such that the assessment score is more consistent, repeatable, and/or less subjective.

Additionally and/or alternatively, the method 110 can include, at 116, capturing first and second video, respectively, using a front-facing camera of the mobile device, of a face and a hand of the patient while performing the above first test movements and second test movements, respectively. For instance, the front-facing camera of the mobile device can be positioned on a front surface of the mobile device (e.g., a same surface of the mobile device as containing a screen, buttons, etc.) such that the front-facing camera generally has a field of view directed towards the user during use of the mobile device. According to example aspects of the present disclosure, with consent from the patient, the front-facing camera of the mobile device can be used to capture video of the user during the first test movements and second test movements.

Additionally and/or alternatively, the method 110 can include, at 117, capturing third video using the front-facing camera and/or a rear-facing camera of the mobile device. The rear-facing camera can be disposed on a surface opposing the front-facing camera. During the third test movements, the mobile device can be placed out of the patient's hand but nearby to the body of the patient while performing third test movements. The third test movements can include standing and walking. For instance, the camera can capture video of substantially all of the patient's body during the third test movements such that gait analysis, posture analysis, etc. can be performed for the third test movements.

Additionally and/or alternatively, the method 110 can include, at 118, processing the first video, the second video, and the third video according to (i) a hand landmark model to generate one or more hand biomarkers, (ii) a face landmark model to generate one or more face biomarkers, and (iii) a body landmark model to generate one or more body biomarkers. Said hand biomarkers, face biomarkers, and body biomarkers can be processed in conjunction with said IMU readings, touchscreen readings, and captured audio to generate the standardized assessment. At least one of the hand landmark model, the face landmark model, or the body landmark model can be configured to: identify a plurality of body landmark positions in the first video, the second video, or the third video; normalize one or more coordinates of the plurality of body landmark positions; perform principal component analysis on the one or more coordinates of the plurality of body landmark positions; and extract one or more features from the one or more coordinates of the plurality of body landmark positions.

In some implementations, each of said hand landmark model, said face landmark model, and said body landmark model are configured such that they can collectively be stored entirely on the mobile device and can perform said processing of said first, second, and third captured video entirely on the smartphone without requiring offloading to any processor external to the mobile device. For instance, in some implementations, none of said first, second or third video is transferred off of the mobile device at any time. Additionally and/or alternatively, said PD assessment is facilitated without any potential compromise to user privacy. For instance, any personal identifiable information that may be available in any data used for systems and methods herein can be scrubbed, treated, or otherwise obfuscated such that the patient may not be identified from the data.

Additionally and/or alternatively, the method 110 can include, at 119, outputting the standardized assessment to the patient or a clinician. For instance, the assessment and/or assessment score can be provided (e.g., displayed) to a patient, clinician, or other medical professional such that the condition of the patient is assessed. The standardized assessment can be any suitable assessment, such as assessments including at least one of a speech test, a facial expression test, a finger tapping test, a hand movement test, a hand pronation test, a hand supination test, a hand gesture test, a walking or gait analysis test, and/or a chair arising test. For instance, in some implementations, the standardized assessment can be a Unified Parkinson Disease Rating Scale (UPDRS) or a similar standardized assessment scale.

Figure 12:
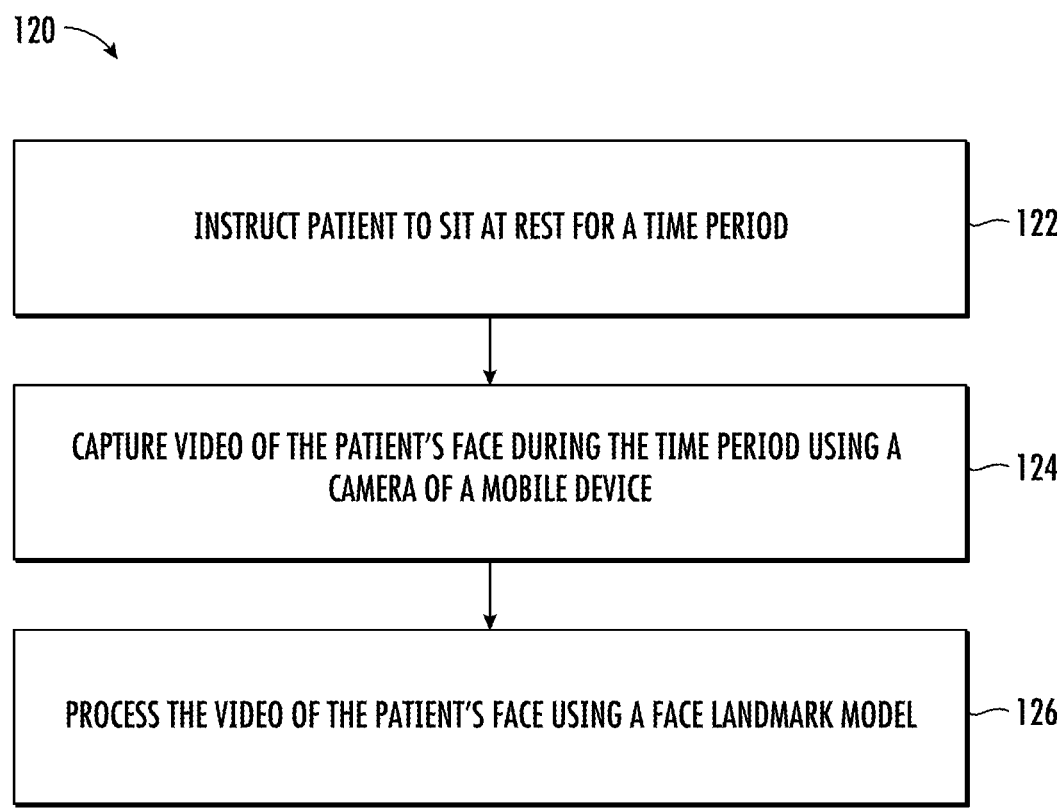
FIG. 12 depicts a flow chart diagram of an example method for processing test movements for a patient performing facial expressions according to example embodiments of the present disclosure.

FIG. 12 depicts a flow chart diagram of an example method 120 for processing test movements for a patient performing facial expressions according to example embodiments of the present disclosure. For instance, the method 120 of FIG. 12 can be used to generate an assessment score for a standardized assessment based on facial expression analysis. At 122, the method 120 includes instructing the patient to sit at rest for a time period. The patient can be instructed in any suitable manner, such as through prompts on a mobile device. The method 120 can then include, at 124, capturing video of the patient's face during the time period using a camera of a mobile device. The patient may talk and/or be silent during the time period. For instance, the video can depict how still or stable the patient's facial expression is at rest. The method 120 can then include, at 126, processing the video of the patient's face using a face landmark model, as described herein. For instance, the video data can be processed to identify one or more biomarkers based on the video data. The biomarkers can then be analyzed to diagnose movement health conditions in the patient.

Figure 13:
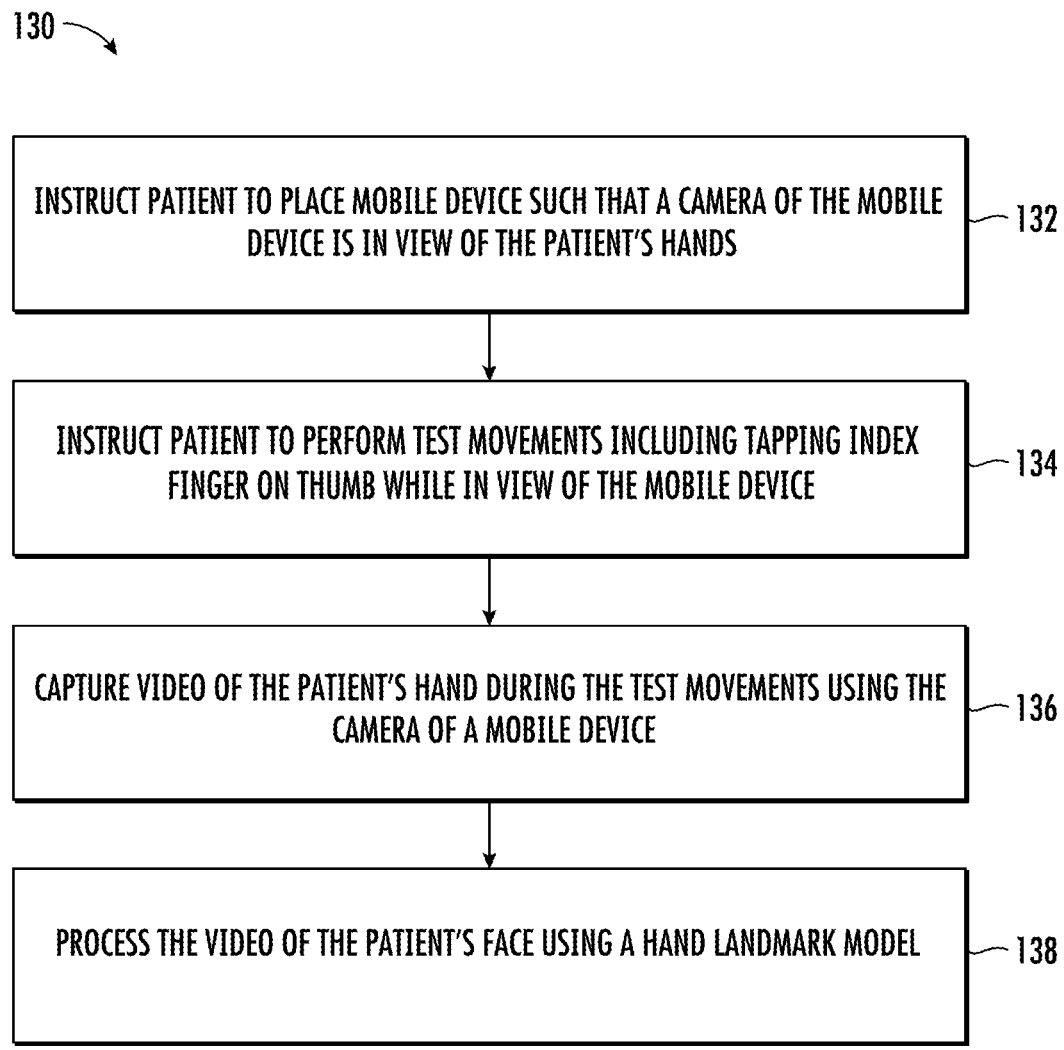
FIG. 13 depicts a flow chart diagram of an example method for processing test movements for a patient performing finger tapping according to example embodiments of the present disclosure.

FIG. 13 depicts a flow chart diagram of an example method 130 for processing test movements for a patient performing finger tapping according to example embodiments of the present disclosure. For instance, the method 130 of FIG. 13 can be used to generate an assessment score for a standardized assessment based on hand gesture analysis, such as finger tapping biomarkers. At 132, the method includes instructing a patient to place a mobile device such that a camera of the mobile device is in view of the patient's hands. The patient can be instructed in any suitable manner, such as through prompts on the mobile device. The method 130 can then include, at 134, instructing the patient to perform test movements including tapping his or her index finger on his or her thumb with the hand of the patient in view of the mobile device (e.g., a camera of the mobile device). The method 130 can then include, at 136, capturing video of the patient's hand during the test movements using the camera of a mobile device. The method 130 can then include, at 138, processing the video of the patient's body using a hand landmark model, as described herein. For instance, the video data can be processed to identify one or more biomarkers based on the video data. The biomarkers can then be analyzed to diagnose movement health conditions in the patient.

Figure 14:
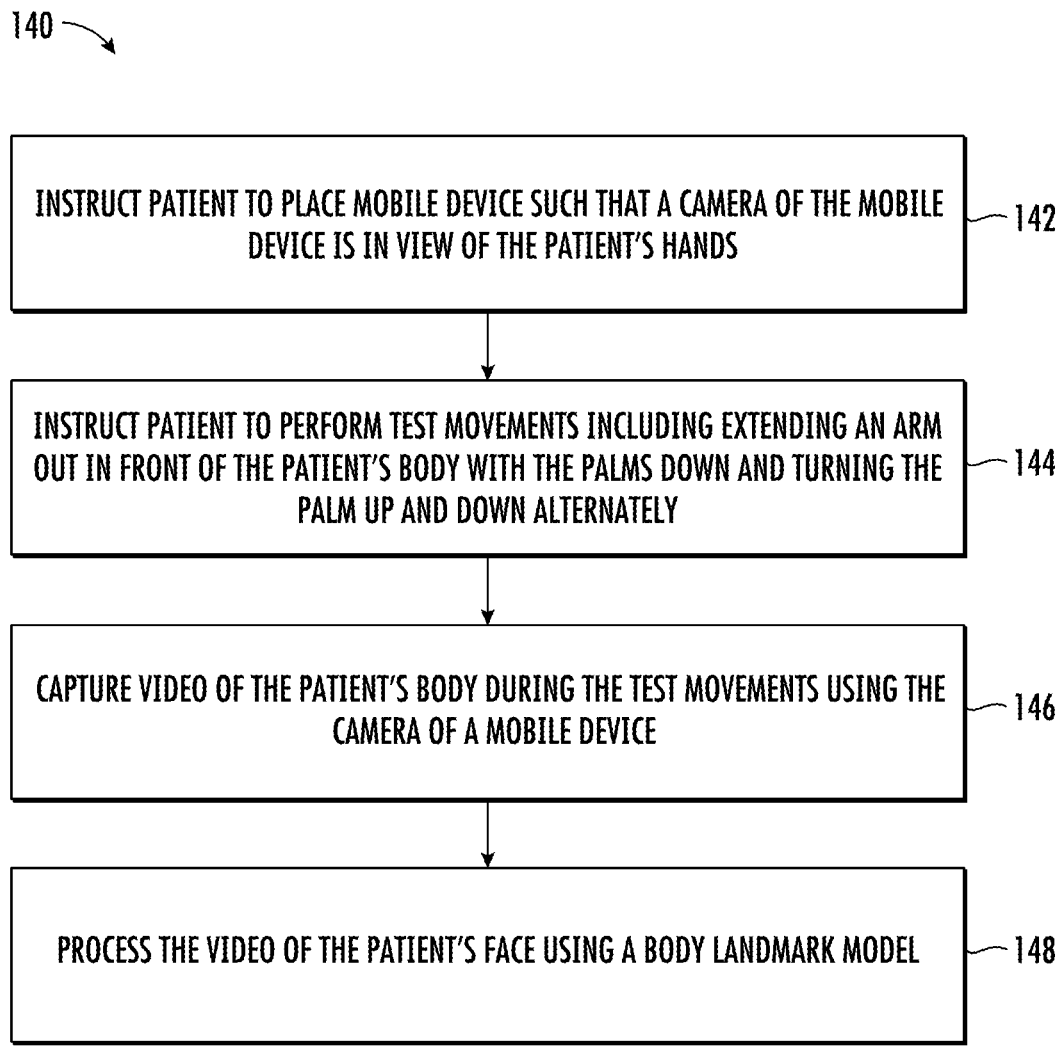
FIG. 14 depicts a flow chart diagram of an example method for processing test movements for a patient performing hand supination according to example embodiments of the present disclosure.

FIG. 14 depicts a flow chart diagram of an example method for processing test movements for a patient performing hand supination according to example embodiments of the present disclosure. For instance, the method 140 of FIG. 14 can be used to generate an assessment score for a standardized assessment based on hand gesture analysis, such as finger tapping biomarkers. At 142, the method includes instructing a patient to place a mobile device such that a camera of the mobile device is in view of the patient's body. The patient can be instructed in any suitable manner, such as through prompts on the mobile device. The method 140 can then include, at 144, instructing the patient to perform test movements for hand supination, including extending an arm out in front of the patient's body with the palms down and turning the palm up and down alternately. The method 140 can then include, at 146, capturing video of the patient's body during the test movements using the camera of a mobile device. The method 140 can then include, at 148, processing the video of the patient's body using a body landmark model, as described herein. For instance, the video data can be processed to identify one or more biomarkers based on the video data. The biomarkers can then be analyzed to diagnose movement health conditions in the patient.

Figure 15:
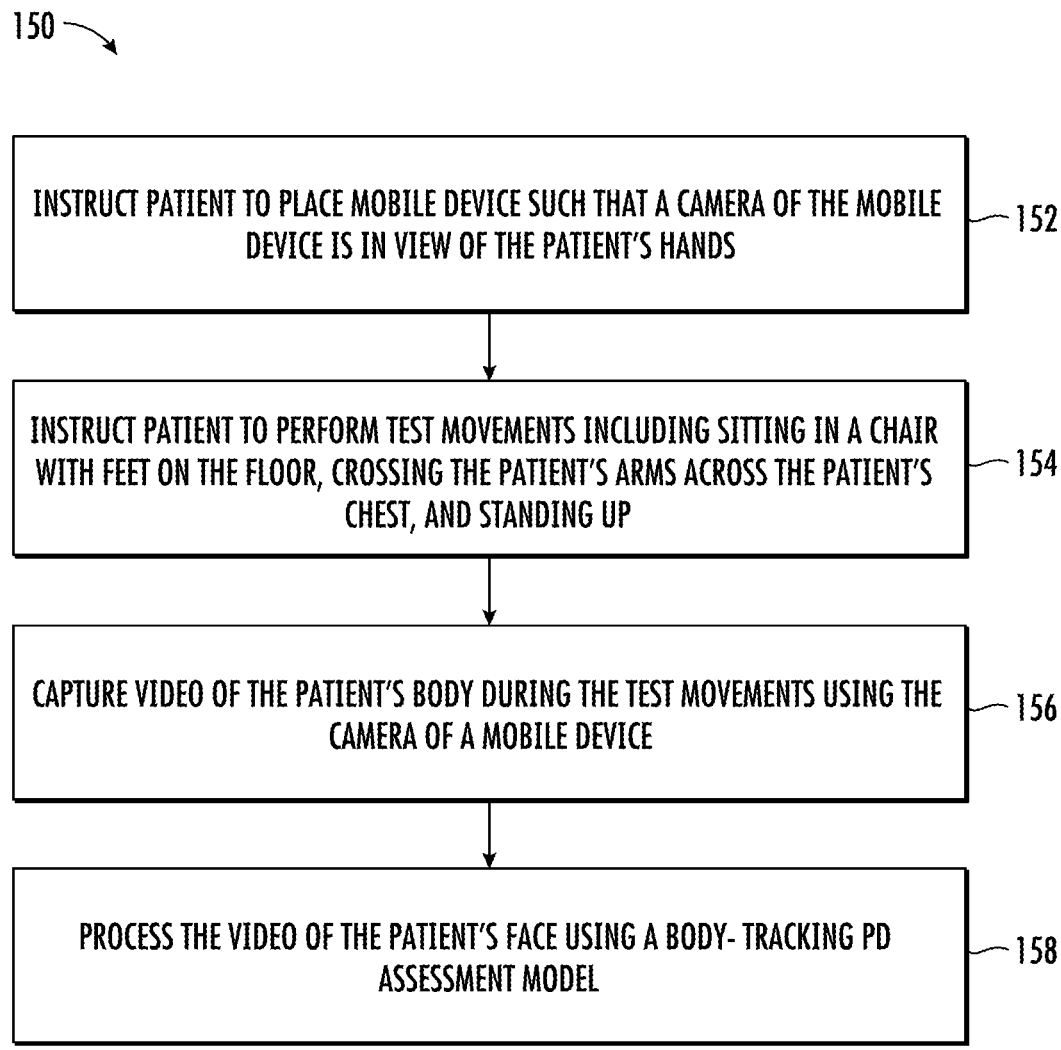
FIG. 15 depicts a flow chart diagram of an example method for processing test movements for a patient arising from a chair according to example embodiments of the present disclosure.

FIG. 15 depicts a flow chart diagram of an example method for processing test movements for a patient arising from a chair according to example embodiments of the present disclosure. For instance, the method 150 of FIG. 15 can be used to generate an assessment score for a standardized assessment based on hand gesture analysis, such as finger tapping biomarkers. At 152, the method includes instructing a patient to place a mobile device such that a camera of the mobile device is in view of the patient's body. The patient can be instructed in any suitable manner, such as through prompts on the mobile device. The method 150 can then include, at 154, instructing the patient to perform test movements for arising from a chair, including sitting in a chair with feet on the floor, crossing the patient's arms across the patient's chest, and standing up. The method 150 can then include, at 156, capturing video of the patient's body during the test movements using the camera of a mobile device. The method 150 can then include, at 158, processing the video of the patient's body using a body landmark model, as described herein. For instance, the video data can be processed to identify one or more biomarkers based on the video data. The biomarkers can then be analyzed to diagnose movement health conditions in the patient.

FIGS. 16 through 36 depict example aspects of body landmark position models according to example aspects of the present disclosure. Some example aspects of FIGS. 16 through 36 are discussed with reference to a hand landmark position model for the purposes of illustration and are not intended to limit the present disclosure to hand landmark positions. It should be understood that various example aspects discussed with reference to hands, palms, etc. can be applied to other potions of a body.

Figure 16:
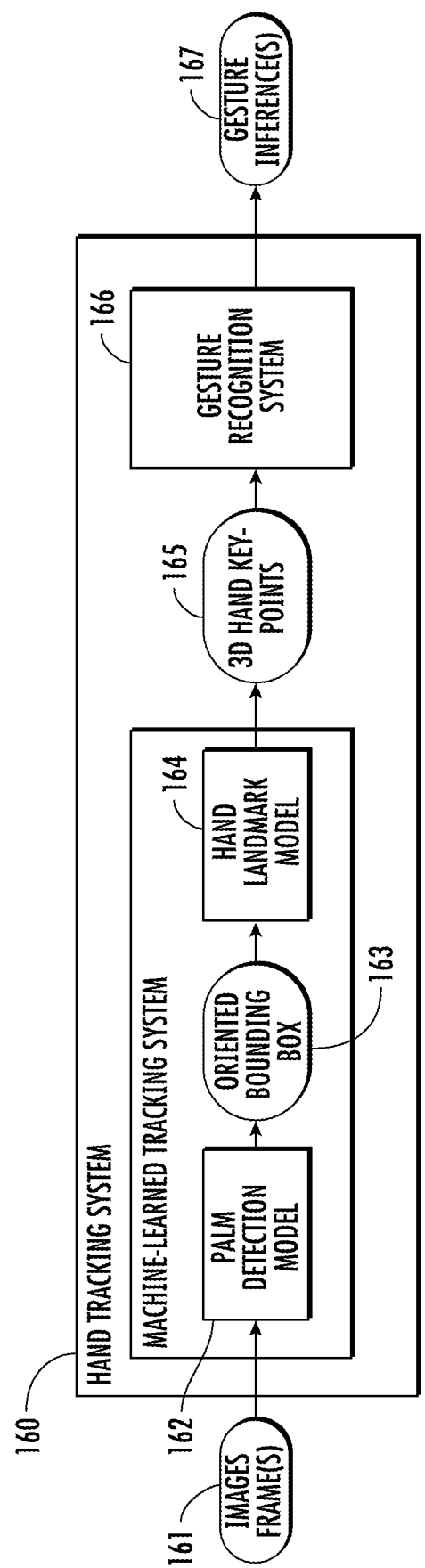
FIG. 16 depicts a block diagram of an example hand tracking system according to example embodiments of the present disclosure.

FIG. 16 depicts a block diagram of an example hand tracking system 160 according to examples embodiments of the present disclosure. The hand tracking system 160 can include both a palm detection model 162 and a hand landmark model 164. In some implementations, both the palm detection model 162 and/or the hand landmark model 164 can be machine-learned models, such as, for example, artificial neural networks such as convolutional networks. For instance, the hand landmark model 164 can be one exemplary body landmark model configured particularly for detection of hand landmarks on a user's hand. It should be understood that other body landmark models (e.g., facial landmark models, etc.) can be used without deviating from the scope of the present disclosure.

The input image frames 161 can include two-dimensional image frames or three-dimensional image frames. For example, the image frames 161 can include images captured by a camera (e.g., visible spectrum camera, infrared camera, hyperspectral camera, etc.) or other image capture system. The images can be expressed in any number of different color spaces (e.g., greyscale, RGB, CMYK, etc.). As another example, the input image frames can include images generated by a Light Detection and Ranging ("LIDAR") system or a Radio Detection and Ranging ("RADAR") system. For example, the input image frames 161 can be or include a two- or three-dimensional point cloud of detected data points. In some implementations, the image frames 161 can be individual frames of video data.

The palm detection model 162 can be configured to detect one or more palms in input image frames 161 (e.g., still frames and/or video) by extracting features from the image frame and estimating one or more bounding box(es) 163 indicative of the position of the palm(s) in the image frame 161. The palm detection model 162 can estimate an oriented bounding box 163 in various ways. For example, the palm detection model 162 may estimate the oriented bounding box 163 based at least in part on an estimation of rigid objects in the image frame. As one example, the oriented bounding box 163 can be estimated based at last in part on the one or more contextually aware features extracted from an image frame.

The machine-learned palm detection model 162 can generate as output an oriented bounding box 163 indicating the position of a hand or palm within an image frame. An oriented bounding box can be used to accurately place and orient the palm or hand in the image frame to enable the machine-learned hand landmark model to accurately predict a plurality of hand landmark positions within the image frame.

The machine-learned hand landmark model 164 can perform key-point localization within a region defined by the bounding box to generate three-dimensional coordinates or 3D hand key-points 165 corresponding to a plurality of hand landmark positions within the image frame. For example, in some implementations, the machine-learned hand landmark model 164 of the hand tracking system can be configured to generate image data for an image frame region by cropping a corresponding image frame based at least in part on the respective oriented bounding box 163 generated by the palm detection model 162. The machine-learned hand landmark model 164 can detect hand landmark positions within the image frame region and perform key-point localization to generate three-dimensional coordinates corresponding to the plurality of hand landmark positions within the image frame.

A gesture recognition system 166 can be included in hand tracking system 160 in some embodiments. The gesture recognition system 166 can be configured to recognize or infer gestures 167 in image frames. The gesture recognition system 166 can be configured to identify a gesture, based at least in part on three-dimensional coordinates corresponding to a plurality of hand landmark positions within an image frame. The gesture recognition system can generate one or more gesture inferences 167 that indicate one or more gestures detected in an image frame. It is noted that the gesture recognition system is depicted by way of example. In other examples, additional or alternative functionalities may be implemented. A hand tracking system may include a machine-learned tracking system without additional incorporated functionality in some embodiments.

Figure 17:
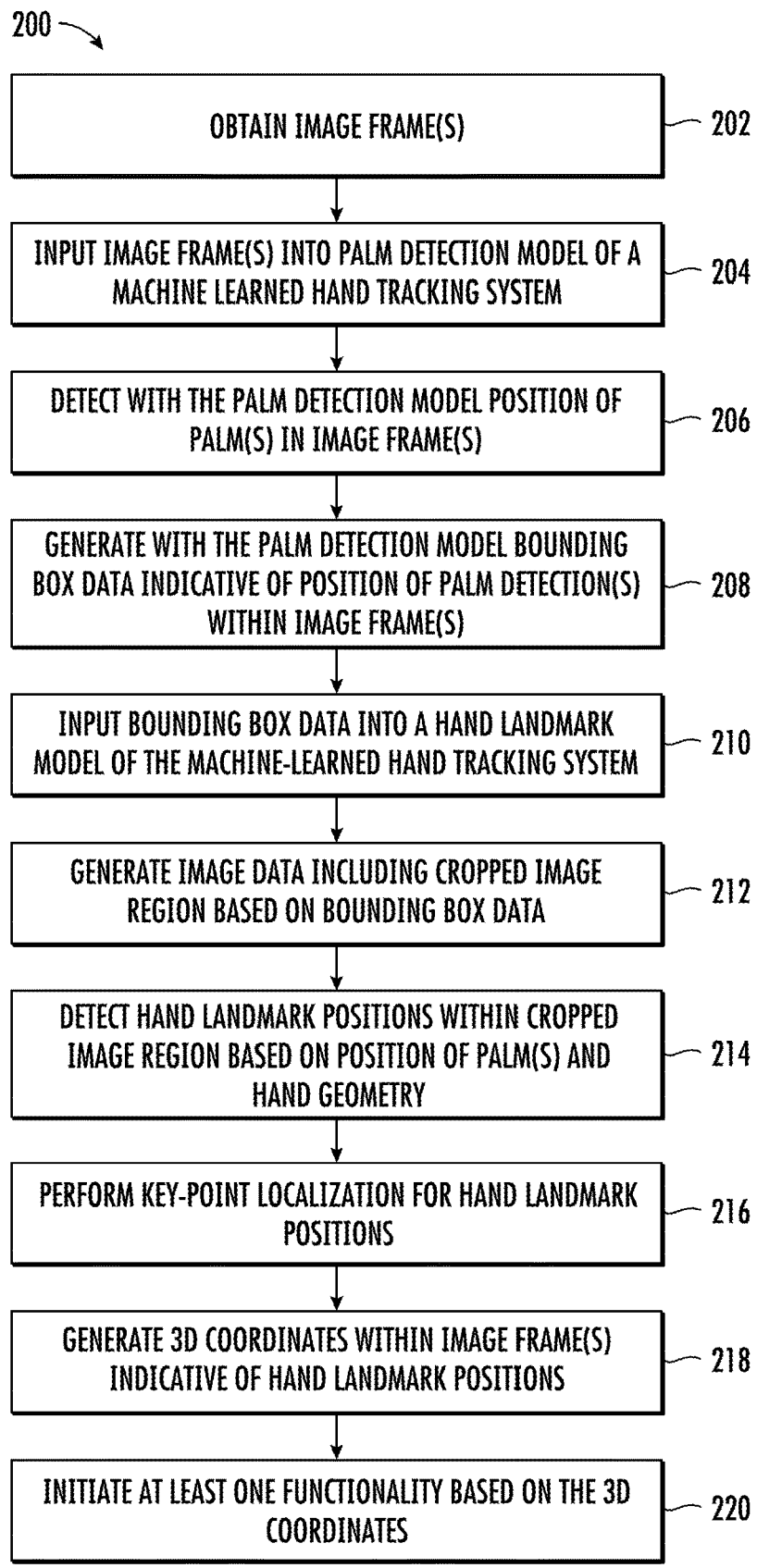
FIG. 17 depicts a flowchart illustrating an example hand tracking method using a machine-learned palm detection model and a machine-learned hand landmark model according to example embodiments of the present disclosure.
Figure 36A:
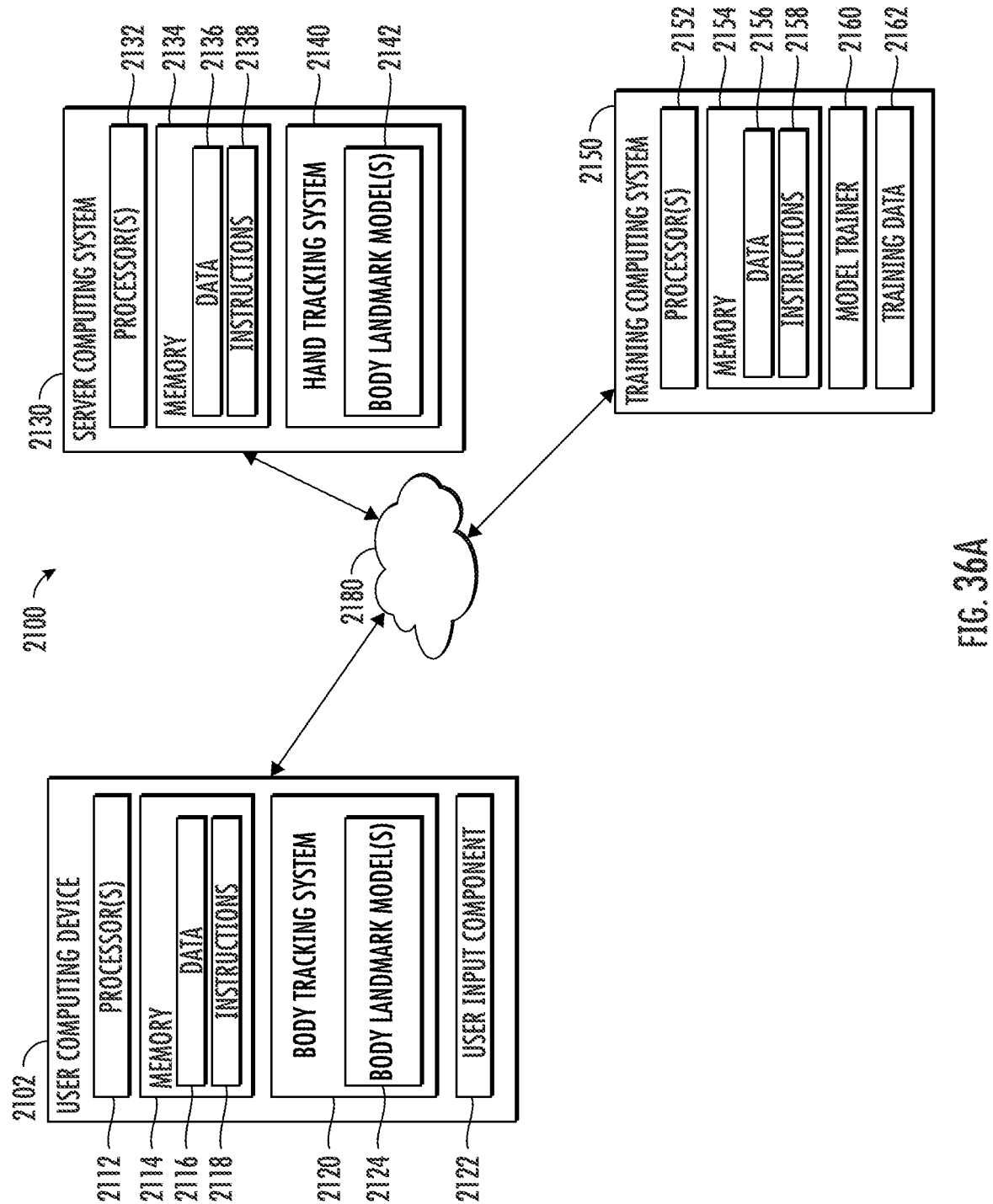
FIG. 36A depicts a block diagram of an example computing system that can be used to implement example embodiments of the present disclosure.

FIG. 17 depicts a flowchart illustrating an example method for hand tracking using a machine-learned palm detection model and a machine-learned hand landmark model. One or more portions of method 200 can be implemented by one or more computing devices such as, for example, one or more computing devices of a hand tracking computing system 2100, as illustrated in FIG. 36A. One or more portions of method 200 can be implemented as an algorithm on the hardware components of the devices described herein to, for example, tracking one or more hands depicted in imagery and initiate at least one functionality based on such tracking. In example embodiments, method 200 may be performed by or otherwise using a hand tracking system (e.g., hand tracking system 160) as described herein. One or more models may be implemented at a computing device of an internal electronics module, a removable electronics module, a local computing device, or a remote computing device as described herein. Although FIG. 17 depicts steps performed in a particular order for purposes of illustration and discussion, method 200 of FIG. 17 and other methods described hereinafter are not limited to the particularly illustrated order or arrangement. The various steps of the methods mentioned above can be omitted, rearranged, combined, and/or adapted in various ways without deviating from the scope of the present disclosure.

At 202, input data can be obtained by the hand tracking system. Input data can include imagery such as image data, including one or more image frames 161 (e.g., pictures or video frames), such as those provided by way of example with reference to FIG. 16. The image frames can include human perceptible images and/or other types of image frames such as LIDAR and RADAR frames.

At 204, the image frames 161 can be input into the palm detection model of a machine-learned hand tracking system. In response to receiving input image frames, at 206, the palm detection model can detect one or more palms in the image frames. For example, the palm detection model can extract features associated with palms from image frames to detect and predict palm positions. In some examples, the palm detection model 162 can additionally or alternatively use contextual features to detect palms. For instance, in addition to features associated with a human hand or palm, the model can extract features associated with an arm, body, face, and/or other personal features in the image frame that can provide contextual information.

At 208, the palm detection model can generate one or more bounding boxes indicative of the positions of the one or more palms detected in the image frame. In some examples, the machine-learned palm detection model can generate an oriented bounding box indicating the position of a hand or palm within an image frame. For example, the palm detection model may estimate the oriented bounding box based at least in part on an estimation of rigid objects in the image frame. The palm detection model can generate one bounding box for each palm detected in an image frame in some examples. The palm detection model can generate bounding box data indicative of one or more bounding boxes generated for each image frame.

At 210, bounding box data generated by the palm detection model can be input to the hand landmark model of the machine-learned hand tracking system. The bounding box data generated by the palm detection model can be indicative of the position of a palm in the image frame. In some examples, the bounding box data generated by the palm detection model can be indicative of the position of a hand in the image frame.

At 212, image data for a cropped image frame region can be generated based on the one or more bounding boxes generated by the palm detection model. In some examples, a machine-learned hand landmark model of the hand tracking system can be configured to generate image data for an image frame region by cropping a corresponding image frame based at least in part on the respective oriented bounding box generated by the palm detection model. For example, the hand landmark model can orient and/or crop an image frame based on the respective oriented bounding box to accurately display (or focus) the palm or hand in the image frame. It is noted that in some examples, an image cropping or other component separate from the hand landmark model may generate image data for the cropped image region and input the image data to the hand landmark model.

At 214, the hand landmark model can detect a plurality hand landmark positions within the cropped image frame region based on a position of the palms detected in the image frame and hand geometry. In some examples, the hand landmark positions can be detected based at least in part on the bounding box data generated by the palm detection model. In some examples, the hand landmark model can detect hand landmark positions based on the position of the palm or hand in the image frame and/or an orientation of the respective bounding box.

At 216, the hand landmark model can perform key-point localization for the detected hand landmark positions. For example, the machine-learned hand landmark model can detect a plurality of hand landmark positions within an image frame region, and generate three-dimensional coordinates corresponding to the hand landmark positions.

At 218, the hand landmark model can generate three-dimensional coordinates corresponding to the plurality of hand landmark positions within the cropped image frame. In some examples, the hand landmark model can generate three-dimensional coordinates based at least in part on the plurality of hand landmark positions within the image frame region by mapping the hand landmark positions within the image frame region to coordinates within the corresponding image frame.

At 220, three-dimensional coordinates can be used to initiate one or more functionalities based on the three-dimensional coordinates. Various functionalities based on the detection and tracking of hands can be initiated, such as gesture recognition. By way of example, the hand tracking system can initiate a functionality at one or more computing devices in response to detecting a gesture within one or more image frames. Example functionalities include, but are not limited to, invoking application controls based on gesture detection, handwriting applications or sign language applications, and the generation of various displays or renderings based on the hand tracking.

Figure 18:
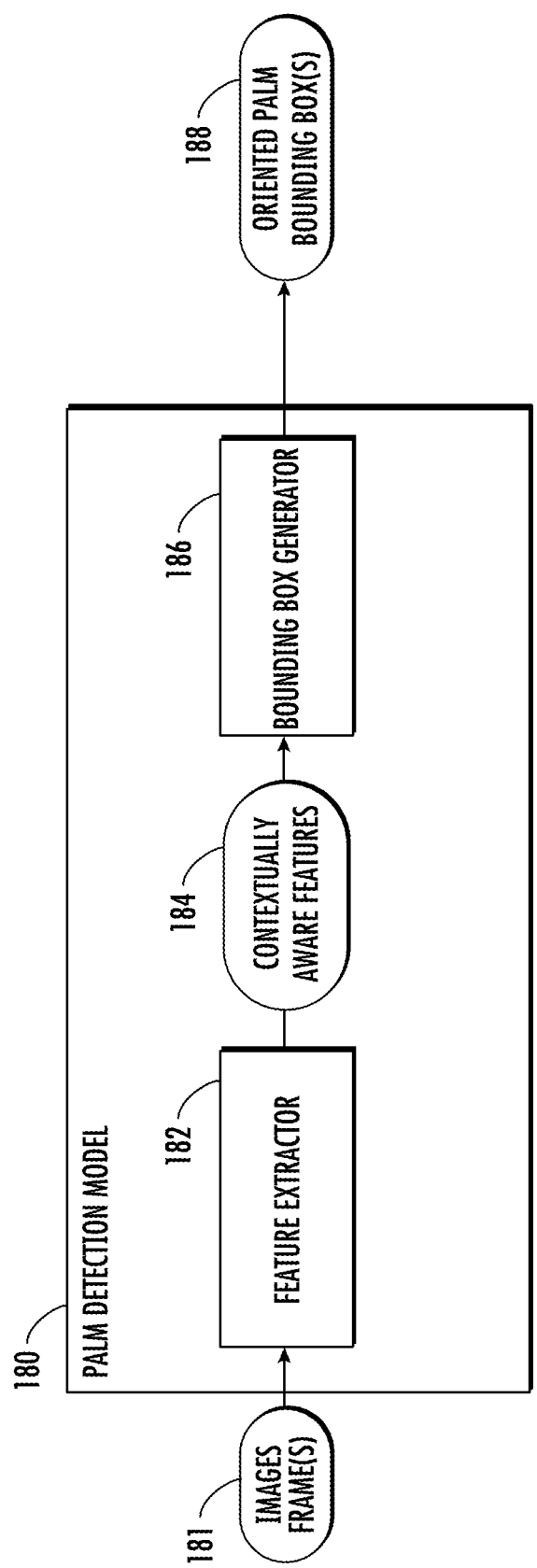
FIG. 18 depicts a block diagram of an example machine-learned palm detection model according to example embodiments of the present disclosure.

FIG. 18 depicts a block diagram of an example machine-learned palm detection model 180 according to example embodiments of the present disclosure. Palm detection model 180 can be employed in place of, for example, palm detection model 161 of FIG. 16. Machine-learned palm detection model 180 can be configured to process input image frames. The input image frames 181 can include two-dimensional image frames or three-dimensional image frames. For example, the image frames can include images captured by a camera (e.g., visible spectrum camera, infrared camera, hyperspectral camera, etc.). The images can be expressed in any number of different color spaces (e.g., greyscale, RGB, CMYK, etc.). As another example, the input image frames can include images generated by a Light Detection and Ranging ("LIDAR") system or a Radio Detection and Ranging ("RADAR") system. For example, the input imagery can be or include a two- or three-dimensional point cloud of detected data points.

Palm detection model 180 can be configured to detect one or more palms in an image frame (e.g., still frames and/or video) by extracting contextually aware features 184 from the image frame using a feature extractor 182. For example, the palm detection model 180 can extract features associated with palms from image frames to detect and predict palm positions. In addition to features associated with a human hand or palm, the contextually aware features can include features associated with an arm, body, face, and/or other personal features in the image frame that can provide contextual information. According to some implementations, a machine-learned palm detection model 180 can include an encoder-decoder feature extractor 182 that is configured to extract features 184 from images. The features 184 may include features relating to a palm, hand, as well as information indicative of a context for each of the image frames. For example, the encoder-decoder feature extractor can be configured to extract features indicative of any of the following: the presence and/or position of a human hand in the image frame, the presence and/or position of an arm in the image frame, the presence and/or position of a body in the image frame, or the presence and/or position of a face in the image frame.

Palm detection model 180 can include a bounding box generator 186 configured to generate an oriented bounding box 188 indicative of the position of a palm or hand detected in the image frame 181. As one example, the oriented bounding box can be estimated based at last in part on the one or more contextually aware features extracted from the image frame. An oriented bounding can be used to accurately place and orient the palm or hand in the image frame to enable the machine-learned hand landmark model to accurately predict a plurality of hand landmark positions within the image frame. By way of example, an oriented bounding box 188 can be generated at least in part by aligning the center of the wrist within the palm and a metacarpophalangeal joint of a middle finger with a y-axis of the image frame. As an example, the machine-learned palm detection model can be configured to generate the oriented bounding box 188 based at least in part on the one or more contextually aware features extracted from the image frame.

Figure 19:
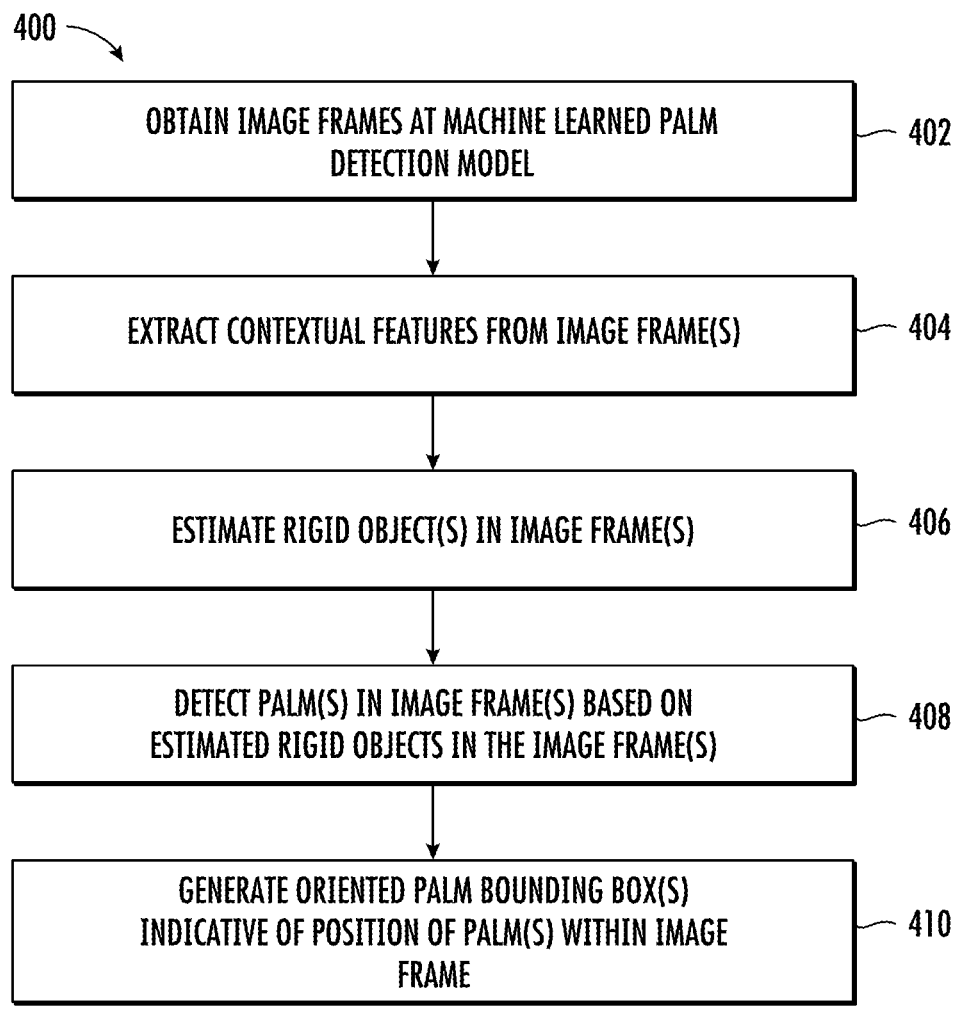
FIG. 19 depicts a flowchart illustrating an example method of generating bounding boxes using a machine-learned palm detection model according to example embodiments of the present disclosure.

FIG. 19 depicts a flowchart illustrating an example method 400 for generating bounding box(es) using a machine-learned palm detection model according to the embodiments of the present disclosure. At 402, image data such as one or more image frames 181 of image data can be obtained. For example, palm detection model 180 can obtain image data including two-dimensional image frames or three-dimensional image frames in example embodiments.

At (404), the palm detection model can extract one or more features from the input image frames 181. In some examples, the palm detection model can extract contextual features or contextually aware features from the input image frames. For example, the palm detection model 180 can extract features associated with palms from image frames to detect and predict palm positions. According to some implementations, a machine-learned palm detection model 180 can include an encoder-decoder feature extractor 182 that is configured to extract features from images. The features may include features relating to a palm, hand, as well as information indicative of a context for each of the image frames. For example, the encoder-decoder feature extractor 182 can be configured to extract features indicative of any of the following: the presence and/or position of a human hand in the image frame, the presence and/or position of an arm in the image frame, the presence and/or position of a body in the image frame, or the presence and/or position of a face in the image frame. The palm detection model 180 can use the contextual information associated with other features to aid in estimating the position of a palm within an image frame.

At (406), rigid objects in the image frame can be estimated. Rigid objects in an image frame are object detections in an image frame that have proportions or features similar to palms or hands. For example, the palm detection model 180 may extract features associated with palms from image frames to detect and predict palm positions by estimating rigid objects in the image frames indicative of palms.

At (408), the palm detection model can detect one or more palms in an image frame based at least in part on the estimation of rigid objects in the image frame.

At (410), the palm detection model can generate one or more oriented palm bounding boxes 109 that indicate the position of the one or more detected palms within the input image frame. For example, the palm detection model 180 can estimate the oriented bounding box 188 based, at least in part on an estimation of rigid objects in the image frame. In some examples, the machine-learned palm detection model can expand a bounding box associated with a palm to identify a possible hand location. For instance, the palm detection model can estimate one or more first bounding boxes indicative of one or more detected palms in an image frame and expand and/or shift the one or more first bounding boxes to generate one or more second bounding boxes indicative of the location of an entire hand in the image frame.

An oriented bounding box 188 can be used to accurately place and orient the palm or hand to enable a machine-learned hand landmark model to accurately predict a plurality of hand landmark positions within the image frame. By way of example, an oriented bounding box 188 can be generated at least in part by aligning the center of the wrist within the palm and a metacarpophalangeal joint of a middle finger with a y-axis of the image frame.

FIGS. 20A-20B depict example image frames illustrating the detection of palms using a machine-learned palm detection model according to example embodiments of the present disclosure. FIG. 20A depicts an example image frame with detections illustrating the application of a machine-learned palm detection model according to example embodiments of the present disclosure. In this example, the machine-learned palm detection model 180 detects a palm in the image frame and generates a bounding box to indicate the position of the palm in the image frame. A graphical depiction of a bounding box 502 is shown in FIG. 20A. FIG. 20A provides an example of a bounding box indicating the position of a palm 510 in an image frame.

In FIG. 20B, a detection by the machine-learned palm detection model of a palm in the image frame is depicted, including a bounding box for a hand. The palm detection model can generate bounding box data that identifies a bounding box 554 including coordinates or other data that provides an estimation of a location of a position of the hand in the image frame. In some examples, three-dimensional cartesian coordinates can be used to identify a bounding box. In other examples, pixel coordinates can be used. The machine-learned palm detection model 180 can estimate a bounding box 552 that indicates the position of the palm in the image frame, then expand bounding box 552 to generate a bounding box 554 that indicates the position of the hand in the image frame. In some instances, the machine-learned palm detection model can expand a bounding box indicative of a position of a palm in an image frame based at least in part on the actual size of the input image frame to indicate a position of a hand in the image frame. In some examples, the machine-learned palm detection model can expand the bounding box indicative of the position of the palm in an image frame based at least in part on the ratio of the size of the detected palm and the size of the input image frame. Alternatively or additionally, in some examples, a fixed scale can be used to expand the bounding box indicative of the position of the palm to indicate the position of the hand in the image frame.

Figure 21:
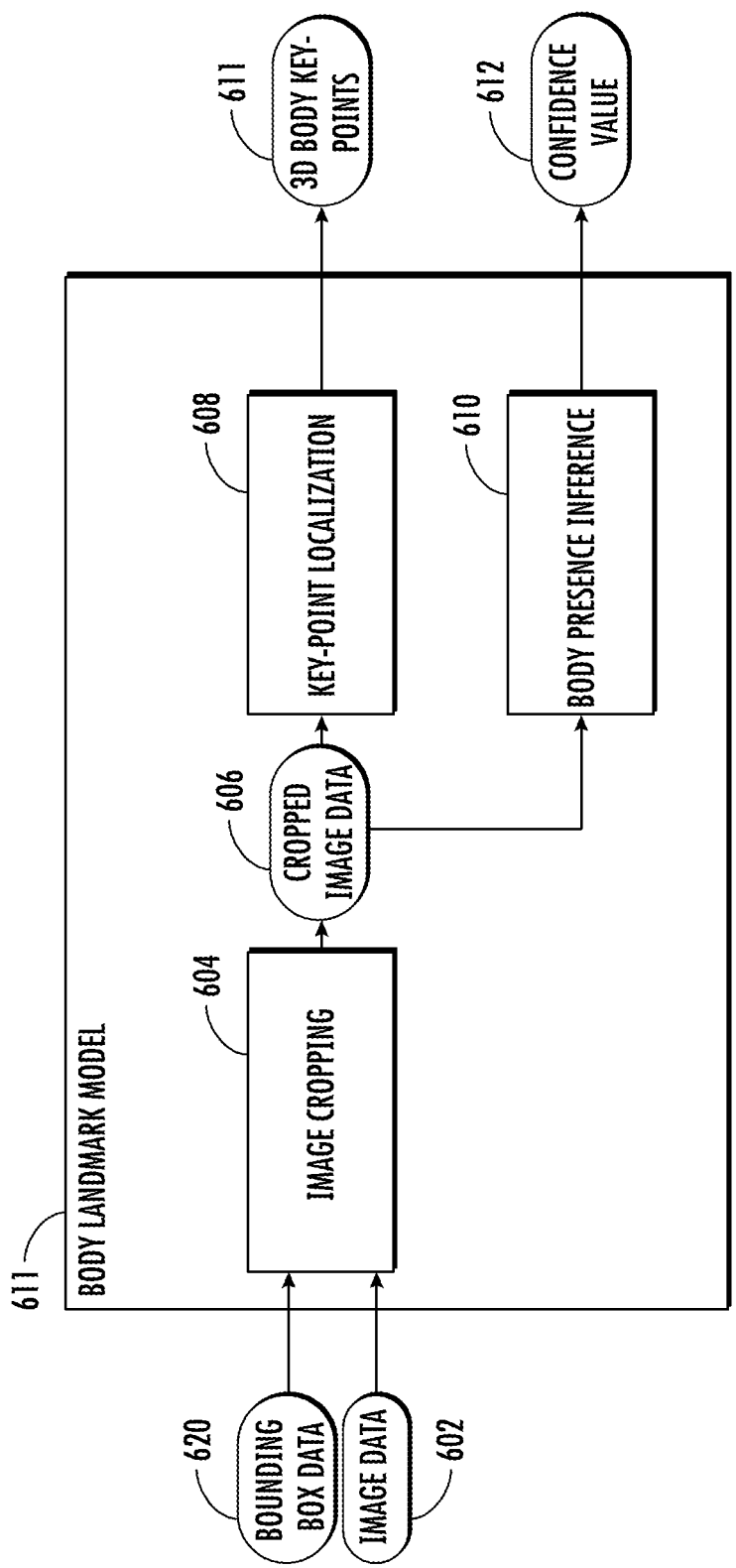
FIG. 21 depicts a block diagram of an example machine-learned hand landmark model according to example embodiments of the present disclosure.

FIG. 21 depicts a block diagram of an example machine-learned body landmark model 611 according to example embodiments of the present disclosure. The machine-learned body landmark model 611 can detect body landmark positions within an image frame region and perform key-point localization to generate three-dimensional coordinates 165 corresponding to the plurality of body landmark positions within the image frame. In some examples, the body landmark model can additionally generate a confidence value 612 associated with a determination as to whether an image frame depicts a body.

Body landmark model 611 can include an image cropping component configured to obtain image data 602 and bounding box data 620. Image cropping unit 604 can crop an image frame based at least in part on the respective orientated bounding box 620 corresponding to the image frame. In some examples, the body landmark model 611 can generate cropped image data or cropped image frame region 606 for an image frame region by cropping the corresponding image frame based at least in part on the respective orientated bounding box 620. By orienting and/or cropping an image frame based on the respective oriented bounding box, model can accurately display (or focus) the palm or body in the image frame. In some examples, the machine-learned body landmark model 611 can rotate the image frame region based on the orientation of the bounding box corresponding to at least a portion of a body and/or scale the image frame region to a pre-defined sized image frame region (e.g., 265×265 pixels). In some embodiments, the body landmark model can be configured to obtain image data or data indicative of an image frame region corresponding to the respective oriented bounding box as input. For instance, a separate image cropping component can generate an image frame region using a bounding box as described.

The body landmark model 611 can include a key-point localization component 608 or other component configured to detect a plurality of body landmark positions (e.g., fingers, thumb, knuckles, joint positions, etc.) within the image frame region identified by cropped image data or cropped image frame region 606. The body landmark positions can be detected using the bounding box in some examples. The body landmark positions can be detected based on the position of the palm or body in the image frame region and/or an orientation of the respective bounding box. In some examples, such as in hand detection, the body landmark positions (e.g., joints within fingers, between the palm and fingers, between appendages, etc.) can be determined based on the location of the palm and the orientation of the palm in the image frame. For example, the position of body landmarks can be based on the position and orientation of the palm or body in the image.

In some examples, the key-point localization component 608 can detect landmarks based at least in part on body geometry associated with at least a portion of a depicted body. For instance, the model can identify a position of a center of a wrist attached to the palm in an image frame and one or more extracted features indicative of body geometry within the image frame. In some examples, one or more features indicative of body geometry of at least a portion of a body detected in an image frame can be extracted. For instance, the body landmark model 611 can detect body landmark positions (e.g., of a hand) by identifying features extending from a wrist feature towards one or more finger features. The feature extension can be identified in a direction from the center of a wrist connected to the palm in the image frame.

The key-point localization component 608 can perform key-point localization to generate three-dimensional coordinates 165 corresponding to a plurality of body landmark positions. For example, the machine-learned body landmark model 611 can detect a plurality of body landmark positions within an image frame region, and generate three-dimensional coordinates corresponding to the body landmark positions. In some examples, key-point localization component 608 can map the plurality of body landmark positions within the image frame region to coordinates within the corresponding image frame. In this manner, the body landmark model can detect body landmark positions in a cropped and/or oriented image frame region and map the positions to a corresponding input image frame, generating the three-dimensional coordinates. As another example, the key-point localization component 608 can detect a plurality of body landmark positions within an image frame and map the plurality of body landmark positions as three-dimensional coordinates within the image frame. In some examples, the machine-learned body landmark model can use a learned consistent internal body pose representation to perform key-point localization.

The body landmark model can additionally include a body presence inference component 610 that is configured to determine whether a body is depicted in an image frame. Component 610 can generate an output including a confidence value 612 indicative of the probability that a body is depicted in an image frame. Body tracking system 611 can selectively invoke the palm detection model 180 based on the confidence value 612 associated with body presence in the image frame. If the confidence value 612 satisfies a pre-defined threshold, the body landmark model 611 can generate and/or provide data indicative of three-dimensional coordinates corresponding to body landmark positions within the image frame. If the confidence value 612 does not satisfy a pre-defined threshold, the body landmark model 611 can input the corresponding image frame into the palm detection model 180.

Figure 22:
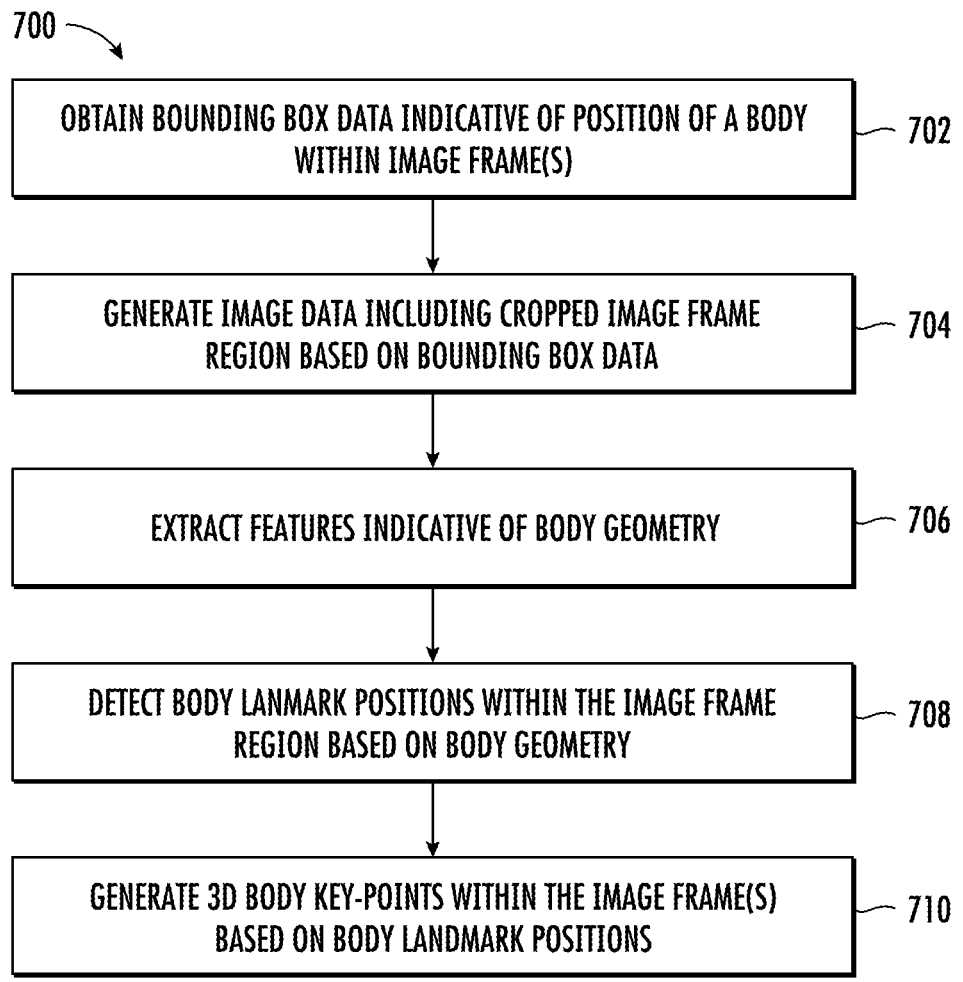
FIG. 22 depicts a flowchart illustrating an example method of generating three-dimensional hand key-points using a machine-learned hand landmark model according to example embodiments of the present disclosure.

FIG. 22 depicts a flowchart illustrating an example method 700 of generating three-dimensional body coordinates or key-points according to example embodiments of the present disclosure. In some implementations, one or more operations of method 700 can be performed by a body landmark model (e.g., body landmark model 611). At 702, bounding box data can be obtained indicative of the position of one or more palms in an image frame as detected by the palm detection model. In some examples, the bounding box data can be indicative of the position of one or more bodies in the image frame.

At (704), method 700 can include generating image data for an image frame region by cropping a corresponding image frame based at least in part on a respective oriented bounding box. For example, the body landmark model 611 can orient and/or crop an image frame based on the respective oriented bounding box to accurately display (or focus) the palm or body in the image frame. In other examples, an image cropping unit separate from the body landmark model can be used. Method 700 can include rotating, scaling, cropping, and/or orienting the image frame based on the portion of the body in the image frame.

At (706), method 700 can include extracting features indicative of body geometry within the image frame or within the cropped image frame region 606. Body geometry can include biometrics and other features that can identify the shape of a body. Body geometry can include features of a body (e.g., a hand) along various dimensions (e.g., length between knuckles, width of fingers, width of knuckles, width of the palm, length of the palm, length of fingers, etc.).

At (708), method 700 can include detecting body landmark positions (e.g., fingers, thumbs, knuckles, joint positions, etc.) within the image frame region based on body geometry. For instance, the body landmark model 611 can identify a position of a center of a wrist attached to the palm in an image frame and one or more extracted features indicative of body geometry within the image frame. In some examples, the body landmark model 611 can detect body landmark positions by identifying features extending from a wrist feature towards one or more finger features. The feature extension can be identified in a direction from the center of a wrist connected to the palm in the image frame. In some examples, body landmark positions can be identified using one or more body geometry features, such as for example, by detecting a thumb in an image frame and using the detected thumb to detect a plurality of body landmarks within the image frame.

Figure 23:
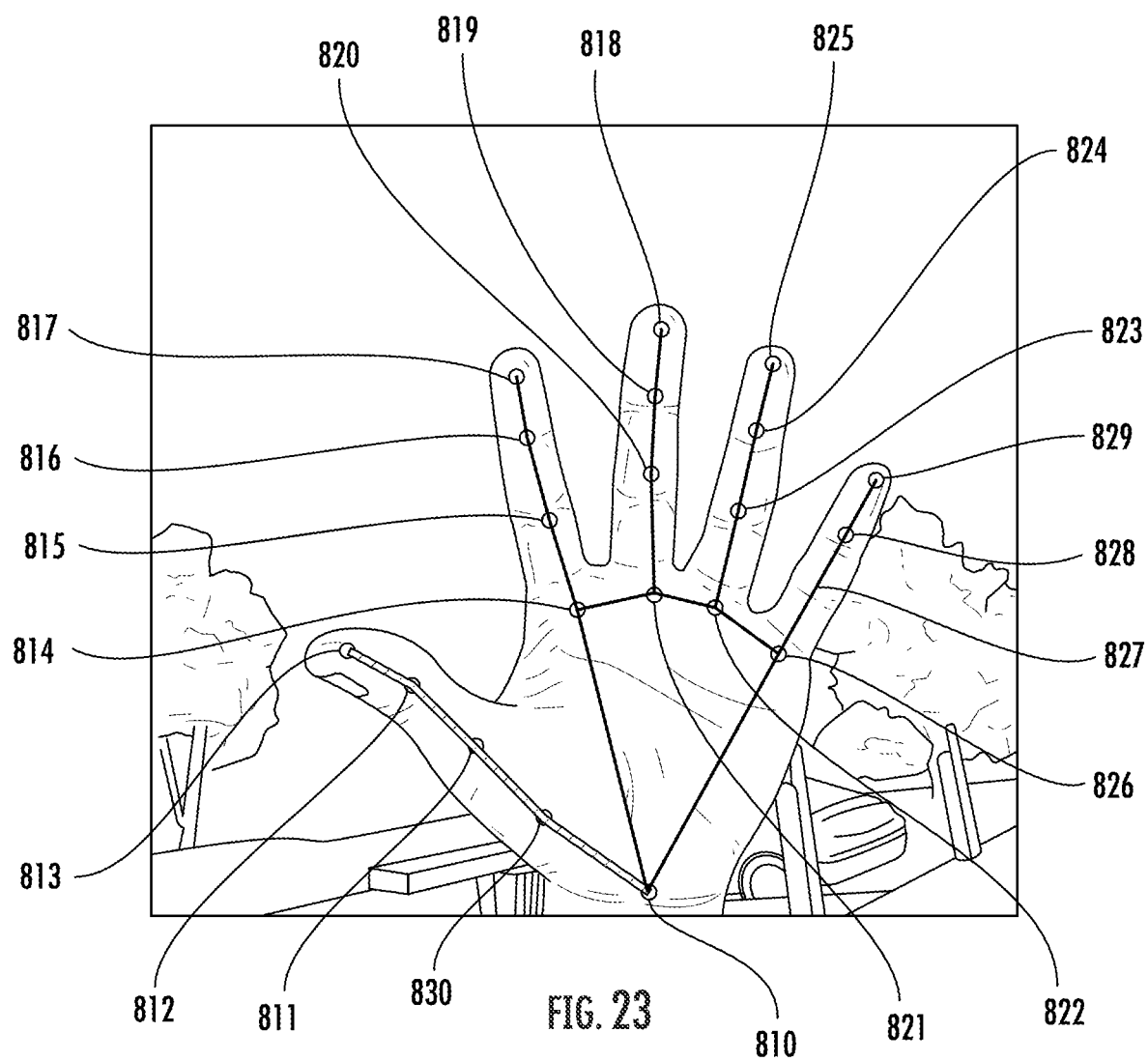
FIG. 23 depicts an example of landmark detections within an image frame using a machine-learned hand landmark model according to the embodiments of the present disclosure.

FIG. 23 depicts an example of landmark detections within an image frame illustrating the application of a machine-learned hand landmark model according to example embodiments of the present disclosure. In this example, a plurality of hand landmark positions 810-831 within a hand depicted in an image frame are depicted. In some examples, 21 hand landmark positions can be detected. However, more or fewer hand landmark positions can be detected by the hand landmark model. In this example, position 810 indicates the position of a hand landmark (e.g., a center of a wrist for palm or hand detected in the image frame). Position 820 indicates the position of a metacarpophalangeal joint of a middle finger of the hand detected in the image frame. Positions 813, 817, 818, 825, and 829 indicate the positions of the tips of the thumb, first finger, middle finger, ring finger, and little finger respectively in the image frame. Positions 814, 820, 823, and 827 indicate the positions of metacarpophalangeal joints of each of the fingers in the detected hand in the image frame.

Figure 24:
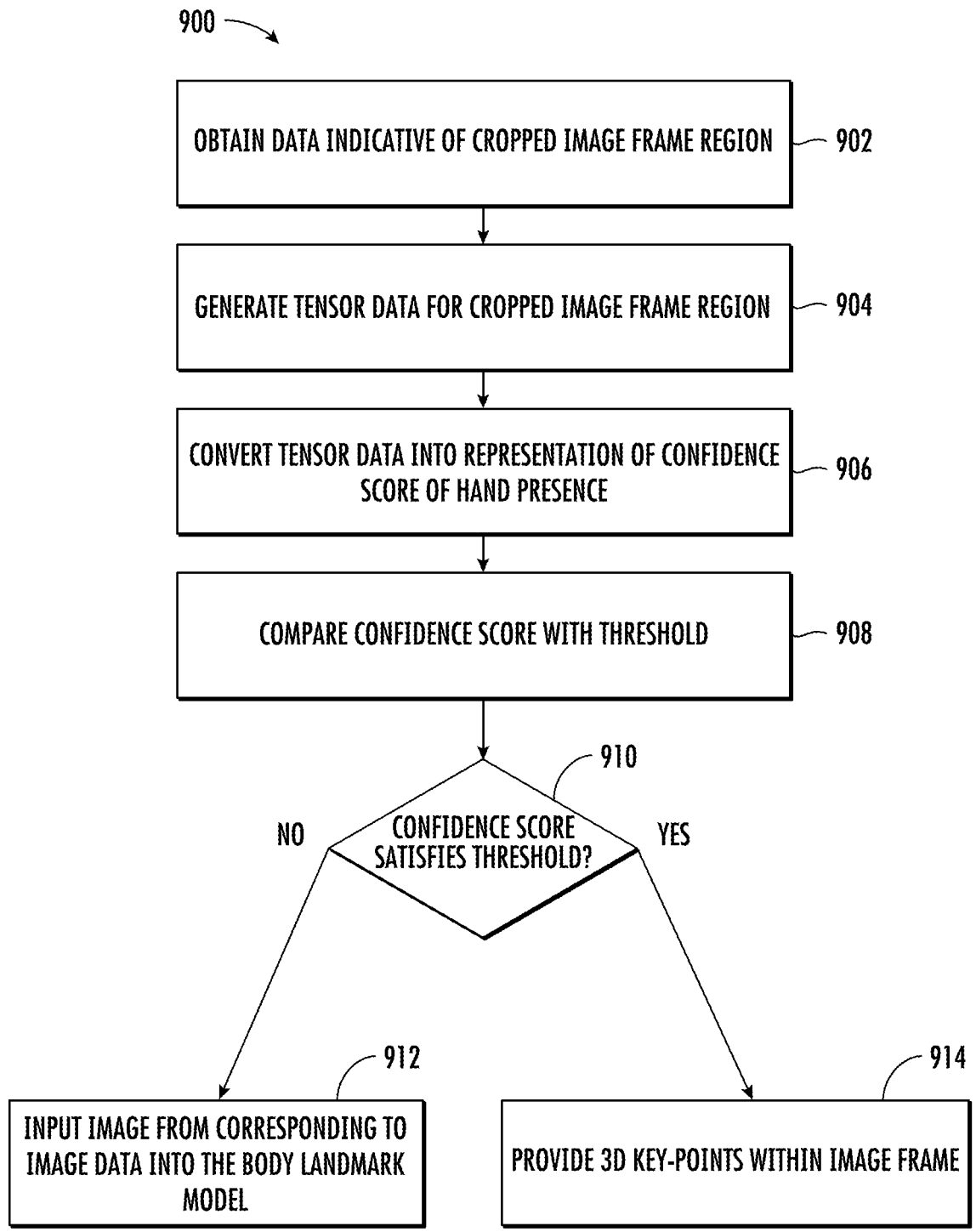
FIG. 24 depicts a flowchart illustrating an example method of generating a confidence value indicative of the presence of a hand within an image frame using a machine-learned hand landmark model according to example embodiments of the present disclosure.

FIG. 24 depicts a flowchart illustrating an example method 900 of generating a confidence value indicative of the presence of a body within an image frame according to example embodiments of the present disclosure. Method 900 can be performed by or using a machine-learned body landmark model. At (902), method 900 can include generating image data for an image frame region by cropping a corresponding image frame based at least in part on a respective oriented bounding box.

At (904), method 900 can include generating tensor data for the cropped image frame region. For example, the body landmark model can use a converter to convert an image frame into an image tensor. An inference component can be used to convert an image tensor into an output tensor vector that represents detection boxes, key-points, or a confidence score or confidence value indicative of the probability that a body is present in the image frame.

At (906), the output tensor vector generated by the inference component can be converted into a number indicative of the confidence score. For example, the output vector tensor generated by the inference component can be split into data representative of the detection boxes, key-points, and confidence score to determine whether a body is present in the image frame, the output vector tensor. In some examples, the representation of the confidence score can be a float value or any numerical value indicative of probability.

At (908), the confidence score representation is compared to a pre-determined threshold value to determine whether a body is present in the image frame. For example, in some embodiments, the threshold value can be 0.7. In some examples, the pre-defined threshold value can be determined by the user. Alternatively or additionally, the pre-defined threshold value can be determined using a machine-learned model.

At (910), the body landmark model can determine whether the confidence score or confidence value indicating the probability that a body is present in the image frame satisfies a pre-defined threshold. At (914), if the confidence value satisfies the pre-defined threshold, the body landmark model can generate and/or provide data indicative of three-dimensional coordinates corresponding to body landmark positions within the image frame.

At (912), If the confidence value does not satisfy the pre-defined threshold, the body landmark model can input the corresponding image frame into the body landmark model.

Figure 25:
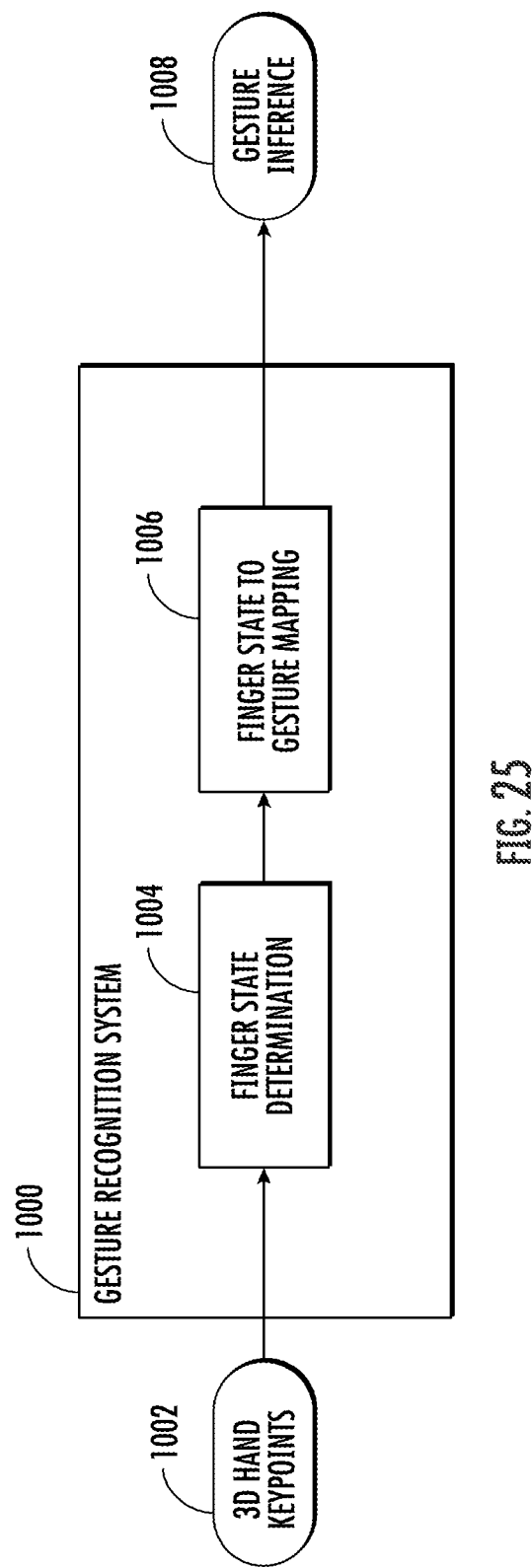
FIG. 25 depicts a block diagram of an example gesture recognition system according to example embodiments of the present disclosure.

FIG. 25 depicts a block diagram of an example gesture recognition system according to example embodiments of the present disclosure. Gesture recognition system 1000 can identify a gesture in an image frame based at least in part on three-dimensional coordinates 1002 (e.g., generated by the hand landmark model 164) for a plurality of hand landmark positions.

The gesture recognition system 1000 can determine whether an image frame depicts one or more gestures based at least in part on the three-dimensional coordinates 1002. The gesture recognition system can access data indicative of a hand skeleton in some embodiments. The hand skeleton can be defined using the three-dimensional coordinates corresponding to a plurality of hand landmark positions within an image frame. For example, the hand landmark model can define a hand skeleton by defining lines or edges that connecting the three-dimensional coordinates corresponding to a plurality of hand landmark positions in the image frame such that the connected hand landmark positions define a hand skeleton. In some examples, the hand skeleton can be defined as the set of three-dimensional coordinates. The hand skeleton can be generated by the gesture recognition system in some embodiments.

The gesture recognition system 1000 can determine a set of finger states associated with each finger of the hand skeleton. In some examples, a finger state component 1004 can be used to determine a finger state associated with each finger in the rendered hand skeleton. For example, the set of finger states indicative of whether a finger is bent, straight, or oriented, etc. associated with each finger of the hand skeleton can be determined. In some examples, the finger states can be generated based at least in part on the accumulated angle of joints associated with each finger of the hand skeleton. The accumulated angle of joints can be determined based at least in part on the three-dimensional coordinates corresponding to the plurality of hand landmark positions such as joints, knuckles, fingers, and/or thumbs.

The gesture recognition system 1000 can generate a gesture inference 1008 identifying a gesture detected in an image frame by a mapping 1006 of a determined set of finger states to one or more pre-defined gestures. For example, the gesture recognition system 1000 can map the finger states to one or more pre-defined gestures to identify a gesture in an image frame using a finger state to gesture mapping component 1006. In some examples, gesture recognition system 1000 may include a mapping system including a data store of mappings between finger states and pre-defined gestures.

The gesture recognition system can generate data indicative of a hand skeleton using, in some examples, a hand skeleton component. In other examples, the hand landmark model may include a hand skeleton component. The hand skeleton component can define a hand skeleton using three-dimensional coordinates corresponding to a plurality of hand landmark positions within an image frame. For example, the gesture recognition system can define a hand skeleton by defining lines or edges that connect the three-dimensional coordinates corresponding to a plurality of hand landmark positions in the image frame such that the connected hand landmark positions define a hand skeleton. In some examples, the hand skeleton can be defined as the set of three-dimensional coordinates.

Figure 26:
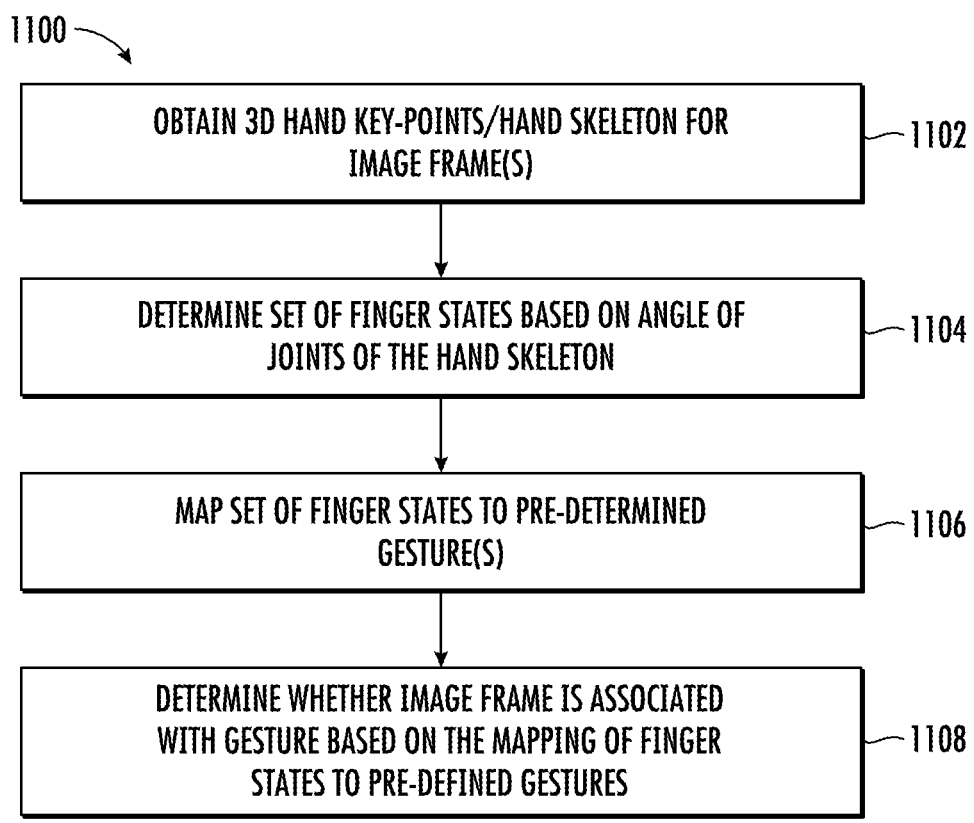
FIG. 26 depicts a flowchart illustrating an example method of identifying gesture(s) in an image frame using a gesture recognition system according to example embodiments of the present disclosure.

FIG. 26 depicts a flowchart illustrating an example method of identifying gesture(s) in an image frame according to example embodiments of the present disclosure. In some examples, method 1100 can be performed by a gesture recognition system (e.g., the gesture recognition system 1000). At 1102, method 1100 includes obtaining three-dimensional coordinates or 3D hand key-points 1002 corresponding to a plurality of hand landmarks within an image frame. For example, the gesture recognition system can obtain sets of three-dimensional coordinates generated by the machine-learned hand landmark model and can map the three-dimensional coordinates to determine whether one or more pre-defined gestures are present in an image frame. In some embodiments, the gesture recognition system 1000 can obtain data indicative of a hand skeleton. For example, the hand landmark model and/or gesture recognition system can define a hand skeleton using edges or lines that connect the three-dimensional coordinates for hand landmark positions in the image frame such that the connected hand landmark positions define a hand skeleton. In some examples, the hand skeleton can be defined as the set of three-dimensional coordinates. In some embodiments, a tracking system does not necessarily generate a hand skeleton and determines a set of finger states using the three-dimensional hand coordinates corresponding to the hand landmark positions in the image frame.

At 1104, method 1100 can include determining a set of finger states based on the angle of the joints in the hand skeleton. For example, a set of finger states (e.g., bent, straight, oriented, etc.) associated with each finger of the hand skeleton can be determined. The finger states can be determined based at least in part on the accumulated angle of joints associated with each finger of the hand skeleton. The accumulated angle of joints can be determined based at least in part on the three-dimensional coordinates corresponding to the plurality of hand landmark positions such as joints, knuckles, fingers, and/or thumbs.

At (1108), method 1100 can include mapping the set of finger states to one or more pre-defined gestures. For example, the gesture recognition system 1000 can associate a gesture detected in an image frame with one or more pre-defined gestures based at least in part on mapping the determined set of finger states to a set of pre-defined gestures. In some examples, the gesture recognition system 1000 may include a mapping system including a data store of mappings between finger states and pre-defined gestures. Additionally or alternatively, the gesture recognition system may include one or more machine-learned classifiers that are trained to identify pre-defined gestures based at least in part on three-dimensional hand coordinates generated by the hand landmark model.

Figure 27:
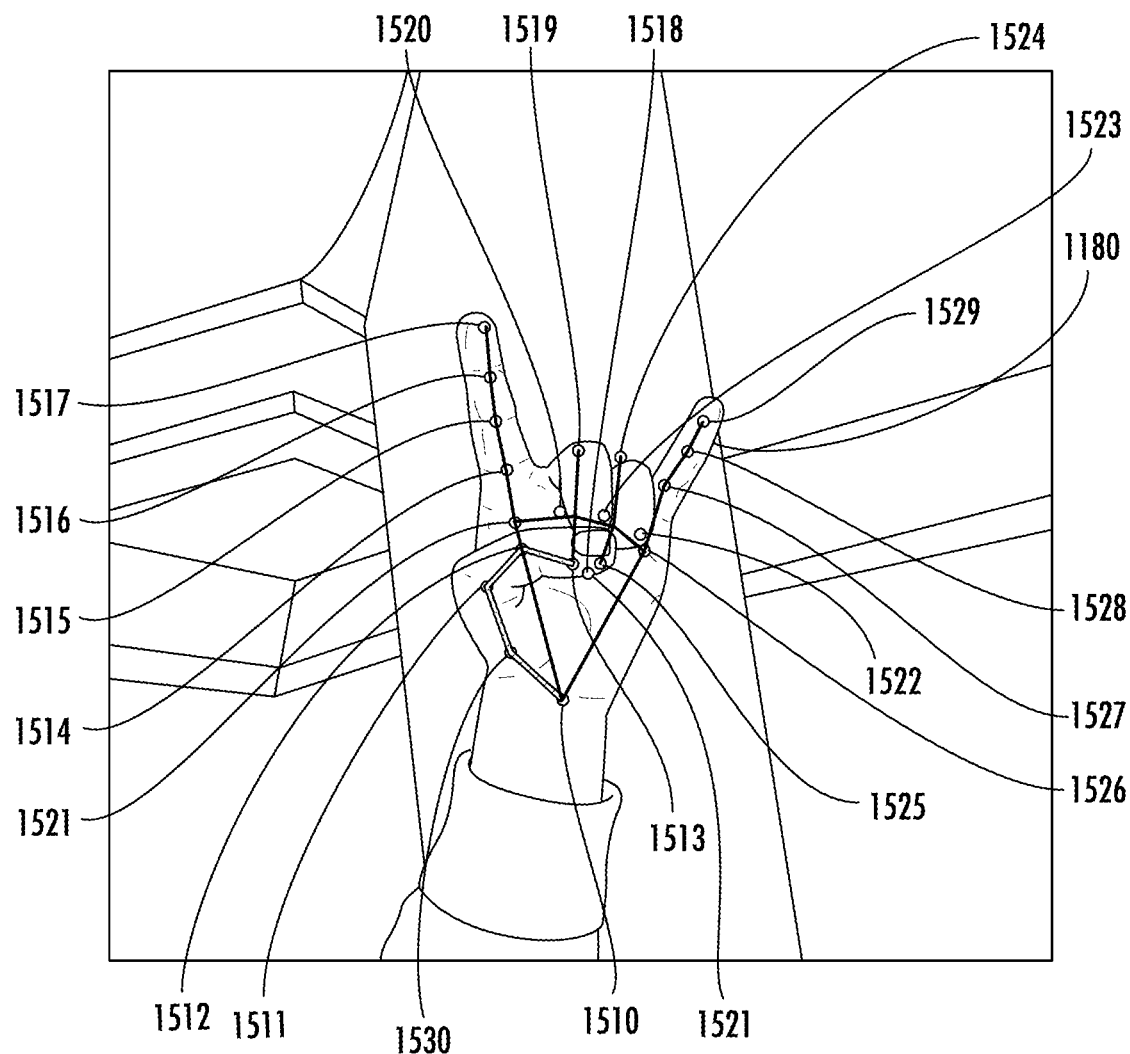
FIG. 27 depicts example detections within an image frame using a gesture recognition system according to example embodiments of the present disclosure.

FIG. 27 depicts an example of a rendered image frame including a graphical illustration of a set of hand landmark positions 1510-1531 as can be determined by a hand landmark model in accordance with example embodiments of the present disclosure. The rendered image frame additionally includes a graphical depiction of a predicted hand skeleton 1180 as can be determined by the hand landmark model for an input image frame. In some embodiments, a gesture recognition system may identify a particular gesture based on the depiction of the hand in the image frame.

Figure 28:
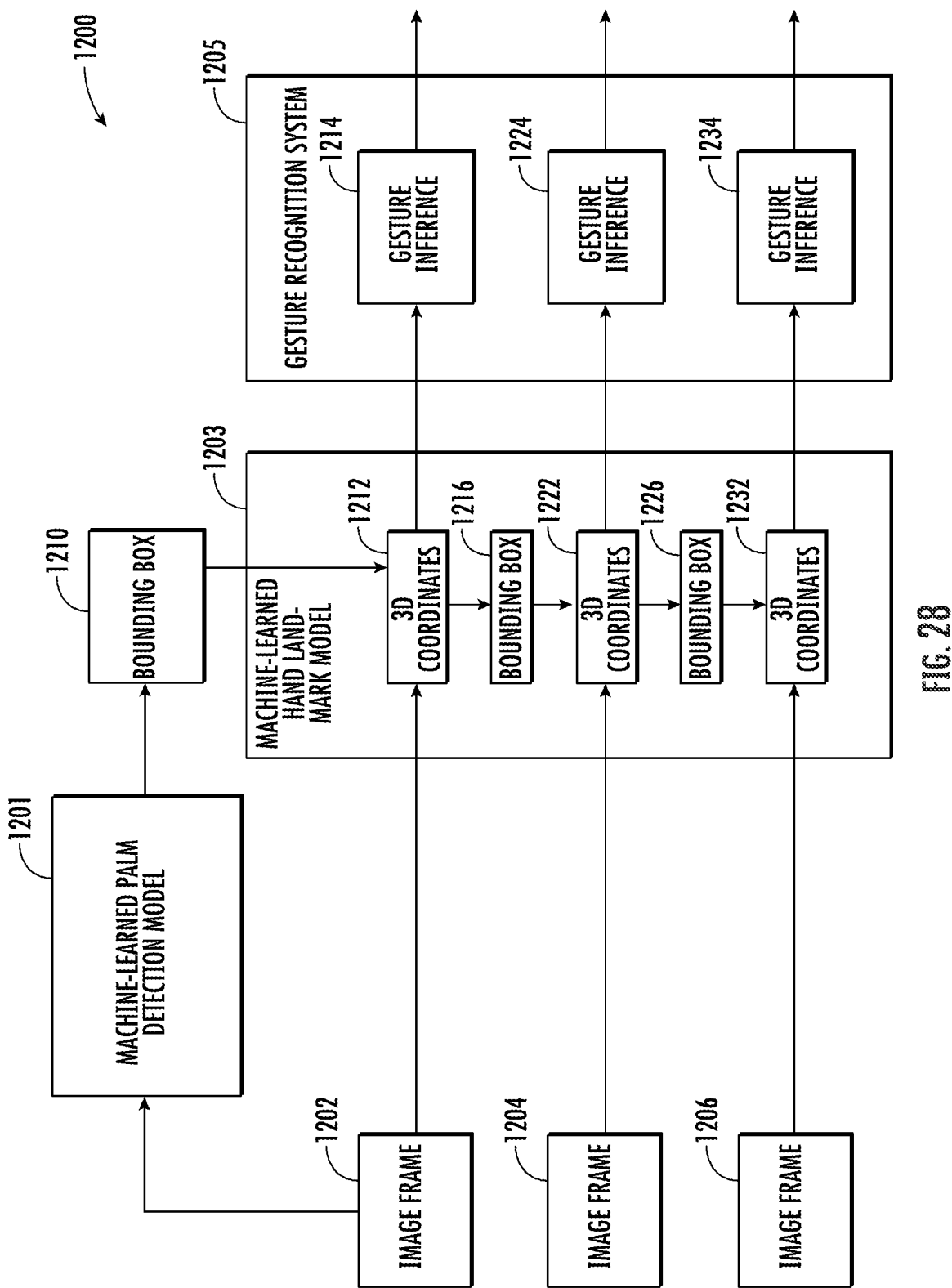
FIG. 28 depicts a block diagram of an example hand tracking system including a machine-learned palm detection model, a machine-learned hand landmark model, and a gesture recognition system according to example embodiments of the present disclosure.

FIG. 28 depicts a block diagram of an example hand tracking system 1200 including a machine-learned palm detection model 1201 (e.g., palm detection model 162 and/or palm detection model 180), a machine-learned hand landmark model 1203 (e.g., hand landmark model 164), and a gesture recognition system 1205 (e.g., gesture recognition system 1000) according to example embodiments of the present disclosure. In some examples, the hand tracking system can apply the palm detection model selectively to image frames input to the tracking system and can persistently apply the hand landmark model to each image frame. In other implementations, the hand landmark model may be applied to less than all of the image frames. In FIG. 28, a first image frame 1202 in a sequence of image frames can be input into the palm detection model 1201. Palm detection model 1201 can detect or otherwise determine whether one or more palms are depicted in image frame 1202. If a palm is detected in the image frame, palm detection model 1201 can generate a bounding box 1210 indicative of the position of the detected palm. In some examples, bounding box 1210 can indicate a position of a hand for a detected palm. The bounding box can be generated by expanding a detected position of the palm using one or more expansion parameters. Bounding box 1210 can be input into the hand landmark model 1203 to generate three-dimensional coordinates 1212 corresponding to a plurality of hand landmarks in image frame 1202. The three-dimensional coordinates 1212 for the hand depicted in image frame 1202 can be provided to gesture recognition system 1205. Gesture recognition system 1205 can identify a gesture depicted in the first image frame 1202. In some examples, hand landmark model 1203 can also generate a bounding box 1216 indicative of the likely position of the palm or hand in the subsequent image frame 1204. For example, the hand landmark model 1203 can generate a bounding box 1216 indicative of the position of a palm or hand in image frames 1204 based on the bounding box 1210 and/or three-dimensional coordinates 1212 generated for the first image frame 1202. Bounding box 1216 can be used by the hand landmark model 1203 to determine three-dimensional coordinates for the subsequent image frame 1204. Similarly, hand landmark model 1203 can generate three-dimensional coordinates 1222 corresponding to a plurality of hand landmarks in image frame 1204. The 3D coordinates 1222 for the hand depicted in image frame 1204 can be provided to gesture recognition system 1205 to determine whether a gesture is depicted in image frame 1204. Hand landmark model 1203 can generate a bounding box 1226 indicative of the position of a palm or hand in image frame 1204 based on the bounding box 1216 and/or three-dimensional coordinates 1222 generated for the second image frame 1204. Bounding box 1226 can be used by hand landmark model 1203 to determine three-dimensional coordinates 1232 for the subsequent image frame 1206. This technique can enable the palm detection model to be applied on selective image frames. In some examples, the hand tracking system can perform hand detection using the machine-learned hand landmark model. If a hand is detected by the hand landmark model, the system can perform keypoint localization without invoking the palm detector model to identify a palm in the image frame. If a hand is not detected by the hand landmark model, the tracking system can provide the image frame to the palm detection model for palm detection.

Figure 29:
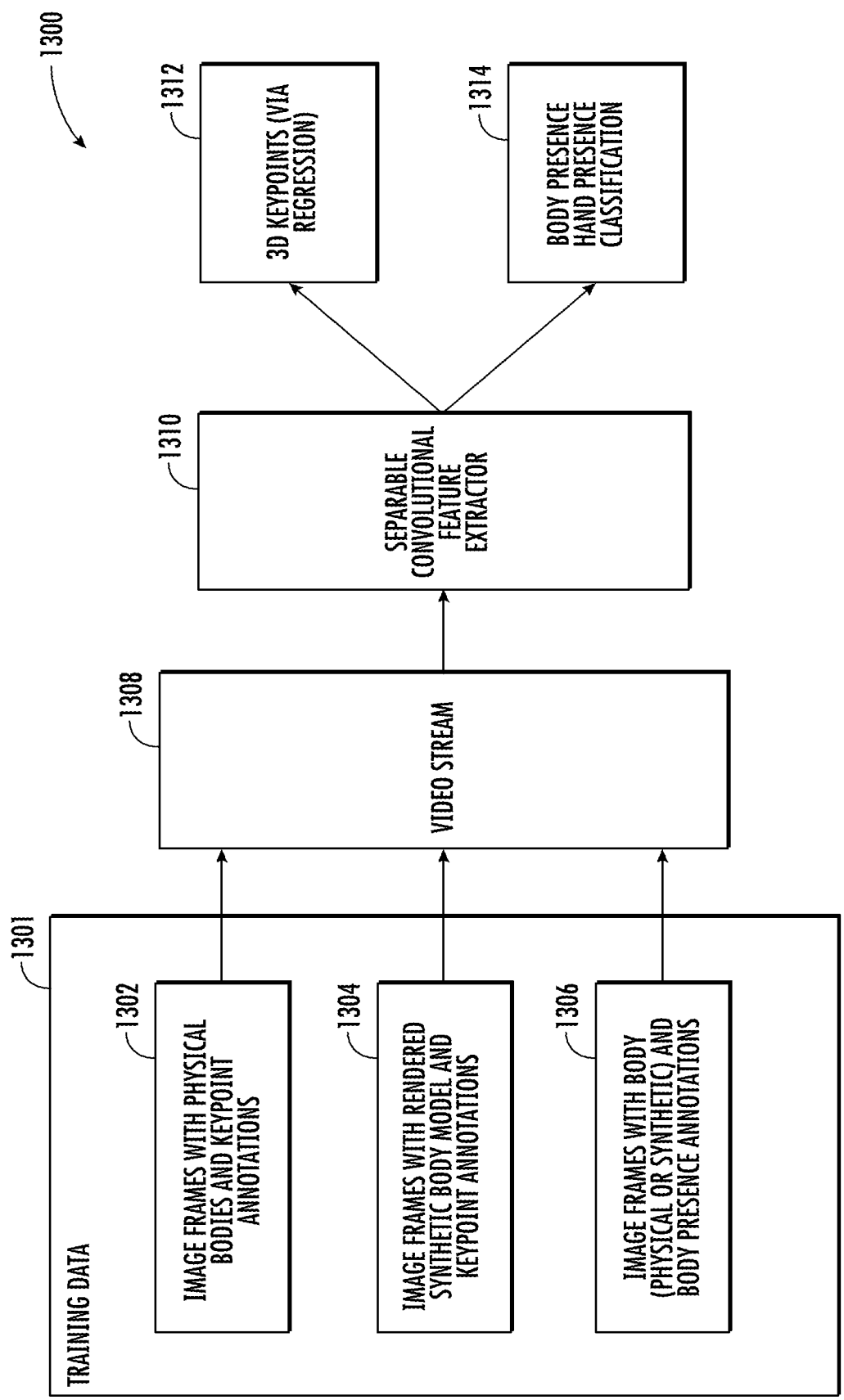
FIG. 29 depicts a block diagram of an example training schema used to train a machine-learned hand tracking system according to example embodiments of the present disclosure.

FIG. 29 depicts a block diagram of an example training schema used to train a machine-learned body tracking system according to example embodiments of the present disclosure. The training data 1301 used to train the body tracking system can include a first set of image frames 1302 that depict one or more physical bodies. The first set of image frames can be annotated with ground truth data that indicates body landmark positions for the physical body(s) depicted in the first set of images. The annotations can include three-dimensional coordinates in example embodiments. The coordinates can include a depth value taken from a depth map in some examples. The training data can include a second set of image frames 1304 annotated with ground truth data that indicates body landmark positions for one or more rendered synthetic body models that are depicted within the second set of annotated images frames. The second set of image frames can provide additional coverage for possible body poses and provide additional supervision on the nature of body geometry. The second set of image frames can include the synthetic body model rendered over various backgrounds. The annotations can include a mapping of the rendered synthetic body model to corresponding three-dimensional coordinates. By using a mixed training schema, a model can be trained that generalizes well in the real-world domain due to the physical real-world training examples, and that includes a range of body poses as provided by the synthetic body model examples. In some examples, the training data can include an optional third set of image frames 1306 annotated with ground truth data that indicates whether a body is present in the third set of image frames. The third set of image frames 1306 can be used to train the machine-learned body tracking system to detect body presence. In some examples, the first or second set of image frames can additionally or alternatively be annotated with ground truth data that indicates whether a body is present in the first or second set of image frames.

Figure 30:
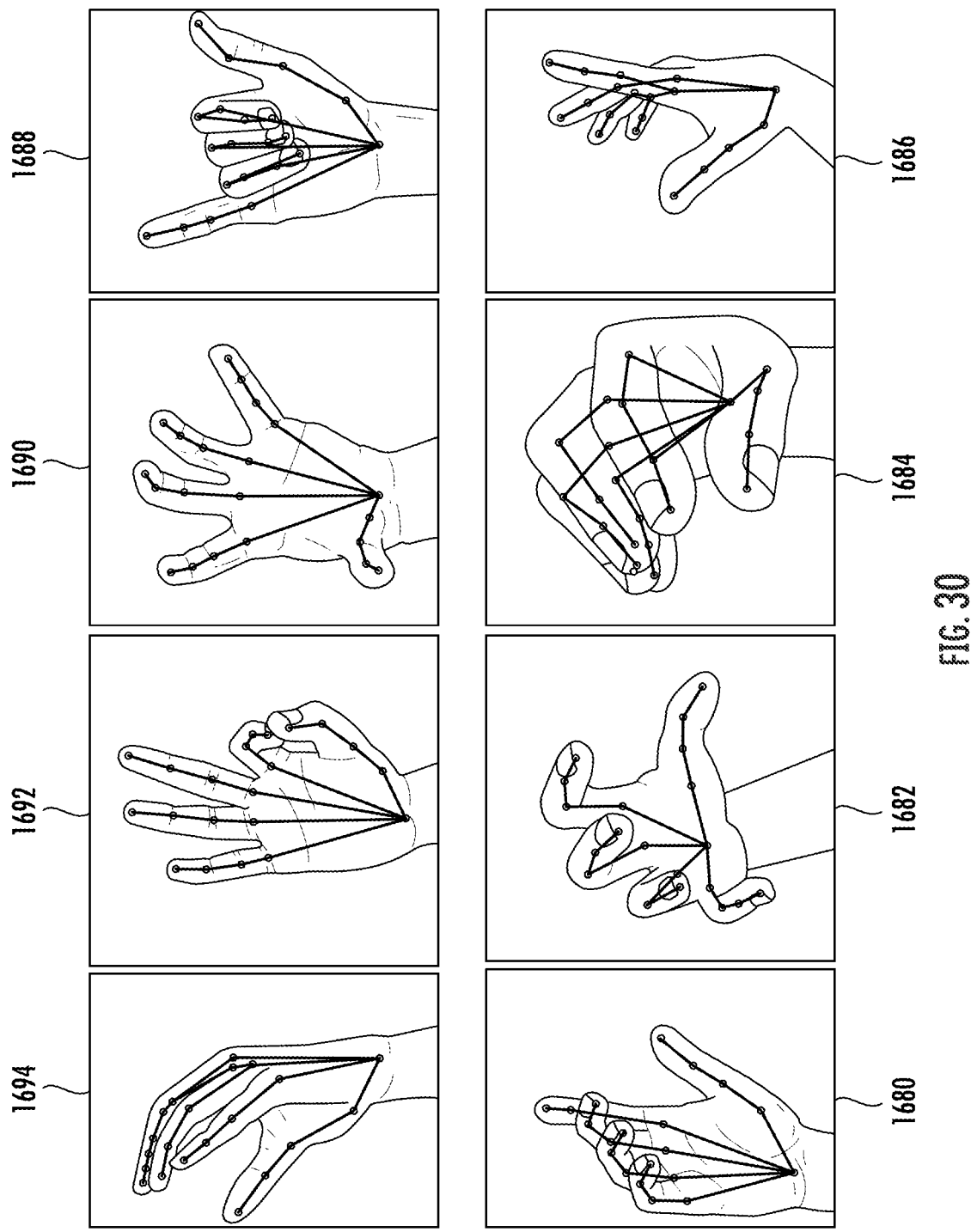
FIG. 30 depicts a flowchart illustrating an example method of training a hand tracking system according to example embodiments of the present disclosure.

FIG. 30 depicts example training image frames annotated with ground truth data that indicates the hand landmarks for the hands depicted in the respective image frames. Image frames 1688-1694 are image frames annotated with ground truth data that indicates hand landmark positions for one or more physical hands depicted within the set of annotated image frames. Image frames 1680-1686 are image frames annotated with ground truth data that indicates hand landmark positions for one or more rendered synthetic hand models that are depicted within the set of annotated images frames.

In some examples, the training data can be provided as one or more video streams 1308 of other groupings of data to a separable convolutional feature extractor 1310. Feature extractor 1310 can extract features from the training data. For example, the feature extractor can extract from an image frame features associated with hand landmarks. Based on the features extracted from an image frame, the hand landmark model can determine a set of three-dimensional coordinates 1312 for the hand landmarks. The hand landmark model can use a regression technique in some examples to generate a set of three-dimensional coordinates. Additionally, the hand landmark model can generate a classification indicating whether a hand is depicted within the image frame.

The predicted three-dimensional coordinates for an image frame can be compared with the annotations in the training data to determine one or more errors associated with the prediction. In some examples, a loss function can be determined based on a comparison of the predicted coordinates with the annotated coordinates. The loss function can be backpropagated to the machine-learned palm detection model and/or the machine-learned hand landmark model to train the machine-learned system. By way of example, the loss function can be backpropagated through the hand landmark model to modify one or more portions of the hand landmark model. For instance, one or more weights or other parameters associated with the model can be modified based on the loss function.

Figure 31:
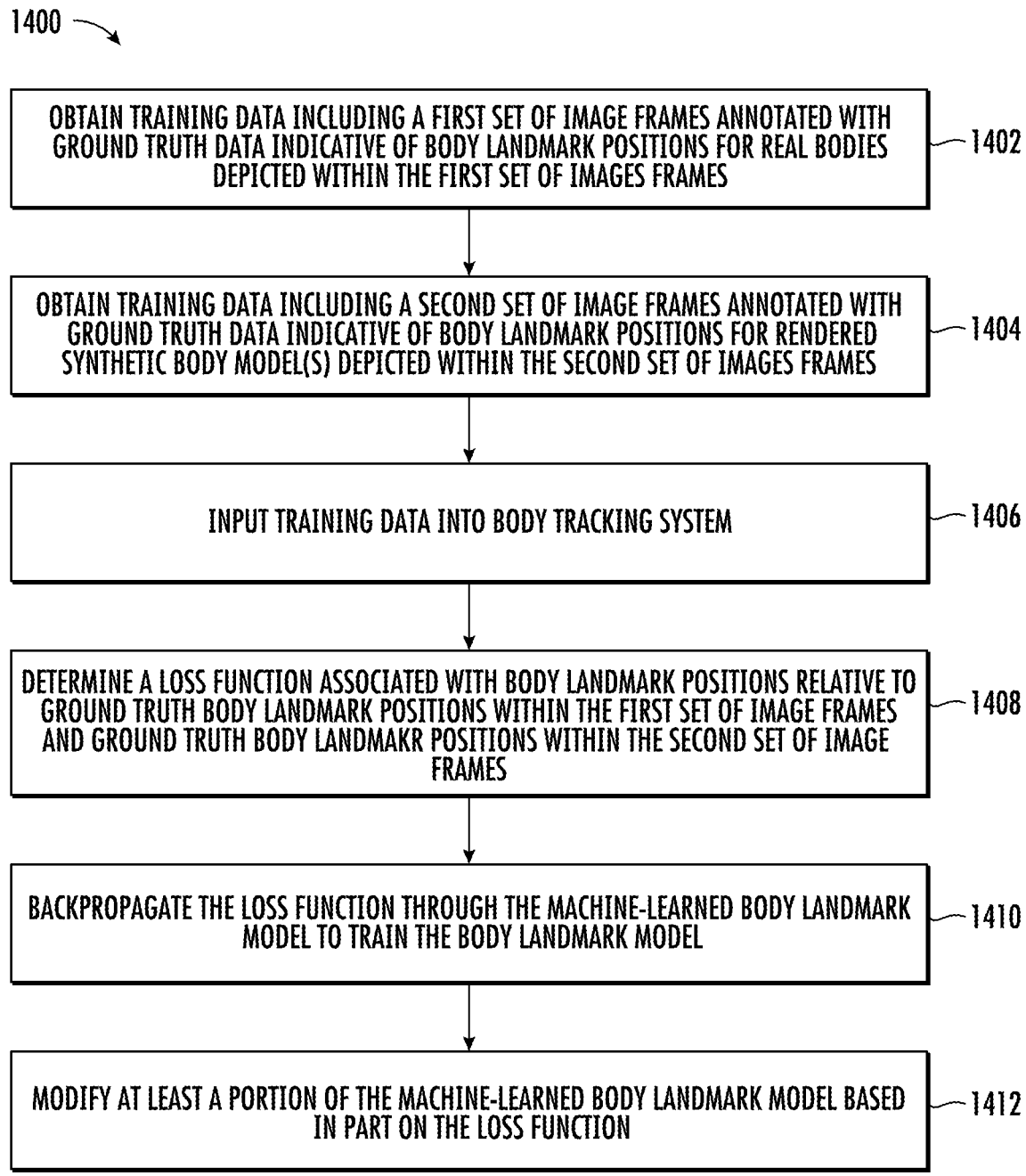
FIG. 31 depicts example training data annotated with ground truth data that indicates hand landmark positions.

FIG. 31 depicts a flowchart illustrating an example method 1400 of training a body tracking system according to the embodiments of the present disclosure. For example, a body tracking system in accordance with example embodiments can be trained to determine three-dimensional coordinates corresponding to a plurality of body landmark positions within an image frame and/or to detect whether a body is present in the image frame. Method 1400 can be performed by a computing system such as a training computing system 2150 of FIG. 36A in example embodiments.

At (1402), method 1400 can include obtaining training data including a first set of image frames annotated with ground truth data that indicates body landmark positions for one or more physical bodies depicted within the first set of images. In some examples, training data including the first set of image frames can be annotated with ground truth data that indicates three-dimensional coordinates corresponding to a plurality of body landmark positions. The three-dimensional coordinates can include a z-value (or depth value) taken from an image depth map for the first set of image frames.

At (1404), method 1400 can include obtaining training data including a second set of image frames annotated with ground truth data that indicates body landmark positions for one or more rendered synthetic body models that are depicted within the second set of annotated images frames. For example, a body model can be rendered in a variety of poses and mapped to a plurality of body landmark positions. In some examples, training data including synthetic body models can be annotated with ground truth data that indicates three-dimensional coordinates corresponding to a plurality of body landmark positions. The three-dimensional coordinates can include a z-value (or depth value) taken from an image depth map for the second set of image frames or can be generated using a computer-generated body model.

At (1406), method 1400 can include inputting the training data including a first set of image frames and a second set of image frames into the body tracking system. In some embodiments, the training data can be input to body landmark model 611. Additionally or alternatively, the training data can be input to palm detection model 162.

At (1408), method 1400 can include determining a loss function based on errors between body landmark positions detected by the machine-learned body landmark model and ground truth data that indicates body landmark positions for physical bodies depicted within the first set of images frames. Additionally or alternatively, the loss function can be determined based on errors between the detected landmark positions and ground truth data that indicates body landmark positions for a rendered synthetic body model depicted within the second set of images frames.

At (1410), method 1400 can include the training system can backpropagate the loss function to the machine-learned body tracking system to train the palm detection model and/or the body landmark model.

At (1412), method 1400 can include modifying at least a portion of the palm detection model and/or the machine-learned body landmark model based at least in part on the loss function. For example, the training system can modify one or more of the weights associated with the machine-learned palm detection or machine-learned body landmark model.

Figure 32:
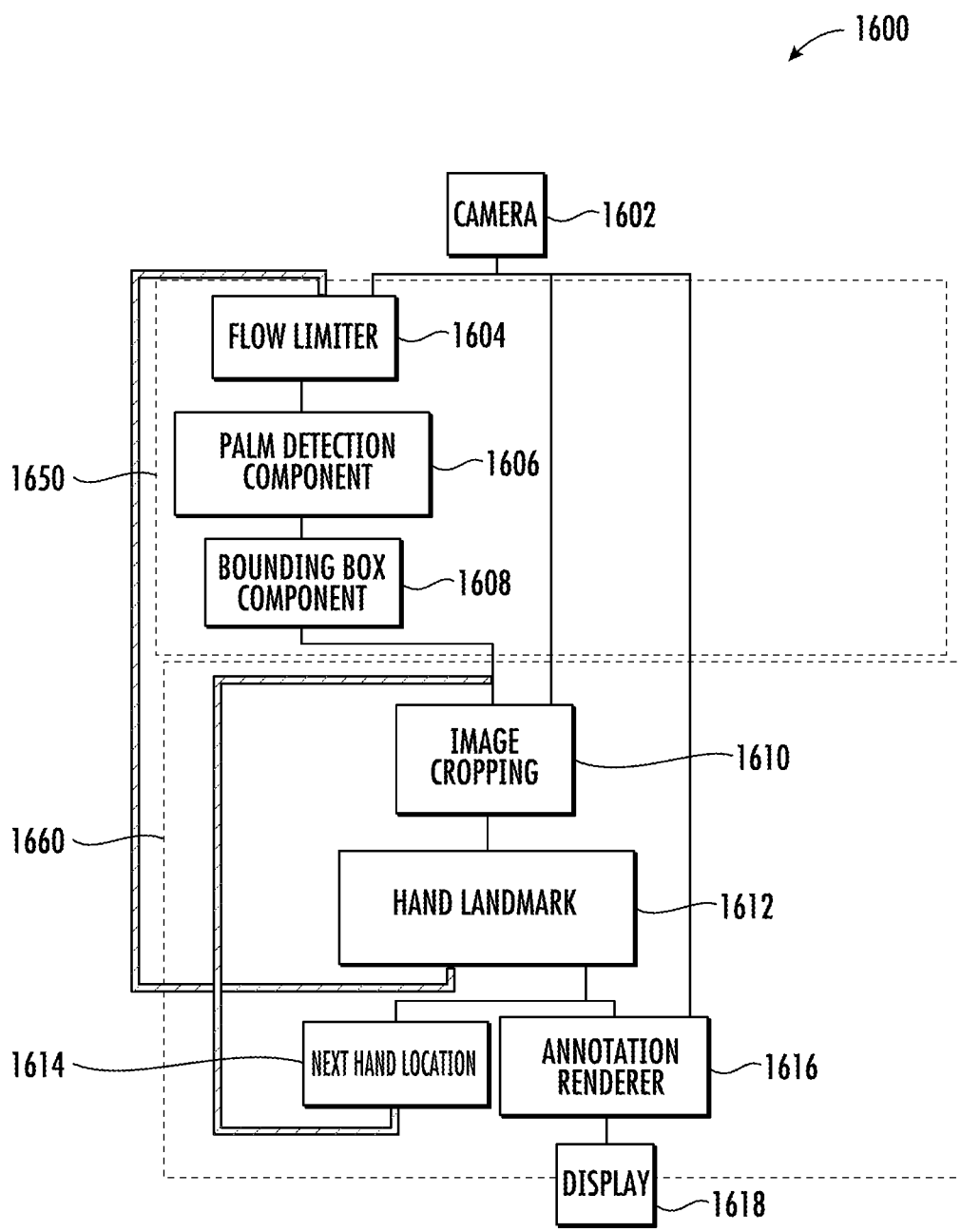
FIG. 32 depicts a block diagram of an example hand tracking system according to example embodiments of the present disclosure.

FIG. 32 depicts a block diagram of an example hand tracking system according to the embodiments of the present disclosure. FIG. 32 depicts one example implementation in which the hand tracking system includes a directed graph of modular components (e.g., calculators). In this example, the hand tracking system can be built as or otherwise include a graph hand tracking system including subgraphs for palm detection and hand landmark detection. A first subgraph 1650 can implement a palm detection model and a second subgraph 1660 can implement a hand detection model. It will be appreciated that the graph depicted in FIG. 32 is but one of many possible implementations of a hand tracking system in accordance with embodiments of the present disclosure. In this example, the hand tracking system can receive input image frames from an input video 1602 source (e.g., camera). However, the input image data can include image data from any image sensor such as a RADAR sensor or LIDAR sensor as earlier described.

The palm detection subgraph can include a flow limiter 1604 that throttles images flowing downstream through the hand tracking system. In some examples, the flow limiter passes the first input image unaltered through to the palm detection model 1606, and for subsequent images, waits for downstream models in the hand tracking system before passing another image frame. The throttling of image frames prevents downstream models from queuing incoming image frames, preventing latency and memory usage in real-time applications.

A palm detection model 1606 can be configured to detect one or more palms in an image frame. For example, the palm detection model can extract features associated with palms from image frames to detect and predict palm positions.

A bounding box component 1608 can generate an oriented bounding box indicating the position of a hand or palm within an image frame based on the detection from palm detection model 1606. In some examples, the bounding box component can expand a bounding box associated with a palm in order to identify a possible hand location. For instance, the palm detection model can estimate one or more first bounding boxes indicative of one or more detected palms in an image frame and expand and/or shift the one or more first bounding boxes to generate one or more second bounding boxes indicative of the location of an entire hand in the image frame.

The hand landmark model subgraph can include an image cropping component 1610 that is configured to can generate image data for an image frame region by cropping the corresponding image frame based at least in part on the respective orientated bounding box. The image cropping component can orient and/or crop an image frame based on the respective oriented bounding box to accurately display (or focus) the palm or hand in the image frame. In some examples, the image cropping component 1610 can be included in the palm detection model subgraph or outside either subgraph. The hand landmark model can be configured to obtain the image data for an image frame generated by the image cropping component 1610.

The hand landmark model subgraph can include a hand landmark component 1612 configured to detect a plurality of hand landmark positions (e.g., fingers, thumb, knuckles, joint positions, etc.) within the image frame region and generate three-dimensional coordinates corresponding to the hand landmark positions within the image frame region. For example, the hand landmark component 1612 can detect hand landmark positions based on the position of the palm or hand in the image frame and/or an orientation of the respective bounding box generated by the bounding box component 1608. In some examples, the hand landmark component 1612 can detect landmarks based at least in part on hand geometry of a depicted hand. In some examples, the hand landmark component 1612 can perform key-point localization to generate three-dimensional coordinates corresponding to the plurality of hand landmark positions. The hand landmark component 1612 can detect a plurality of hand landmark positions within an image frame and map the plurality of hand landmark positions as three-dimensional coordinates within the image frame.

The hand landmark subgraph can include a next hand location component 1614 that is configured to generate a rectangle that comprises the palm or hand in a subsequent image frame based in part on the hand landmark positions or the three-dimensional coordinates corresponding to the hand landmark positions in the current image frame. In some examples, the generated rectangle comprising the hand can be expanded and transformed such that the rectangle is likely to comprise the hand in the next image frame. This expanded rectangle can indicate the location of the hand in the image frame. The location of a hand in a subsequent video frame can be predicted based on the hand landmark positions or three-dimensional coordinates corresponding to the hand landmark positions within a current image frame or image frame region. In some examples, the next location component 1814 can orient and/or crop the subsequent image frame based on the predicted location of the hand in the subsequent image frame. In this manner, image data for the subsequent image frame can be generated that indicates the likely position of the hand based on the position of the hand in the current image frame. The image cropping component 1610 or the hand landmark component 1612 can proceed by detecting a plurality hand landmarks within the subsequent image frame and generate three-dimensional coordinates corresponding to the plurality of hand landmarks.

The hand landmark subgraph can include an annotation rendering component 1616 that is configured to render a hand skeleton for an image frame, based on the bounding box generated by the bounding box component 1608 and/or the hand landmark positions detected by the hand landmark component 1612. In some examples, the annotation rendering component 1616 can generate the hand skeleton for the respective image frame by overlaying the hand skeleton and bounding box on the respective input image frame.

Figure 33:
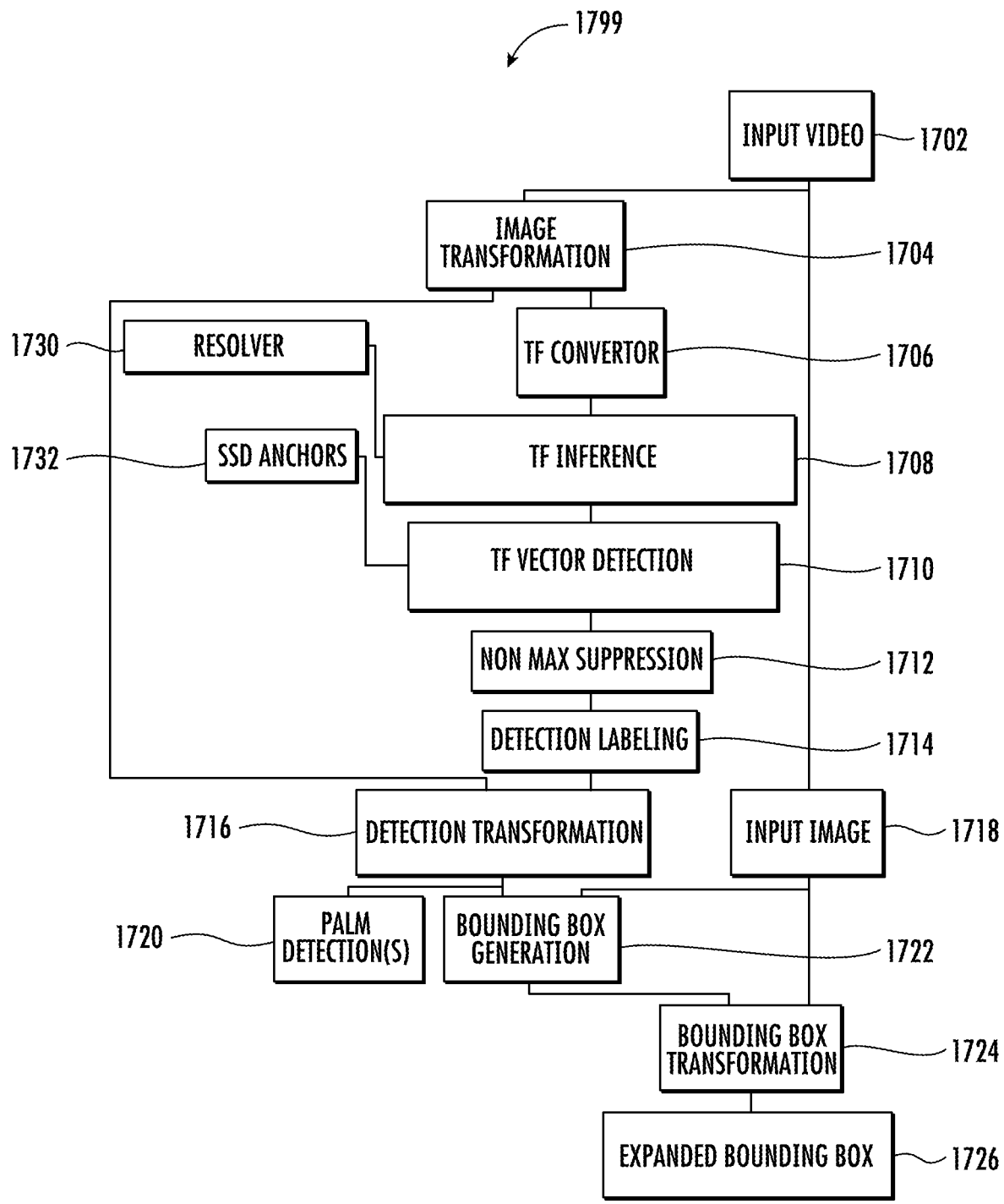
FIG. 33 depicts a block diagram of an example machine-learned palm detection model according to example embodiments of the present disclosure.

FIG. 33 depicts a block diagram of an example of a palm detection sub-graph in accordance with example embodiments of the present disclosure.

In this example, the palm detection subgraph of a hand tracking system can receive input image frames 1702 from an input source. The input image data can be any image data (and/or frames of video data) as referred to in the FIGS. The palm detection model can transform an input FIGS frame into an image of a pre-defined size (e.g., 800×800 pixels, 256×256, etc.). In some embodiments, the palm detection subgraph can transform an input image frame using an image transformation unit 1704 configured to transform an input image frame into an image of a pre-defined size.

The palm detection subgraph can include a resolver 1730 configured to resolve or otherwise support operations performed by the palm detection model and/or hand landmark model in the hand tracking system. The palm detection subgraph can include converter 1706 that is configured to convert a transformed image frame into one or more image tensors and to store the image tensor. An inference component 1708 can convert the image tensors into one or more outputs including a vector of tensors representing, for example, bounding boxes and/or key-point scores.

The palm detection subgraph can include a vector detection component 1710 that is configured to decode the vector tensors generated by the inference component 1708 into a vector of detections. Each detection within a vector of detections describes a detected object (e.g., bounding box, hand landmarks, 3D hand key-points, etc.).

One or more non-max suppression techniques can be applied to reject the excessive objects detected by the vector detection component 1710. For example, if multiple objects are detected such that multiple detections refer to the same object, some detections are combined and/or eliminated.

The objects detected by the vector detection component 1710 are labeled to indicate the object using a detection labeling component 1714. For example, if a palm is detected then the detection labeling component 1714 may label the detection "palm."

The palm detection subgraph can include a detection transformation component 1716 that is configured to adjust and/or transform the detected object(s) and/or their locations to correspond with the input image frame. After adjusting the locations of the detected palms or hands in the image frame, the palm detection subgraph estimates a bounding box 1720 that comprises the palm or hand detected. In some examples, the bounding box that encloses or comprises the detected hands or palms is oriented such that a line connecting the center of the wrist and metacarpophalangeal joint of the middle finger of the detected hand or palm is aligned to a y-axis of the bounding box 1720.

The palm detection subgraph can include a bounding box transformation component 1724 that is configured to generate a second bounding box that indicates the position of the hand in the image frame. In some examples, the bounding box transformation component 1724 is configured to expand and/or transform (e.g., rotate, scale, orient, etc.) the bounding box generated by bounding box generator 1722 to indicate the position of the entire hand. This expanded bounding box 1726 can indicate the location of the hand in the image frame based on the position of the palm in the image frame.

Figure 34:
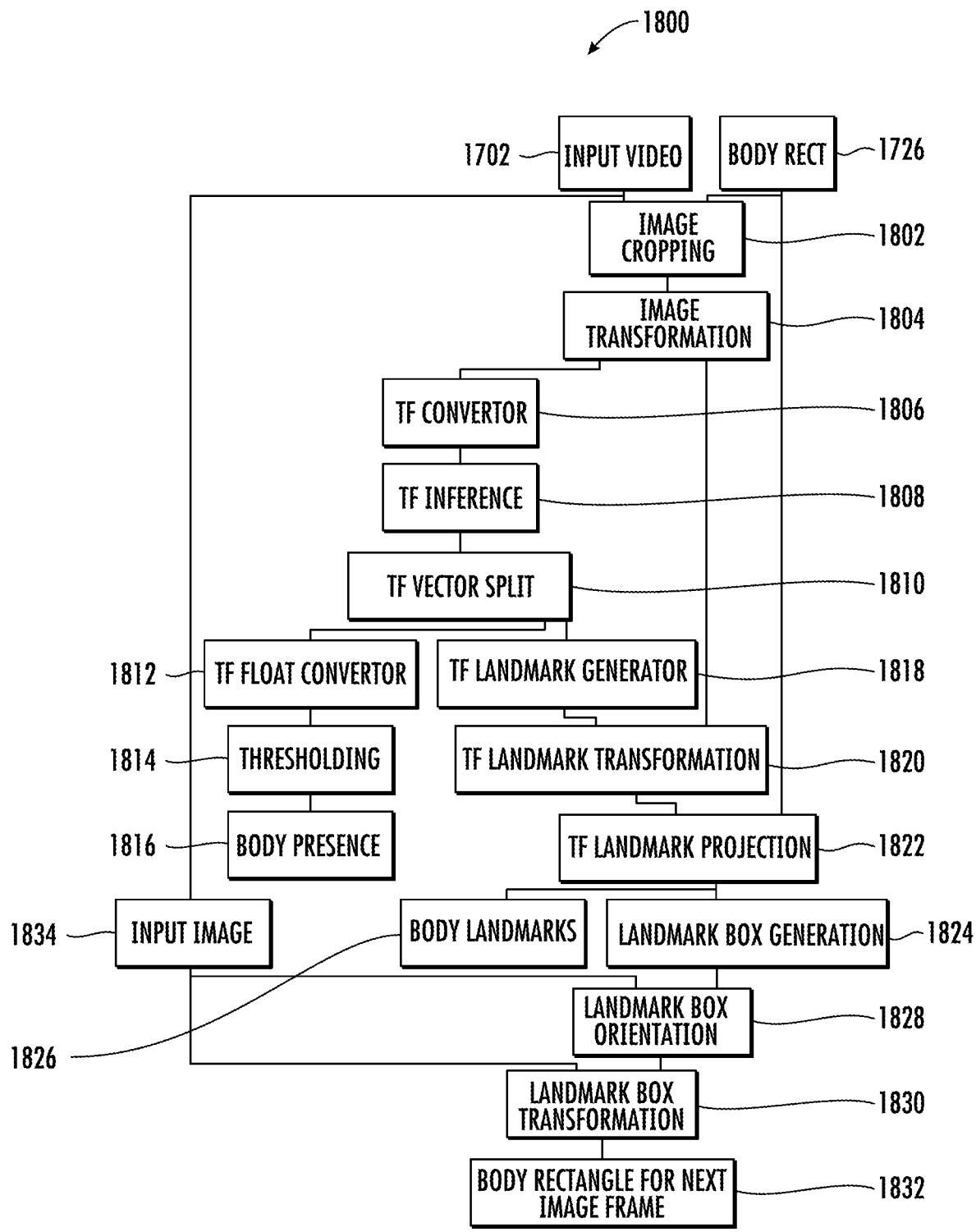
FIG. 34 depicts a block diagram of an example machine-learned hand landmark model according to example embodiments of the present disclosure.

FIG. 34 depicts a block diagram of an example body landmark sub-graph according to example embodiments of the present disclosure.

In this example, the body landmark subgraph of the body tracking system can receive a bounding box 1726 indicative of the position of a palm or body in the input image frame and the input image frame 1702 itself. In some embodiments, the body landmark subgraph can include an image cropping component 1802 that is configured to generate image data for an image frame region by cropping the corresponding image frame based at least in part on the respective orientated bounding box. The image cropping component 1802 can orient and/or crop an image frame based on the respective oriented bounding box to accurately display (or focus) the palm or body in the image frame. In some examples, the image cropping component 1802 can be included in the palm detection model subgraph or elsewhere. The body landmark model can be configured to obtain the image data for an image frame generated by the image cropping component.

The body landmark subgraph can include an image transformation component 1804 configured to transform the cropped image frame region generated by the image cropping component 1802. For example, the image transformation component can orient and/or crop an image frame region generated by the image cropping component 1802 based on the respective bounding box 1726 and to accurately display (or focus) the palm or body in the image frame. In some examples, the image transformation component 1804 can rotate, scale, orient, or otherwise transform the image frame region based on the orientation of the bounding box corresponding to bodies or palms.

The body landmark subgraph can include a converter 1806 configured to resolve or otherwise support operations performed by the palm detection model and/or body landmark model in the body tracking system. The body landmark subgraph can include converter 1806 that is configured to convert a transformed image frame region generated by the image transformation component 1804 into one or more image tensors and to store the image tensor.

The body landmark subgraph can include an inference component 1808 can convert the image tensors into one or more outputs including a vector of tensors representing, for example, bounding boxes and/or key-point scores.

The body landmark subgraph can include a vector split component 1810 configured to split the output vectors generated by the inference component 1808 into multiple vectors of tensors. For example, the output vector of tensors representing bounding boxes and/or key-point scores can be split into a first vector of tensors representing body presence inference in an image frame and a second vector of tensors representing body landmark positions.

The body landmark subgraph can include a float converter 1812. The float converter 1812 can be configured to convert the first set of tensors representing body presence inference in an image frame into a float that represents the confidence value that indicates a probability that a body is present in the image frame.

The body landmark subgraph can include a thresholding component 1814 configured to compare the confidence value generated by the float converter 1812 to a threshold value to determine whether a body is present in the image frame. In some examples, if the confidence value satisfies a pre-defined threshold, the body landmark model can generate and/or provide data indicative of three-dimensional coordinates corresponding to body landmark positions within the image frame. If the confidence value does not satisfy a pre-defined threshold, the body landmark model can input the corresponding image frame into the palm detection model.

The body landmark subgraph can include a body landmark generator 1818 that is configured to convert the second vector of tensors into a vector of body landmark positions or three-dimensional coordinates corresponding to the body landmark positions within an image frame.

The body landmark subgraph can include a landmark transformation component 1820 configured to adjust the detected body landmark positions to fit the input image frame. In some examples, the body landmark positions or three-dimensional coordinates can be normalized with respect to the input image.

The body landmark subgraph can include a landmark box generation component 1824 configured to map the body landmark positions or three-dimensional coordinates from the cropped image frame region to the corresponding full image frame. In some examples, the body landmark subgraph can include a landmark box generation component 1824 configured to generate a rectangle that comprises the palm or body detected.

In some examples, the body landmark subgraph can include a landmark orientation box 1828 configured to orient the body rectangle generated by landmark box generation 1824. In some examples, the rectangle that encloses or comprises the detected bodies or palms is oriented such that a line connecting the center of the wrist and metacarpophalangeal joint of the middle finger of the detected body or palm is aligned to a y-axis of the rectangle.

The body landmark subgraph can include a landmark box transformation component 1830 that is configured to expand the oriented rectangle generated by the landmark orientation box 1828. In some examples, the generated rectangle comprising the body can be expanded and transformed such that the rectangle is likely to comprise the body in the next image frame. This expanded rectangle can indicate the location of the body in the image frame. The location of a body in a subsequent image frame can be predicted based on the body landmark positions or three-dimensional coordinates corresponding to the body landmark positions within a current image frame or image frame region. In some examples, the landmark box transformation component 1830 can orient and/or crop the subsequent image frame based on the predicted location of the body in the subsequent image frame. In this manner, image data for the subsequent image frame can be generated that indicates the likely position of the body based on the position of the body in the current image frame.

Figure 35:
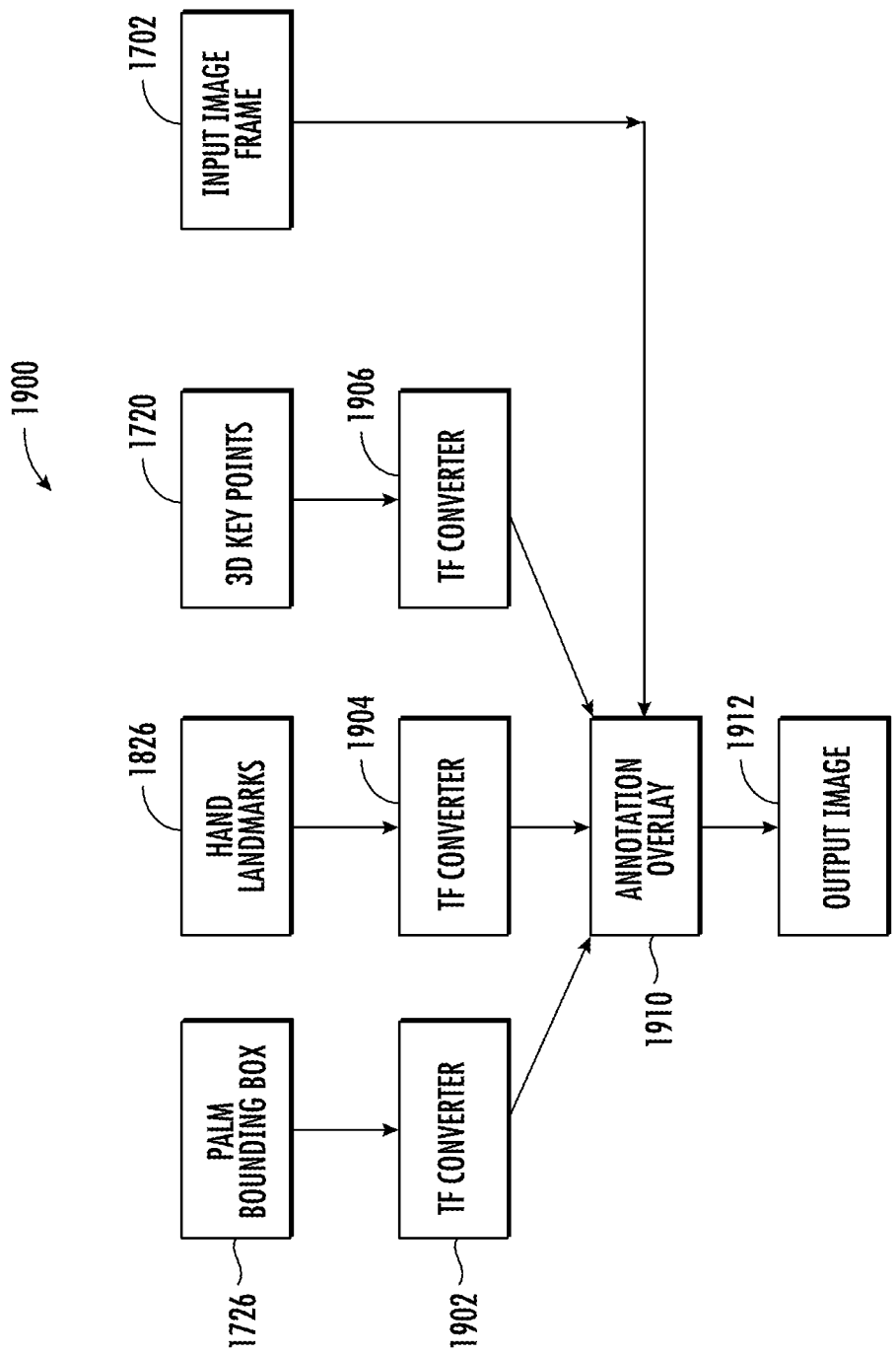
FIG. 35 depicts a block diagram of an example gesture recognition system according to example embodiments of the present disclosure.

FIG. 35 depicts a block diagram for an example rendering system 1900 according to example embodiments of the present disclosure. In this example, an annotated output image 1912 is generated based in part by overlaying a representation of a bounding box 1726 indicative of the position of a hand in an image frame, a plurality of hand landmark positions within the respective image frame 1826, or the bounding box 1720 that indicates the position of a palm in the image frame onto the respective input image frame 1702. In some examples, the bounding box data indicative of the position of a palm or hand in an image frame is converted into primitive display coordinates using one or more TF functions and/or model 1902. In some examples, the hand landmark positions within an image frame are converted into primitive display coordinates using one or more TF functions and/or model 1904. In some examples, the three-dimensional coordinates corresponding to the hand landmark positions within an image frame are converted into primitive display coordinates using one or more TF functions and/or model 1906.

FIG. 36A depicts a block diagram of an example body tracking computing system 2100 according to example embodiments of the present disclosure. The system 2100 includes a user computing device 2102, a server computing system 2130, and a training computing system 2150 that are communicatively coupled over a network 2180.

The user computing device 2102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 2102 includes one or more processors 2112 and a memory 2114. The one or more processors 2112 can be any suitable processing device (e.g., a processor core, a microprocessor, an ASIC, a FPGA, a controller, a microcontroller, etc.) and can be one processor or a plurality of processors that are operatively connected. The memory 2114 can include one or more non-transitory computer-readable storage mediums, such as RAM, ROM, EEPROM, EPROM, flash memory devices, magnetic disks, etc., and combinations thereof. The memory 2114 can store data 2116 and instructions 2118 which are executed by the processor 2112 to cause the user computing device 2102 to perform operations.

The user computing device 2102 can include a body tracking system 2120. The body tracking system 2119 can track bodies in image frames as described herein. One example of the body tracking system 2119 is shown in FIG. 21. However, systems other than the example system shown in FIG. 21 can be used as well.

In some implementations, the body tracking system 2119 can store or include one or more body landmark models 2120. For example, the body landmark models 2120 can be or can otherwise include various machine-learned models such as neural networks (e.g., deep neural networks) or other types of machine-learned models, including non-linear models and/or linear models. Neural networks can include feed-forward neural networks, recurrent neural networks (e.g., long short-term memory recurrent neural networks), convolutional neural networks or other forms of neural networks.

One example of a body tracking system including body landmark detection is discussed with reference to FIG. 21. However, the example body tracking system of FIG. 21 is provided as one example only. The models 2120 can be similar to or different from the model(s) in the example body tracking system.

In some implementations, the one or more body landmark models 2120 can be received from the server computing system 2130 over network 2180, stored in the user computing device memory 2114, and then used or otherwise implemented by the one or more processors 2112. In some implementations, the user computing device 2102 can implement multiple parallel instances of body landmark models 2120 (e.g., to perform parallel body landmark detection across multiple instances of input imagery).

Additionally or alternatively to the body tracking system 2119, the server computing system 2130 can include a body tracking system 2140. The body tracking system 2139 can perform body tracking as described herein.

Additionally or alternatively to the models 2120, one or more body landmark models 2140 can be included in or otherwise stored and implemented by the server computing system 2130 that communicates with the user computing device 2102 according to a client-server relationship. For example, the body landmark models 2140 can be implemented by the server computing system 2140 as a portion of a web service (e.g., an image processing service). Thus, one or more models 2120 can be stored and implemented at the user computing device 2102 and/or one or more models 2140 can be stored and implemented at the server computing system 2130. The one or more body landmark models 2140 can be the same as or similar to the models 2120.

The user computing device 2102 can also include one or more user input components 2122 that receive user input. For example, the user input component 2122 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, or other means by which a user can provide user input.

The server computing system 2130 includes one or more processors 2132 and a memory 2134. The one or more processors 2132 can be any suitable processing device (e.g., a processor core, a microprocessor, an ASIC, a FPGA, a controller, a microcontroller, etc.) and can be one processor or a plurality of processors that are operatively connected. The memory 2134 can include one or more non-transitory computer-readable storage mediums, such as RAM, ROM, EEPROM, EPROM, flash memory devices, magnetic disks, etc., and combinations thereof. The memory 2134 can store data 2136 and instructions 2138 which are executed by the processor 2132 to cause the server computing system 2130 to perform operations.

In some implementations, the server computing system 2130 includes or is otherwise implemented by one or more server computing devices. In instances in which the server computing system 2130 includes plural server computing devices, such server computing devices can operate according to sequential computing architectures, parallel computing architectures, or some combination thereof.

As described above, the server computing system 2130 can store or otherwise include one or more machine-learned body landmark models 2140. For example, the models 2140 can be or can otherwise include various machine-learned models. Example machine-learned models include neural networks or other multi-layer non-linear models. Example neural networks include feed forward neural networks, deep neural networks, recurrent neural networks, and convolutional neural networks. One example model 2140 is discussed with reference to FIG. 5.

The user computing device 2102 and/or the server computing system 2130 can train the models 2120 and/or 2140 via interaction with the training computing system 2150 that is communicatively coupled over the network 2180. The training computing system 2150 can be separate from the server computing system 2130 or can be a portion of the server computing system 2130.

The training computing system 2150 includes one or more processors 2152 and a memory 2154. The one or more processors 2152 can be any suitable processing device (e.g., a processor core, a microprocessor, an ASIC, a FPGA, a controller, a microcontroller, etc.) and can be one processor or a plurality of processors that are operatively connected. The memory 2154 can include one or more non-transitory computer-readable storage mediums, such as RAM, ROM, EEPROM, EPROM, flash memory devices, magnetic disks, etc., and combinations thereof. The memory 2154 can store data 2156 and instructions 2158 which are executed by the processor 2152 to cause the training computing system 2150 to perform operations. In some implementations, the training computing system 2150 includes or is otherwise implemented by one or more server computing devices.

The training computing system 2150 can include a model trainer 2160 that trains the machine-learned models 2120 and/or 2140 stored at the user computing device 2102 and/or the server computing system 2130 using various training or learning techniques, such as, for example, backwards propagation of errors. In some implementations, performing backwards propagation of errors can include performing truncated backpropagation through time. The model trainer 2160 can perform a number of generalization techniques (e.g., weight decays, dropouts, etc.) to improve the generalization capability of the models being trained.

In particular, the model trainer 2160 can train the body landmark models 2120 and/or 2140 based on a set of training data 2162. The training data 2162 can include, for example, a plurality of training images, where each training image has been labeled with ground truth data that indicates body landmark positions and/or body presence. For example, the label(s) for each training image can describe the location (e.g., in the form of a bounding shape) and/or body landmark positions of at least a portion of a body depicted by the training image. In some implementations, the labels can be manually applied to the training images by humans. In some implementations, the models can be trained using a loss function that measures a difference between a predicted detection and a ground-truth detection. In implementations which include multi-headed models, the multi-headed models can be trained using a combined loss function that combines a loss at each head.

In some implementations, if the user has provided consent, the training examples can be provided by the user computing device 2102. Thus, in such implementations, the model 2120 provided to the user computing device 2102 can be trained by the training computing system 2150 on user-specific data received from the user computing device 2102. In some instances, this process can be referred to as personalizing the model.

The model trainer 2160 includes computer logic utilized to provide desired functionality. The model trainer 2160 can be implemented in hardware, firmware, and/or software controlling a general purpose processor. For example, in some implementations, the model trainer 2160 includes program files stored on a storage device, loaded into a memory and executed by one or more processors. In other implementations, the model trainer 2160 includes one or more sets of computer-executable instructions that are stored in a tangible computer-readable storage medium such as RAM hard disk or optical or magnetic media.

The network 2180 can be any type of communications network, such as a local area network (e.g., intranet), wide area network (e.g., Internet), or some combination thereof and can include any number of wired or wireless links. In general, communication over the network 2180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

FIG. 36A illustrates one example computing system that can be used to implement the present disclosure. Other computing systems can be used as well. For example, in some implementations, the user computing device 2102 can include the model trainer 2160 and the training dataset 2162. In such implementations, the models 2120 can be both trained and used locally at the user computing device 2102. In some of such implementations, the user computing device 2102 can implement the model trainer 2160 to personalize the models 2120 based on user-specific data.

Figure 36B:
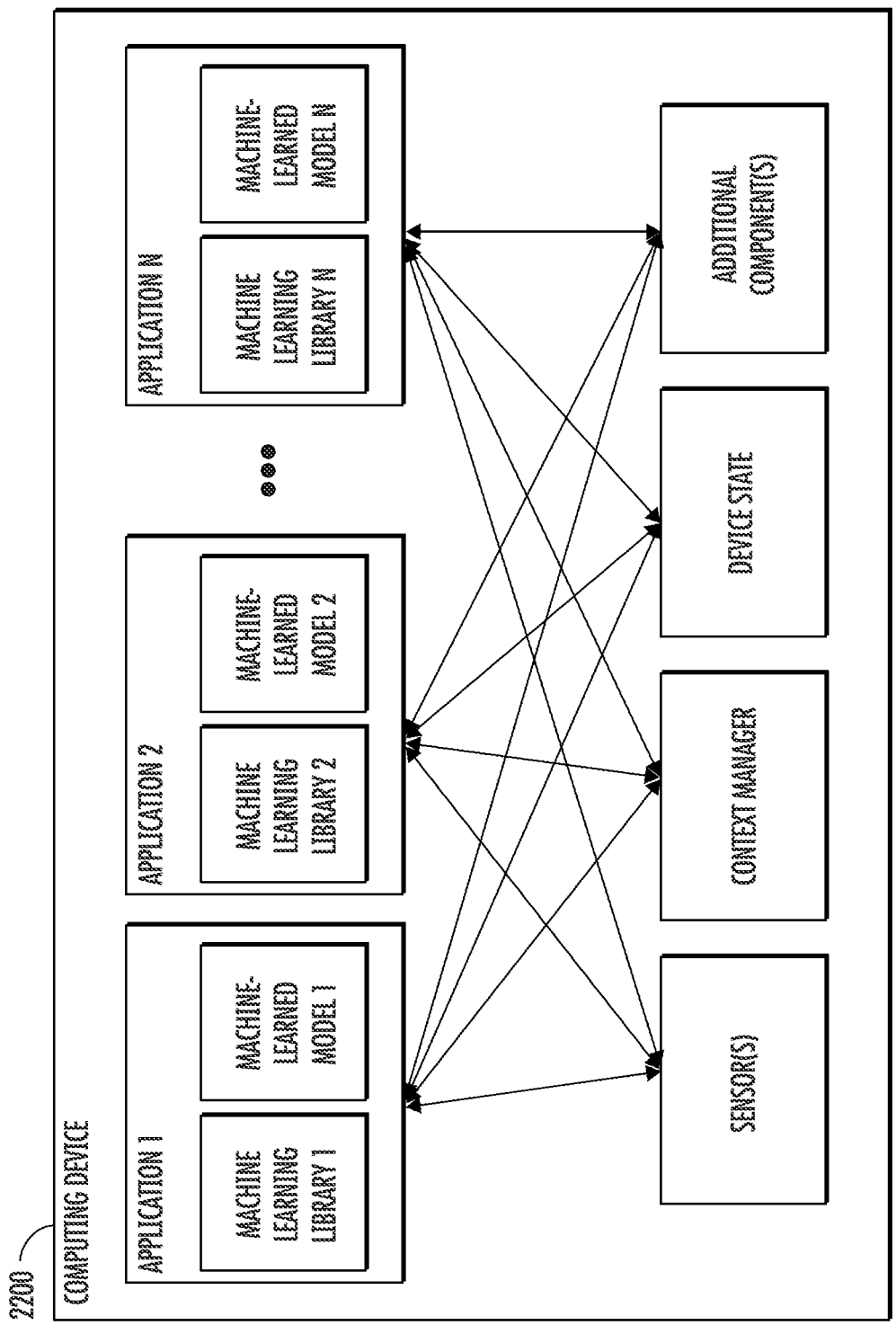
FIG. 36B depicts a block diagram of an example computing device according to example embodiments of the present disclosure.

FIG. 36B depicts a block diagram of an example computing device 2200 that performs according to example embodiments of the present disclosure. The computing device 2200 can be a user computing device or a server computing device.

The computing device 2200 includes a number of applications (e.g., applications 1 through N). Each application contains its own machine learning library and machine-learned model(s). For example, each application can include a machine-learned model. Example applications include a text messaging application, an email application, a dictation application, a virtual keyboard application, a browser application, etc.

As illustrated in FIG. 36B, each application can communicate with a number of other components of the computing device, such as, for example, one or more sensors, a context manager, a device state component, and/or additional components. In some implementations, each application can communicate with each device component using an API (e.g., a public API). In some implementations, the API used by each application is specific to that application.

Figure 36C:
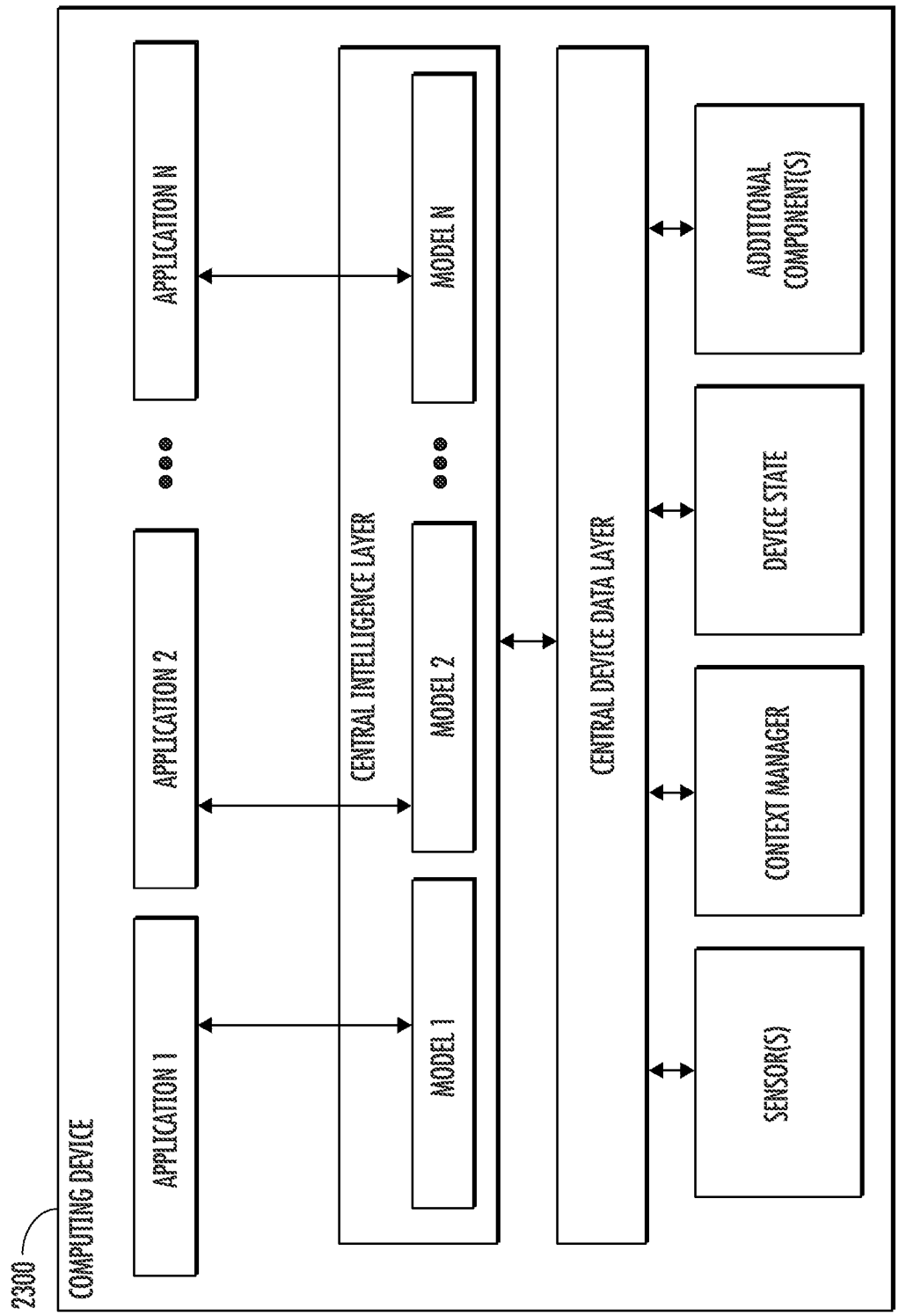
FIG. 36C depicts a block diagram of an example computing device according to example embodiments of the present disclosure.

FIG. 36C depicts a block diagram of an example computing device 2300 that performs according to example embodiments of the present disclosure. The computing device 2300 can be a user computing device or a server computing device.

The computing device 2300 includes a number of applications (e.g., applications 1 through N). Each application is in communication with a central intelligence layer. Example applications include a text messaging application, an email application, a dictation application, a virtual keyboard application, a browser application, etc. In some implementations, each application can communicate with the central intelligence layer (and model(s) stored therein) using an API (e.g., a common API across all applications).

The central intelligence layer includes a number of machine-learned models. For example, as illustrated in FIG. 36C, a respective machine-learned model (e.g., a model) can be provided for each application and managed by the central intelligence layer. In other implementations, two or more applications can share a single machine-learned model. For example, in some implementations, the central intelligence layer can provide a single model (e.g., a single model) for all of the applications. In some implementations, the central intelligence layer is included within or otherwise implemented by an operating system of the computing device 2300.

The central intelligence layer can communicate with a central device data layer. The central device data layer can be a centralized repository of data for the computing device 2300. As illustrated in FIG. 36C, the central device data layer can communicate with a number of other components of the computing device, such as, for example, one or more sensors, a context manager, a device state component, and/or additional components. In some implementations, the central device data layer can communicate with each device component using an API (e.g., a private API).

FIG. 37 depicts example body landmarks according to example embodiments of the present disclosure. For instance, landmarks 2810 can be descriptive of a body at a first point in time. Additionally and/or alternatively, landmarks 2820 can be descriptive of a body at a second point in time. For instance, the landmarks 2810 and 2820 can illustrate how the body shifts over time. As an example, landmark 2812 in landmarks 2810 can correspond to landmark 2822 in landmarks 2820. For instance, the landmarks 2810 and 2820 illustrate at least a portion of a time-series that can be output from the body landmark model based at least in part on video data depicting the user's body. In some examples, swing angle and/or frequency from limb(s), step frequency, amplitude, distance, and/or other biomarkers are able to be detected by the model. The example body landmarks depicted in FIG. 37 can be useful in motion analysis of a user, such as in evaluating gait/walking tests, evaluating a user's gestures in arising from a seat, or other full- or partial-body test of the user's motor skills.

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A method for facilitating a Parkinson's Disease ("PD") assessment of a patient according to a standardized assessment scale, comprising:

capturing, using a front-facing camera of a mobile device comprising a touchscreen, an inertial measurement unit (IMU), and a microphone, first video of a patient performing first test movements while holding the mobile device in a hand of the patient, the first test movements comprising touchscreen interactions with the touchscreen;

capturing, using the front-facing camera of the mobile device, second video of the patient performing second test movements while maintaining the mobile device on their person;

capturing, using the front-facing camera or a rear-facing camera of the mobile device, and with the mobile device having been placed out of the hand of the patient but nearby to a body of the patient, third video of the patient performing third test movements, the third test movements comprising standing and walking;

capturing one or more IMU readings using the IMU of the mobile device during at least one of the first test movements or the second test movements;

processing the first video, the second video, and the third video according to (i) a hand landmark model to generate one or more hand biomarkers, (ii) a face landmark model to generate one or more face biomarkers, and (iii) a body landmark model to generate one or more body biomarkers, wherein at least one of the hand biomarkers, the face biomarkers, or the body biomarkers are determined based on a time series of three-dimensional coordinates of a hand, a face, or a body of the patient, respectively;

determining an assessment score based on a standardized PD assessment by processing the hand biomarkers, the face biomarkers, the body biomarkers, the IMU readings, and the touchscreen interactions; and outputting the standardized PD assessment to the patient or a clinician.

2. The method of claim 1, wherein:

each of the hand landmark model, the face landmark model, and the body landmark model are configured such that they can collectively be stored entirely on the mobile device and can perform the processing of the first video, the second video, and the third video entirely on the mobile device without requiring offloading to any processor external to the mobile device; and wherein none of the first video, the second video, or the third video is transferred off of the mobile device at any time;

whereby the PD assessment is facilitated without any potential compromise to user privacy.

3. The method of claim 1, wherein the standardized PD assessment comprises at least one of a speech test, a facial expression test, a finger tapping test, a hand movement test, a hand pronation test, a hand supination test, a hand gesture test, a walking or gait analysis test, and/or a chair arising test.

4. The method of claim 1, wherein the standardized assessment scale comprises a Unified Parkinson Disease Rating Scale (UPDRS) or a similar standardized assessment scale.

5. The method of claim 1, wherein at least one of the hand landmark model, the face landmark model, or the body landmark model are configured to:

identify a plurality of body landmark positions in the first video, the second video, or the third video;

normalize one or more coordinates of the plurality of body landmark positions;

perform principal component analysis on the one or more coordinates of the plurality of body landmark positions; and extract one or more features from the one or more coordinates of the plurality of body landmark positions.

6. The method of claim 5, wherein the mobile device comprises a smartphone.

7. A computing system for generating movement disorder diagnostics, the computing system comprising:

one or more processors; and one or more non-transitory computer-readable media that collectively store:

a machine-learned body landmark model configured to obtain video data and identify a plurality of body landmark positions within the video data, wherein the plurality of body landmark positions comprises a time series of three-dimensional coordinates of a body in the video data;

a machine-learned biomarker model configured to determine one or more biomarkers based at least in part on the time series of three-dimensional coordinates of the plurality of body landmark positions;

a machine-learned movement health diagnostic model configured to predict a movement health condition based at least in part on the one or more biomarkers; and instructions, that, when implemented, cause the one or more processors to perform operations, the operations comprising:

obtaining the video data, the video data comprising one or more frames;

providing the video data as input to the machine-learned body landmark model;

receiving, as an output from the machine-learned body landmark model, data descriptive of the plurality of body landmark positions within the video data;

providing the data descriptive of the plurality of body landmark positions as input to the machine-learned biomarker model;

receiving, as an output from the machine-learned biomarker model, data descriptive of the one or more biomarkers;

providing the data descriptive of the one or more biomarkers to the machine-learned movement health diagnostic model; and receiving, as an output from the machine-learned movement health diagnostic model, data descriptive of a movement health condition comprising a diagnostic score descriptive of a performance on a clinical movement health diagnostic test.

8. The computing system of claim 7, wherein the clinical movement health diagnostic test comprises at least one of a speech test, a facial expression test, a finger tapping test, a hand movement test, a hand pronation test, a hand supination test, a hand gesture test, a walking or gait analysis test, and/or a chair arising test.

9. The computing system of claim 7, wherein the machine-learned body landmark model comprises a skeletal position model.

10. The computing system of claim 7, wherein the one or more biomarkers comprises distance between an index finger and a thumb over time.

11. The computing system of claim 7, wherein input to the machine-learned movement health diagnostic model further comprises motion data.

12. The computing system of claim 7, wherein the plurality of body landmark positions comprises positions on a hand or a face.

13. The computing system of claim 7, wherein the movement health diagnostic model comprises at least one of a logistical regression model, a random forest model, or a neural network.

14. The computing system of claim 7, wherein the machine-learned biomarker model is configured to track motion over the time series of three-dimensional coordinates of the plurality of body landmark positions to determine the one or more biomarkers.

15. A computer-implemented method for generating movement disorder diagnostics, the computer-implemented method comprising:

obtaining, by a computing system comprising one or more computing devices, video data comprising one or more frames;

determining, by the computing system, a plurality of body landmark positions based at least in part on the video data, wherein the plurality of body landmark positions comprises a time series of three-dimensional coordinates of a body in the video data;

determining, by the computing system, one or more biomarkers based at least in part on the time series of three-dimensional coordinates of the plurality of body landmark positions; and determining, by the computing system, a movement health condition based at least in part on the plurality of body landmark positions, wherein the movement health condition is based at least in part on the one or more biomarkers.

16. The computer-implemented method of claim 15, wherein the movement health condition comprises a diagnostic score, the diagnostic score descriptive of a performance on a clinical movement health diagnostic test.

17. The computer-implemented method claim 16, wherein the diagnostic score comprises a movement disorder severity score.

18. The computer-implemented method of claim 16, wherein the clinical movement health diagnostic test comprises at least one of a speech test, a facial expression test, a finger tapping test, a hand movement test, a hand pronation test, a hand supination test, a hand gesture test, a walking or gait analysis test, and/or a chair arising test.

19. The computer-implemented method of claim 15, wherein the machine-learned body landmark model comprises a skeletal position model.

20. The computer-implemented method of claim 15, wherein determining the one or more biomarkers comprises tracking motion over the time series of three-dimensional coordinates of the plurality of body landmark positions.

\* \* \* \* \*